United States Patent
Aigner et al.

(10) Patent No.: US 9,550,831 B2
(45) Date of Patent: *Jan. 24, 2017

(54) METHOD FOR TREATING PSORIASIS

(75) Inventors: Silke Aigner, Frankenthal (DE); Matthias Germer, Langen (DE); Frank Osterroth, Dietzenbach (DE); Christoph Uherek, Seligenstadt (DE); Elmar Kraus, Bad Vilbel (DE); Andrea Wartenberg-Demand, Linden (DE); Daniele Wolf, Dreieich (DE); Sibylle Kaiser, Zwingenberg (DE); Juergen Lindner, Frankfurt (DE); Christoph Bruecher, Eschborn (DE); Benjamin Daelken, Frankfurt am Main (DE); Gregor Schulz, Umkirch (DE)

(73) Assignee: BIOTEST AG, Dreieich (DE)

(*) Notice: Subject to any disclaimer, the term of this patent is extended or adjusted under 35 U.S.C. 154(b) by 0 days.

This patent is subject to a terminal disclaimer.

(21) Appl. No.: 12/880,768

(22) Filed: Sep. 13, 2010

(65) Prior Publication Data

US 2011/0059083 A1 Mar. 10, 2011

Related U.S. Application Data

(63) Continuation of application No. PCT/EP2009/052810, filed on Mar. 10, 2009.

(30) Foreign Application Priority Data

Mar. 13, 2008 (GB) ................................ 0804687.2
Sep. 29, 2008 (GB) ................................ 0817809.7

(51) Int. Cl.
*A61K 39/395* (2006.01)
*C07K 16/28* (2006.01)
*A61K 39/00* (2006.01)

(52) U.S. Cl.
CPC ..... *C07K 16/2812* (2013.01); *A61K 2039/505* (2013.01); *A61K 2039/545* (2013.01); *C07K 2317/24* (2013.01); *C07K 2317/56* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,530,101 A | 6/1996 | Queen et al. | |
| 5,604,209 A | 2/1997 | Ubasawa et al. | |
| 5,654,407 A | 8/1997 | Boyle et al. | |
| 5,690,933 A | 11/1997 | Cobbold et al. | |
| 5,777,085 A | 7/1998 | Co et al. | |
| 5,859,205 A | 1/1999 | Adair et al. | |
| 5,871,732 A | 2/1999 | Burkly et al. | |
| 5,886,152 A | 3/1999 | Nakatani et al. | |
| 6,037,454 A | 3/2000 | Jardieu et al. | |
| 6,056,956 A | 5/2000 | Cobbold et al. | |
| 6,270,766 B1 | 8/2001 | Feldman et al. | |
| 6,987,171 B1 | 1/2006 | Hunig et al. | |
| 7,074,403 B1 | 7/2006 | Goldenberg et al. | |
| 7,125,679 B2 | 10/2006 | Ashkar | |
| 7,138,118 B2 | 11/2006 | Le et al. | |
| 7,304,127 B2 | 12/2007 | Saxinger | |
| 7,338,658 B2* | 3/2008 | Hanna et al. | 424/130.1 |
| 7,452,981 B2 | 11/2008 | Wijdenes | |
| 7,722,873 B2 | 5/2010 | Lonberg | |
| 7,838,489 B2 | 11/2010 | Feldmann et al. | |
| 7,846,442 B2 | 12/2010 | Feldmann et al. | |
| 2001/0056066 A1 | 12/2001 | Bugelski et al. | |
| 2002/0058029 A1 | 5/2002 | Hanna | |
| 2002/0068057 A1 | 6/2002 | Feldmann et al. | |
| 2002/0099179 A1 | 7/2002 | Jolliffe et al. | |
| 2002/0187526 A1 | 12/2002 | Ruben et al. | |
| 2003/0166860 A1 | 9/2003 | Hunig et al. | |
| 2003/0170239 A1 | 9/2003 | Hering et al. | |
| 2003/0219403 A1* | 11/2003 | Frewin et al. | 424/85.2 |
| 2004/0092718 A1 | 5/2004 | Hunig | |
| 2004/0137000 A1 | 7/2004 | Lynn et al. | |
| 2004/0247594 A1 | 12/2004 | Hunig et al. | |
| 2006/0008457 A1 | 1/2006 | Hanke | |
| 2006/0009382 A1 | 1/2006 | Hanke et al. | |
| 2006/0051346 A1* | 3/2006 | Wijdenes | 424/133.1 |
| 2006/0121021 A1 | 6/2006 | Hunig | |
| 2006/0188493 A1 | 8/2006 | Thomas | |
| 2006/0246063 A1 | 11/2006 | Sakaguchi et al. | |

(Continued)

FOREIGN PATENT DOCUMENTS

EP 0344006 11/1989
EP 0449769 10/1991

(Continued)

OTHER PUBLICATIONS

Lack et al. (Br. J. Anaesth. (1997) 78 (5): 601-605).*
Becker et al. (Eur. J. Immunol. 2007. 37: 1217-1223).*
Rudikoff et al. (Proc. Natl. Acad. Sci. USA, 79: 1979-1 983, Mar. 1982).*
Colman P. M. (Research in Immunology, 145:33-36, 1994).*
Merriam Webster online dictionary definition of "dose," pp. 1-4, downloaded Nov. 14, 2014, http://www.merriam-webster.com/dictionary/dose.*
MedlinePlus dictionary sponsored by the National Institutes of Health and the National Library of medicine, pp. 1-3, downloaded Nov. 14, 2014, see http://www.merriam-webster.com/medlineplus/dose.*
Biotest Analyst Conference of Mar. 20, 2008, pp. 0-38.*

(Continued)

*Primary Examiner* — Zachary Skelding
(74) *Attorney, Agent, or Firm* — Shelly Guest Cermak; Cermak Nakajima & McGowan LLP

(57) ABSTRACT

The present invention provides pharmaceutical composition for treating an autoimmune disease comprising a pharmaceutically acceptable carrier and an agent capable of activating CD4+CD25+ regulatory T cells, wherein the composition is to be administered to a subject at most every 3 days.

13 Claims, 37 Drawing Sheets

(56) References Cited

U.S. PATENT DOCUMENTS

| | | | |
|---|---|---|---|
| 2007/0071745 A1 | 3/2007 | Umana et al. | |
| 2007/0077246 A1* | 4/2007 | Koenig et al. | 424/144.1 |
| 2007/0166307 A1 | 7/2007 | Bushell et al. | |
| 2007/0218062 A1 | 9/2007 | Irving | |
| 2007/0270431 A1 | 11/2007 | Tabunoki et al. | |
| 2008/0213280 A1 | 9/2008 | Benyunes | |
| 2009/0123477 A1 | 5/2009 | Hanke et al. | |
| 2011/0059082 A1 | 3/2011 | Germer et al. | |
| 2011/0059084 A1 | 3/2011 | Osterroth et al. | |
| 2011/0229465 A1 | 9/2011 | Osterroth et al. | |

FOREIGN PATENT DOCUMENTS

| | | |
|---|---|---|
| EP | 0568925 | 11/1993 |
| EP | 1161955 | 12/2001 |
| EP | 1241249 | 9/2002 |
| EP | 1460088 | 9/2004 |
| EP | 2333110 A1 | 6/2011 |
| GB | 2376467 | 12/2002 |
| JP | 2-152989 A | 6/1990 |
| JP | 2006-511516 A | 4/2006 |
| JP | 2009-521956 A | 6/2009 |
| JP | 2009-529915 A | 8/2009 |
| WO | WO90/07861 | 7/1990 |
| WO | WO90/13562 | 11/1990 |
| WO | WO90/15152 | 12/1990 |
| WO | WO91/09966 | 7/1991 |
| WO | WO94/08619 | 4/1994 |
| WO | WO95/09652 | 4/1995 |
| WO | WO97/09351 A1 | 3/1997 |
| WO | WO97/29131 | 8/1997 |
| WO | WO98/14211 | 4/1998 |
| WO | WO01/16182 A2 | 3/2001 |
| WO | WO01/93908 | 12/2001 |
| WO | WO02/22212 A2 | 3/2002 |
| WO | WO02/062335 A2 | 8/2002 |
| WO | WO02/085405 A2 | 10/2002 |
| WO | WO02/102853 | 12/2002 |
| WO | WO2004/024097 | 3/2004 |
| WO | WO2004/050016 A2 | 6/2004 |
| WO | WO2004/067554 A2 | 8/2004 |
| WO | WO2004/083247 | 9/2004 |
| WO | WO2004/112835 | 12/2004 |
| WO | WO2005/019254 | 3/2005 |
| WO | WO2006/002377 | 1/2006 |
| WO | WO2006/050949 | 5/2006 |
| WO | WO2006/055077 | 5/2006 |
| WO | WO2007/019865 | 2/2007 |
| WO | WO2007/111661 A2 | 10/2007 |
| WO | WO2007/117602 | 10/2007 |
| WO | WO2007/130697 A2 | 11/2007 |
| WO | WO2007/135684 | 11/2007 |
| WO | WO2008/092905 A2 | 8/2008 |
| WO | WO2008/982895 | 8/2008 |
| WO | WO2008/134046 | 11/2008 |
| WO | WO2009/112592 | 9/2009 |
| WO | WO2010/022341 | 2/2010 |

OTHER PUBLICATIONS

Lobo et al., Journal of Pharmaceutical Sciences, vol. 93, No. 11, Nov. 2004, pp. 2645-2668.*
Vajdos et al. (J Mol Biol. Jul. 5, 2002;320(2):415-28).*
Makinen et al., Clin Exp Rheumatol 2006; 24 (Suppl.43): S22-S28.*
Kettleborough, C. A., et al., "Humanization of a mouse monoclonal antibody by CDR-grafting: the importance of framework residues on loop conformation," Protein Eng. 1991;4(7):773-783.
Keymeulen et al., Insulin Needs after CD3-Antibody Therapy in New-Onset Type 1 Diabetes. New Engl. J. Med, 2005; 352(25): 2598-2608.
Keystone et al., Radiographic, clinical, and functional outcomes of treatment with adalimumab (a human anti-tumor necrosis factor monoclonal antibody) in patients with active rheumatoid arthritis receiving concomitant methotrexate therapy: a randomized, placebo-controlled, 52-week trial. Arthritis Rheum. May 2004;50(5):1400-11.
Keystone et al., Golimumab, a human antibody to tumour necrosis factor {alpha} given by monthly subcutaneous injections, in active rheumatoid arthritis despite methotrexate therapy: the GO-FORWARD Study. Ann Rheum Dis. Jun. 2009;68(6):789-96. Epub Dec. 9, 2008.
Kim et al., When Does Rheumatoid Arthritis Begin and Why Do We Need to Know? Arthritis & Rheumatism 2000;43 (3):473-484.
Kingsley et al., CD4+CD25+ regulatory T cells prevent graft rejection: CTLA-4- and IL-10 dependent immunoregulation of alloresponses. J Immunol. 168: 1080 (2002).
Kraan et al., "Asymptomatic Synovitis Precedes Clinically Manifest Arthritis," Arthritis & Rheumatism 1998;41 (8):1481-1488.
Kingsley et al., Immunogenetic and cellular immune mechanism in rheumatoid arthritis: relevance to new therapeutic strategies. Br J Rheumatol, 29, 58-64, 1990.
Kipps et al., Importance of immunoglobulin isotype in human antibody-dependent, cell-mediated cytotoxicity directed by murine monoclonal antibodies, J. Exp. Med. 1985; 161: 1-17.
Kon et al., Randomised, dose-ranging, placebo-controlled study of chimeric antibody to CD4 (keliximab) in chronic severe asthma, Lancet Oct. 3, 1998; 352 (9134):1109-13.
Kon et al., The effects of an anti-CD4 monoclonal antibody, keliximab, on peripheral blood CD4zT-cells in asthma. Eur Respir J. 18(1): 45-52 (2001).
König et al., Glycosylation of CD4. J. Biol. Chem. 263, 9502-9507 (1988).
Korndörfer et al., Structural Mechanism of Specific Ligand Recognition by Lipocalin Tailored for the Complexation of Digoxigenin, J. Mol. Biol. Jul. 4, 2003; 330, 385-396.
Kwong et al., Structure of an HIV gp120 envelope glycoprotein in complex with the CD4 receptor and a neztralizing human antibody, Nature 393, 648-659 (1998).
Kriegel et al., Defective suppressor function of human CD4+CD25+ regulatory T cells in autoimmune polyglandular syndrome type II. J Exp Med, 199: 1285-1291, 2004.
Kuritzkes et al., Antiretroviral activity of the anti-CD4 monoclonal antibody TNX-355 in patients infected with HIV type 1. J. Infect. Dis. 2004 ;189 :286-91.
Liu et al., The presence of cytokine-suppressive CD4+CD25+ T cells in the peripheral blood and synovial fluid of patients with rheumatoid arthritis. Scand J Immunol, 62 (3): 312-317, 2005.
Strom et al. Therapeutic Approach to Organ Transplantation, (Therapeutic Immunology edited by Austen et al., Blackwell Science, Cambridge, MA, 1996; pp. 451-456).
Lam TK, Leung DT: More on simplified calculation of body-surface area. N Engl J Med Apr. 28, 1988;318(17):1130.
Lamarre et al., The MHC-Binding and gp120-Binding Functions of CD4 are Separable, Science 245, 743-746 (1989).
Lanza et al., Active immunity against the CD4 receptor by using an antibody antigenized with residues 41-55 of the first extracellular domain, PNAS USA 90, 11683-11687 (1993).
Lawendowski et al., Solid phase epitope recovery. J Immunol., (2002) 169: 2414-2421).
Levings, M. K., et al., Human CD4+CD25+T Regulatory Cells Suppress Naïve and Memory T Cell Proliferation and can be Expanded In Vitro without Loss of Function, J. Exp. Med. 2001;193(11):1295-1301.
Lindley, S., et al. Defective suppressor function in CD4(+)CD25(+) T-cells from patients with type 1 diabetes. Diabetes 54, 92-99 (2005).
Ling et al., Relation of CD4+CD25+ regulatory T-cell suppression of allergen-driven T-cell activation to atopic status and expression of allergic disease. Lancet (2004) 363(9409): 608-15.
Lipsky et al., Infliximab and Methotrexate in the treatment of rheumatoid arthritis. The New England Journal of Medicine, vol. 343; pp. 1594-1602; Nov. 30, 2000.
Lin, C.H. & Hunig, T. Efficient expansion of regulatory T cells in vitro and in vivo with a CD28 superagonist. Eur J Immunol 33, 626-638 (2003).

(56) References Cited

OTHER PUBLICATIONS

Livesay et al., Conserved sequence and structure association motifs in antibody-protein and antibody hapten complexes, Prot. Eng. Des. & Select. 17, 463-472 (2004).
Lorenz et al. Biological Agents in Rheumatoid Arthritis. BioDrugs Apr. 1998;9 (4): 303-324.
Lusky, M., et al., "Inhibition of SV40 replication in simian cells by specific pBR322 DNA sequences," Nature 1981;293:79-81.
Luggen et al., Results of a phase II double-blind, randomized study of a nondepleting anti-CD4 monoclonal antibody (Clenoliximab) given in combination with methotrexate (MTX) in patients with moderate to severe rheumatoid arthritis. Annals of Rheum. Dis. 2003; 62(1): 99.
Lusso et al., CD4 is a critical component of the receptor for human herpes virus 7: Interference with human immunodeficiency virus, Proc. Natl. Acad. Sci. USA 91, 3872-3876 (1994).
Maddon et al., The isolation and nucleotide sequence of a cDNA encoding the T cell surface protein T4. Cell. 1985; 42(1):93-104.
Maloy et al., CD4+ CD25+ TR cells suppress innate immune pathology through cytokine-dependent mechanisms. J. Exp. Med. (2003); 197(1): 111-119.
Mason et al., CD4 coating, but not CD4 depletion, is a predictor of efficacy with primatized monoclonal anti-CD4 treatment of active rheumatoid arthritis. J Rheumatol. 29(2): 220-9 (2002).
Mattheakis et al., An in vitro polysome display system for identifying ligands from large peptide libraries. PNAS 1994; 91(19):9022-6.
Mazerolles et al., A synthetic peptide mimicking the HLA-DR 82-binding site for CD4+ T cell adhesion to B cells and CD4+ T cell activation, Int. Immunology 8, 267-274 (1996).
Marie et al., TGF-beta1 maintains suppressor function and Foxp3 expression in CD4+CD25+ regulatory T cells. J Exp Med. Apr. 4, 2005;201(7):1061-7.
McKeithan, Kinetic proofreading in T-cell receptor signal transduction, PNAS 1995, 92; 5042-5046.
Mima et al., Transfer of rheumatoid arthritis into severe combined immunodeficient mice. The pathogenic implications of T cell populations oligoclonally expanding in the rheumatoid joints. J Clin Invest; 96:1746-1758, 1995.
Mizkami et al., Binding region for human immunodeficiency virus (HIV) and epitopes for HIV-blocking monoclonal antibodies of the CD4 molecule defined by site-directed mutagenesis. Proc. Natl. Acad. Sci. USA 1988;85:9273-9277.
Moebius et al., Human immunodeficiency virus gp120 binding C'C" ridge of CD4 domain 1 is also involved in interaction with class II major histocompatibility comlex molecules, PNAS USA 89, 12008-120012 (1992).
Moebius et al., Delination of an extended surface contact area on human CD4 involved in class II major histocompatibility complex binding, Proc. Natl. Acad. Sci. USA 90, 8259-8263 (1993).
Moore and Stevenson, New Targets for Inhibitors of HIV-1 Replication, Nature Rev. Mol. Cell Biol. 1, 40-49 (2000).
Moreau et al., Bioinformatics. Discontinuous epitope prediction based on mimotope analysis May 1, 2006 1;22(9):1088-95. Epub Jan. 24, 2006.
Morgan et al., CD25+ cell depletion hastens the onset of severe disease in collagen-induced arthritis. Arthritis and Rheumatism, 48 (5): 1452-1460, (2003).
Mottet et al., Cutting Edge: Cure of Colitis by CD4+CD25+ Regulatory T Cells. J. Immunol. (2003); 170: 3939-3943.
Mottonen et al., CD4+CD25+ T cells with the phenotypic and functional characteristics of regulatory T cells are enriched in the synovial fluid of patients with rheumatoid arthritis. Clin Exp Immunol,140 (2): 360-367, 2005.
Morel et al., Down-regulation of lymphocyte CD4 antigen expression by administration of anti-CD4 monoclonal antibody. Clin. Immunol. Immunopath. 1992; 64(3): 248-253.
Morel et al., "Internalization and Degradation of Anti-CD4 Monoclonal Antibodies Bound to Human Peripheral Blood Lymphocytes," Mol. Immunol. 1993;30(7):649-657.
Morel, P., et al., "Anti-CD4 Monoclonal Antibody Administration in Renal Transplanted Patients," Clin. Immunol. Immunopath. 1990;56:311-322.
Morel, P., et al., "Anti-CD4 Monoclonal Antibody Therapy in Severe Psoriasis," J. Autoimmun. 1992;5:465-477.
Mount, D. W., et al., "Microcomputer programs for back translation of protein to DNA sequences and analysis of ambiguous DNA sequences," Nucl. Acids Res. 1984;12(1):819-823.
Mosteller RD: Simplified Calculation of Body Surface Area. N Engl J Med Oct. 22, 1987;317(17):1098.
Mourad et al., Humanized IgG1 and IgG4 anti-CD4 monoclonal antibodies: Effects on Lymphocytes in the Blood, Lymph Nodes, and Renal Allografts in Cynomolgus Monkeys1. Transplantation 65(5): 632-41 (1998).
Muyldermans et al., Camelid immunoglobulin and nanobody technology. Veterinary Immunology and Immunopathology, 128; 1-3; pp. 178-183 (2009) Epub. Oct. 17, 2008.
Myszka et al., Energetics of the HIV gp120-CD4 binding reaction, Proc. Natl. Acad. Sci. USA 97, 9026-9031 (2000).
Nakamura et al., Cell contact-dependent immunosuppression by CD4(+)CD25(+) regulatory T cells is mediated by cell surface-bound transforming growth factor beta. J Exp. Med. 194: 629-644 (2001).
Nakanishi et al., Structural and thermodynamic analyses of interaction between a humanized antibody and its antigen: The case of anti-lysozyme antibody, HyHEL-10, Photon Factory Activity Report 2006 #24 Part p. 248.
Nakatani et al., "Functional Expression of Human Monoclonal Antibody Genes Directed Against Pseudomonal Exotoxin A in Mouse Myeloma Cells" Biotechnology 1989; 7: 805-810.
Ng et al., Pharmacokinetics/pharmacodynamics of nondepleting anti-CD4 monoclonal antibody (TRX1) in healthy human volunteers. Pharm Res. Jan. 2006;23(1):95-103. Epub Nov. 30, 2006.
Nimmerjahn and Ravetch, Fc gamma receptors as regulators of immune responses. Nature Reviews Immunology 2008. 8: 34.
Newsome, G. Guidelines for the management of rheumatoid arthritis: 2002 update. J Am Acad Nurse Pract 14, 432-437 (2002).
Orlandi, R., et al., "Cloning immunoglobulin variable domains for expression by the polymerase chain reaction," Proc, Natl. Acad. Sci. USA 1989;86:3833-3837.
Osterburg, G., et al,, "Computer programs for the analysis and the management of DNA sequences," Nuc. Acids Res. 1982;10(1):207-216.
Oosterhout et al., Regulatory T-lymphocytes in asthma. Eur. Resp. Journal (2005); 26: 918-932.
Panaccione, R., Ferraz, J.G. & Beck, P. Advances in medical therapy of inflammatory bowel disease. Curr Opin Pharmacol 5, 566-572 (2005).
Panka, et al., "Variable region framework differences result in decreased or increased affinity of variant anti-digoxin antibodies," Proc. Natl. Acad. Sci. 1988;85:3080-3084.
Pandiyan et al., CD4+CD25+Foxp3+ regulatory T cells induce cytokine deprivation—mediated apoptosis of effector CD4+ T cells. Nature Immunol. (2007) 8 1353-1362.
Peters et al., Clinical grade Treg: GMP isolation, improvement of purity by CD127 Depletion, Treg expansion, and Treg cryopreservation. PLoS One. Sep. 8, 2008;3(9):e3161.
Piatier-Tonneau et al., Characterization of 18 workshop anti-CD4 mAb: epitope mapping to CD4 mutants and effects on CD4-HLA class II interaction. Leucocyte Typing V: White Cell Differentiation Antigens. Proceedings of the 5th Int. Workshop and Conference. Boston, USA Nov. 1993. vol. 1: T39.6: 476-478. Ed. Schlossman et al., OUP 1995.
Piccirillo et al., Cutting edge: control of CD8+ T cell activation by CD4+CD25+ immunoregulatory cells. J. Immunol. 2001; 167: 1137-1140.
Pincus et al. Methotrexate as the "anchor drug" for the treatment of early rheumatoid arthritis. (Clin Exp Rheumatol 2003; 21 (Suppl. 31): S179-S185.
Pohlers et al., Differential clinical efficacy of anti-CD4 monoclonal antibodies in rat adjuvant arthritis is paralleled by differential influence on NF-κB binding activity and TNF-α secretion of T cells. Arthritis Res 2002, 4:184-189.

(56) References Cited

OTHER PUBLICATIONS

Pollock et al., Identification of mutant monoclonal antibodies with increase antigen binding, PNAS 1988; 85: 2298-2302.

Pontoux et al., Natural CD4 CD25+ regulatory T cells control the burst of superantigen-induced cytokine production: the role of IL-10, Int. Immunol. 2002; 14(2) :233-239.

Porter et al., Suppressor function of umbilical cord blood-derived CD4+ CD25+ T regulatory cells exposed to Graft-versus-host disease drugs. Cell Therapy and Islet Transplantation. 2006. 83(1); 23-29.

Potter, H., et al., "Enhancer-dependent expression of human K immunoglobulin genes introduced into mouse pre-B lymphocytes by electroporation," Proc. Natl. Acad. Sci. USA 1984;81:7161-7165.

Prevoo, M.L., et al. Modified disease activity scores that include twenty-eight-joint counts. Development and validation in a prospective longitudinal study of patients with rheumatoid arthritis. Arthritis Rheum 38, 44-48 (1995).

Puls, R. L., et al., "Gene transfer and expression of a non-viral polycation-based vector in CD4+ cells," Gene Ther. 1999;6:1774-1778.

Racadot, E., et al., "Treatment of Multiple Sclerosis with Anti-CD4 Monoclonal Antibody," J. Autoimmun. 1993;6:771-786.

Racadot, E., et al, "Immunological follow-up of 17 patients with rheumatoid arthritis treated in vivo with an anti-T CD4+ monoclonal antibody (B-F5)," Clin. Exp, Rheumatol. 1992;10:365-374.

Raganath VK, Khanna D, Paulus HE. ACR remission criteria and response criteria. Clin Exp Rheumatol 24 (Suppl 43), S14-S21, 2006.

Raja et al., CD4 Binding Site Antibodies Inhibit Human Immunodeficiency Virus gp120 Envelope Glycoprotein Interaction with CCR5, J. Virology Jan. 2003; 77, 713-718.

Rau et al., Adalimumab (a fully human anti-tumour necrosis factor α monoclonal antibody) in the treatment of active rheumatoid arthritis: the initial results of five trials. Ann Rheum Dis 2002; 61(Suppl II): ii70-ii73.

Ravetch and Kinet Fc receptors. Annu Rev Immunol 1991. 9: 457.

Raziuddin et al., (1990), Increased circulating HLA-DR+ CD4+ T cells in systemic lupus erythematosus: alterations associated with prednisolone therapy. Scand J Immunol.31, 139-45.

Read et al., Cytotoxic T Lymphocyte—Associated Antigen 4 Plays an Essential Role in the Function of Cd25+Cd4+ Regulatory Cells That Control Intestinal Inflammation. J Exp. Med. 192: 295-302 (2000).

Reich et al., Infliximab induction and maintenance therapy for moderate-to-severe psoriasis: a phase III, multicentre, double-blind trial. The Lancet, vol. 366, Issue 9494, pp. 1367-1374, Oct. 15, 2005.

Riechmann et al., "Re-shaping human antibodies for therapy", Nature (1988); 332: 323-327.

Reinerz and Schlossman, The differentiation and function of human T lymphocytes. Cell 19, 821-827 (1980).

Reinerz et al., Discrete stages of human intrathymic differentiation: Analysis of normal thymocytes and leukemic lymphoblasts of T-cell lineage, PNAS USA 77, 1588-1592 (1980).

Reiter, C., et al., "Treatment of Rheumatoid Arthritis With Monoclonal CD4 Antibody M-T151," Arthritis & Rheumatism 1991;34(5):525-536.

Robinet, E., et al., "Clinical Improvement of a Patient With Severe Psoriasis Following CD4 Antibody Administration Despite a Blocking Antibody-host Response," Eur. J. Dermatol. 1996;6:141-146.

Robinet, E,, et al., "CD4 Monoclonal Antibody Administration in Atopic Dermatitis," J. Amer. Acad. Dermatol. 1997; 36:582-8.

Roitt, A. et al., Extract from Chapter 6, Immunology (2000), Moscow "Mir", pp. 110-111, and English translation of section bridging pp. 110-111.

Reczko, M., et al., "Prediction of hypervariable CDR-H3 loop structures in antibodies," Protein Eng. 1995;8(4):389-395.

Reddy, M.P., et al. Elimination of Fc receptor-dependent effector functions of a modified IgG4 monoclonal antibody to human CD4. J Immunol 164, 1925-1933 (2000).

Rep, M. H. G., et al., "Treatment with Depleting CD4 Monoclonal Antibody Results in a Preferential Loss of Circulating Naïve T Cells but Does Not Affect IFN-y Secreting TH1 Cells in Humans," J. Clin. Invest. 1997;99(9):2225-223.

Rumbach, L., et al., Biological assessment and MRI monitoring of the therapeutic efficacy of a monoclonal anti-T CD4 antibody in multiple sclerosis patients, Multiple Sclerosis 1996;1:207-212.

Rizova et al., The effect of anti-CD4 monoclonal antibody treatment on immunopathological changes in psoriatic skin. J Dermatolog. Sci. 1994; 7: 1-13.

Roberts and Szostak, RNA-peptide fusions for the in vitro selection of peptides and proteins. PNAS (1997) 94(23):12297-302.

Robertson and Ritz (1990), Biology and clinical relevance of human natural killer cells. Blood. 76: 2421-38.

Rudd et al., The CD4 receptor is complexed in detergent lysates to a protein-tyrosine kinase (pp58) from human T-lymphocytes, PNAS USA 85, 5190-5194 (1988).

International Preliminary Report on Patentability for PCT Patent App. No. PCT/EP2009/052810 (Sep. 14, 2010).

Rumbach et al., Essai thérapeutique ouvert d'un anticorps monoclonal anti-T CD4 dans la sclérose en plaques. Rev. Neurol. (Paris) 1994; 150 (6-7): 418-424.

Rump et al., A double blind, placebo-controlled, crossover therapy study with natural human IL-2 (nhuIL-2) in combination with regular intravenous gammaglobulin (IVIG) infusions in 10 patients with common variable immunodeficiency (CVID). Clin. Exp. Immunol. 1997; 110:167-173.

Salfeld. Isotype selection in antibody engineering. Nat Biotechnol 2007. 25: 1369.

Sakaguchi et al., Immunologic tolerance maintained by CD25+ CD4+ regulatory T cells: their common role in controlling autoimmunity, tumor immunity, and transplantation tolerance. Immunol. Rev. 182: 18-32 (2001).

Salmond, R.J., et al. T-cell receptor proximal signaling via the Src-family kinases, Lck and Fyn, influences T-cell activation, differentiation, and tolerance. Immunol Rev 228, 9-22 (2009). Published online Mar. 6, 2009.

Salomon et al., B7/CD28 costimulation is essential for the homeostasis of the CD4+CD25+ immunoregulatory T cells that control autoimmune diabetes. Immunity 12: 431-440 (2000).

Sany J. Immunological treatment of rheumatoid arthritis. Clin Exp. Rheumatol; 8 (Suppl 5): 81-88, 1990.

Sattentau et al., Epitopes of CD4 antigen and HIV infection. Science 1986. 234: 1120.

Sattentau et al., Structural Analysis of the Human Immunodeficiency Virus-Binding Domain of CD4, J. Exp. Med. 170, 1319-1334 (1989).

Setoguchi et al., Repression of the Transcription Factor Th-POK by Runx Complexes in Cytotoxic T Cell Development, Science 319, 822-825 (2008).

Schulze-Koops et al., "Reduction of Th1 Cell Activity in the Peripheral Circulation of Patients with Rheumatoid Arthritis After Treatment with a Non-Depleting Humanized Monoclonal Antibody to CD4," J. Rheumatol. 1998;25(11):2065-2076.

Seddon and Mason, Peripheral Autoantigen induces regulatory T cells that prevent autoimmunity. J. Exp. Med. 189 (5): 877-881, 1999.

Sharma et al., Protein Minimization of the gp120 Binding Region of Human CD4, Biochemistry 44, 16192-16202 (2005).

Shevach, Regulatory T cells in autoimmunity. Annu. Rev. Immunol. 18: 423-449 (2000).
Shevach, CD4+CD25+ suppressor T cells: more questions than answers. Nature Rev. Immunol 2 : 389 (2002).
Stumpp et al., DARPins: a new generation of protein therapeutics. Drug Discov. Today (2008) 13, Nr. 15-16, S. 695-701.
Skerra, Alternative binding proteins: Anticalins—harnessing the structural plasticity of the lipocalin ligand pocket to engineer novel binding activities, FEBS J. 275, 2677-2683 (2008).
Skerra et al. "Engineered protein scaffolds for molecular recognition," J. Mol. Recognit. 2000;13:167-187.

(56) References Cited

OTHER PUBLICATIONS

Simon et al., A Rat CD4 Mutant Containing the gp120-binding Site Mediates Human Immunodeficiency Virus Type 1 Infection, J. Exp. Med. 177, 949-954 (1993).
Smeets et al., Poor expression of T cell derived cytokines and activation and proliferation markers in early rheumatoid synovial tissue. Clin. Immunol. Immunopathol. 88: 84-90, 1998.
Smolen et al., Efficacy and safety of certolizumab pegol plus methotrexate in active rheumatoid arthritis: the RAPID 2 study. A randomised controlled trial. Ann Rheum Dis. Jun. 2009;68(6):797-804. Epub Nov. 17, 2008.
Smolen, J.S., et al. Validity and reliability of the twenty-eight-joint count for the assessment of rheumatoid arthritis activity. Arthritis Rheum 38, 38-43 (1995).
Soundararajan et al., Clinical and immunological effects of a primatized anti CD4 antibody used concomitantly with methotrexate in rheumatoid arthritis. J. Allergy & Clin. Immunol. 1997; 99 No. 1 Pt. 2: S193 No. 777.
Stassen et al., Differential regulatory capacity of CD25+ T regulatory cells and preactivated CD25+ T regulatory cells on development, functional activation, and proliferation of Th2 cells. J. Immunol. (2004); 173(1): 267-74.
Stein et al., Immunohistological analysis of human lymphoma: correlation of histological and immunological categories. Adv Cancer Res. 1984;42:67-147.
Straub et al., Circadian rhythms in rheumatoid arthritis. Athr. & Rheumat. 2007; 56(2): 399-408.
Suri-Payer et al., Pathogenesis of post-thymectomy autoimmune gastritis. Identification of anti-H/K adenosine triphosphatase-reactive T cells. J Immunol. 157: 1799-1805 (1996).
Sun-Payer et al., CD4+CD25+ T cells inhibit both the induction and effector function of autoreactive T cells and represent a unique lineage of immunoregulatory cells. J. Immunol. 160: 1212-1218 (1998).
Suto et al., Role of CD4+CD25+ regulatory T cells in T helper 2 cell-mediated allergic inflammation in the airways. Am. J. Respir. Crit. Care Med. 2001; 164: 680-687.
Suntharalingam et al, Cytokine storm in a phase I trial of the anti-CD28 monoclonal antibody TGN1412. N Engl. J Med. Sep. 7, 2006;355(10):1018-28.
Saitovich, D,, et al., "Kinetics of Induction of Transplantation Tolerance With a Nondepleting Anti-CD4 Monoclonal Antibody and Donor-Specific Transfusion Before Transplantation: A Critical Period of Time is Required for Development of Immunological Unresponsiveness," Transplant. 1996;61(11):1642-1647.
Sakaguchi, S., et al., "Immunologic Self-Tolerance Maintained by Activated T Cells Expressing IL-2 Receptor a-Chains (CD25)," J. Immunol. 1995;155:1151-1164.
Sastry, L., et al., "Cloning of the immunological repertoire in *Escherichia coli* for generation of monoclonal catalytic antibodies: Construction of a heavy chain variable region-specific cDNA library," Proc. Natl. Acad. Sci. USA 1989;86:5728-5732.
Schimke, R. T., "Gene Amplification in Cultured Animal Cells," Cell 1984;37:705-713.
Schulz, Biotest Autumn Conference Presentation for Journalists and Analysts, Frankfurt/Main, Nov. 22, 2004.
Shevach, E. M., "Certified Professionals: CD4+CD25+ Suppressor T Cells," J. Exp. Med. 2001;193(11):F41-F45.
Skov, L, et al., "HuMax-CD4 A Fully Human Monoclonal Anti-CD4 Antibody for the Treatment of Psoriasis Vulgaris," Arch. Dermatol. 2003;139:1433-1439.
Southern, P. J., et al., "Transformation of Mammalian Cells to Antibiotic Resistance with a Bacterial Gene Under Control of the SV40 Early Region Promoter," J. Mol. Appl. Genetics 1982;1:327-341.
Strand et al., Biologic Therapies in rheumatology: lessons learned, future directions. Nat. Rev. Drug Dis. 2007; 6: 75-92.
Subramani, S,, et al., "Expression of the Mouse Dihydrofolate Reductase Complementary Deoxyribonucleic Acid in Simian Virus 40 Vectors," Mol. Cell. Biol. 1981;1(9):854-864.

Sugiyama et al., Dysfunctional blood and target tissue CD4+CD25high regulatory T cells in psoriasis: Mechanism underlying unrestrained pathogenic effector T cell proliferation. J Immunol, 174: 164-173, 2005.
Swierkot et al., Methotrexate in rheumatoid arthritis. Pharmacological Reports 2006; 58: 473-492.
Spalding et al., Cost Effectiveness of Tumor Necrosis Factor-α Inhibition on First Line Agents in Rheumatoid Arthritis. Pharmacoeconomics (2006); 24(12): 1221-1232.
Takai, T. Fc receptors and their role in immune regulation and autoimmunity. J Clin Immunol 25, 1-18 (2005).
Frey et al., The role of regulatory T cells in antigen-induced arthritis: aggravation of arthritis after depletion and amelioration after transfer of CD4+CD25+ T cells. Arthritis Res Ther, 7: R291-R301, 2005.
Gimeno et al., Monitoring the effect of gene silencing by RNA interference in human CD34+ cells injected into newborn RAG2-/-gammac-/—mice: functional inactivation of p53 in developing T cells. Blood 104, 3886-93, 2004.
Goronzy and Weyand, T cell regulation in rheumatoid arthritis. Curr Opin Rheumatol, 16: 212-7, 2004.
Godfrey et al., NKT cells: facts, functions and fallacies, Immunology Today (2000): 21(11): 573-583.
Glamann et al., Characterization of a Macaque Recombinant Monoclonal Antibody That Binds to a CD4-Induced Epitope and Neutralizes Simian Immunodeficiency Virus. J. Virol. (Aug. 2000); 74(15): 7158-63.
Gehan EA, George SL, Estimation of human body surface area from height and weight. Cancer Chemother Rep 1970 54:225-35.
Gellman, Foldamers: A Manifesto. Acc. Chem. Res (1998) 31 (4): 173-180.
Gessner et al., The IgG Fc receptor family. Ann Hematol 1998. 76: 231.
Gorelik and Flavell, Abrogation of TGFα signaling in T cells leads to spontaneous T cell differentiation and autoimmune disease. Immunity 12: 171-181, 2000.
Gottlieb et al., Anti-CD4 monoclonal antibody treatment of moderate to severe psoriasis vulgaris: Results of a pilot, multicenter, multiple-dose, placebo-controlled study. Acad Dermatol 2000; 43: 595-604.
Gottlieb et al., Infliximab induction therapy for patients with severe plaque-type psoriasis: A randomised double-blind, placebo-controlled trial. J. Am Acad. Dermatol. 2004; 51(4):534-542.
Göttlinger et al., Vpu protein of human immunodeficiency virus type 1 enhances the release of capsids produced by gag gene constructs of widely divergent retroviruses, Proc. Natl. Acad. Sci. USA 90, 7381-7385 (1993).
Gillies, S. D,, et al., "A Tissue-specific Transcription Enhancer Element is Located in the Major Intron of a Rearranged Immmunoglobulin Heavy Chain Gene," Cell 1983;33:717-728.
Goetzl, E. J., et al., "Affinity Labeling of a Mouse Myeloina Protein Which Binds Nitrophenyl Ligands, Kinetics of Labeling and Isolation of a Labeled Peptide," Biochemistry 1970;9(5):1267-1278.
Goldberg, D., et al., "Immunological Effects of High Dose Administration of Anti-CD4 Antibody in Rheumatoid Arthritis Patients," J. Autoimmun. 1991;4:617-630.
Gorman, C. M., et al., "The Rous sarcoma virus long terminal repeat is a strong promoter when introduced into a variety of eukaryotic cells by DNA-mediated transfection," Proc. Natl. Acad. Sci, USA 1982;79:6777-6781.
Gorman, S. D., et al., "Reshaping a therapeutic CD4 antibody," Proc. Natl. Acad. Sci. USA 1991;88:4181-4185.
Graham, F. L., et al., "A New Technique for the Assay of Infectivity of Human Adenovirus 5 DNA," Virology 1973;52:456-467.
Gray et al., (1994), The role of transforming growth factor beta in the generation of suppression: an interaction between CD8+ T and NK cells. J Exp Med. 180:1937-42.
Grynkiewicz, G., Poenie, M. & Tsien, R.Y. A new generation of Ca2+ indicators with greatly improved fluorescence properties. J Biol Chem 260, 3440-3450 (1985).
Hori, S., Nomura, T. & Sakaguchi, S. Control of regulatory T cell development by the transcription factor Foxp3. Science 299, 1057-1061 (2003).

(56) References Cited

OTHER PUBLICATIONS

Hammond et al., Antigenic Variation within the CD4 Binding Site of Human Immunodeficiency Virus Type 1 gp120: Effects on Chemokine Receptor Utilization, J. Virology 75, 5593-5603 (2001).
Hara et al., (2001), IL-10 is required for regulatory T cells to mediate tolerance to alloantigens in vivo. J Immunol. 166:3789-96.
Haas et al., Prevalence of newly generated naive regulatory T cells (Treg) is critical for Treg suppressive function and determines Treg dysfunction in multiple sclerosis. J Immunol. Jul. 15, 2007;179(2):1322-30.
Haas et al., Reduced suppressive effect of CD4+CD25high regulatory T cells on the T cell immune response again myelin oligodendrocyte glycoprotein in patients with multiple sclerosis. Eur. J. Immunol. 2005: 35:3343-3352.
Herman et al., Low dose methotrexate induces apoptosis with reactive oxygen species involvement in T lymphocytic cell lines to a greater extent than in monocytic lines. Inflamm Res. Jul. 2005;54(7):273-80.
Haycock G.B., Schwartz G.J.,Wisotsky D.H. Geometric method for measuring body surface area: A height weight formula validated in infants, children and adults. The Journal of Pediatrics 1978 93:1:62-66.
Hepburn et al., Antibody-mediated stripping of CD4 from lymphocyte cell surface in patients with rheumatoid arthritis. Rheumatology Jan. 2003 ;42(1): 54-61.
Herold et al., Anti-CD3 monoclonal antibody in new-onset Type 1 Disease Mellitus. N. Engl. J. Med. 2002; 346(22): 1692-1698.
Herzyk et al., Immunomodulatory Effects of Anti-CD4 Antibody in Host Resistance against Infections and Tumors in Human CD4 Transgenic Mice. Infect Immun. 69(2): 1032-43 (2001).
Hill et al., A Field Guide to Foldamers. Chem. Rev. (2001) 101 (12): 3893-4012.
Horneff, G., et al., "Treatment of Rheumatoid Arthritis With an Anti-CD4 Monoclonal Antibody," Arthritis & Rheumatism 1991;34(2):129-140.
Horwitz et al., (1999), Role of NK cells and TGF-beta in the regulation of T-cell-dependent antibody production in health and autoimmune disease. Microbes Infect. 1:1305-11.
Howie et al., Synthetic peptides representing discontinuous CD4 binding epitopes of HIV-1 gp120 that induce T cell apoptosis and block cell death induced by gp120, FASEB J. 12, 991-998 (1998).
Hoffmann, P., et al., "Donor-type CD4+CD25+ Regulatory T Cells Suppress Lethal Acute Graft-Versus-Host Disease after Allogenic Bone Marrow Transplantation," J. Exp. Med. 2002;196(3):389-399.
Humphreys et al., "F(ab')2 molecules made from *Escherichia coli* produced Fab' with hinge sequences conferring increased serum survival in animal model," J. Immunol. Methods 1998;217:1-10.
Huang et al., Structures of the CCR5 N Terminus and of a Tyrosine-Sulfated Antibody with HIV-1 gp120 and CD4, Science 317, 1930-1934 (2007).
Ivan and Colovai, Human Fc receptors: critical targets in the treatment of autoimmune diseases and transplant rejections. Hum Immunol 2006. 67: 479.
Isaacs et al., A therapeutic human IgG4 monoclonal antibody that depletes target cells in humans, Clin. Exp. Immunol. 1996; 106: 427-433.
Isaacs, J. D., et al., "Humanized Anti-CD4 Monoclonal Antibody Therapy of Autoimmune and Inflammatory Disease," Clin. Exp. Innnunol. 1997;110:158-166.
Jabado et al., CD4 ligands inhibit the formation of multifunctional transduction complexes involved in T cell activation. J Immunol. 158(1): 94-103 (1997).
Jameson et al., Location and Chemical Synthesis of a Binding Site for HIV-1 on the CD4 Protein, Science 240, 1335-1339 (1988).
Jefferis and Lund, Interaction sites on human IgG-Fc for Fcγ: current models. Immunol. Lett. 2002;82: 57.
Jonuleit, H., et al., "Identification and Functional Characterization of Human CD4+CD25+ T Cells with Regulatory Properties Isolated from Peripheral Blood," J. Exp. Med. 2001;193(11):1285-1294.

Jonuleit and Schmitt, The regulatory T cell family: distinct subsets and their interrelations, J. Immunol. 2003; 171: 6323-6327.
Jiang and Chess, An integrated view of suppressor T cell subsets in immunoregulation. J Clin Invest, 114 (9):1198-1208, 2004.
Jiang and Chess, Regulation of Immune responses by T cells. NEJM, 354: 1166-1176, 2006.
Kelchtermans et al., Defective CD4+CD25+ regulatory T cell function in collagen-induced arthritis: an important factor in pathogenesis, counter-regulated by endogenous IFN-•. Arthritis Res Ther, 7: R 402-R415, 2005.
Kabat E. A., "Structure and Heterogeneity of Antibodies," Proc, 10th Congr. Eur. Soc. Haematl., Strasbourg Acta haemat. 1966;36;198-238.
Karim et al. CD25+ CD4+ regulatory T cells generated by exposure to a model protein antigen prevent allograft rejection: antigen-specific reactivation in vivo is critical for bystander regulation. Blood. 2005; 105:4871-4877.
Hoffmann, P., et al., Large-scale in vitro expansion of polyclonal human CD4+ CD25 high regulatory T cells. Blood. 2004; 104(3): 895-903.
Khapalyuk, A.V., "The Genera Questions of Clinical Pharmacology and Demonstrative Medicine", Minsk, Oformlenie, 2003, 90 p., p. 49, pp. 9-11, 25-31.
Klareskog, L., et al., "Therapeutic effect of the combination of etanercept and methotrexate compared with each treatment alone in patients with rheumatoid arthritis: double-blind randomised controlled trial", The Lancet (2004) 363: 675-681.
Ramalingam, T. R., et al., "Ramalingam et al., Exploiting worm and allergy models to understand Th2 cytokine biology," Curr. Opin. Allergy Clin. Immunol. 2005; 5(5): 392-8.
Reich, G., "Pharmaceutical Formulations and Clinical Application", Chapter 10, pp. 239-265, Handbook of Therapeutic Antibodies, Ed. S. Dübel, Wiley-VCH Verlag GmbH & Co. KGaA, Weinheim, 2007.
Wijdenes, J., Slides presented during oral presentation in Heidelberg in Aug. 2003.
Cao et al., CD25brightCD4+ regulatory T cells are enriched in inflamed joints of patients with chronic rheumatic disease. Arthritis Res Ther, 6(4): R335-46, 2004.
Carr et al., Protein and carbohydrate structural analysis of a recombinant soluble CD4 receptor by mass spectrometry, J. Biol. Chem. 264, 21286-21295 (1989).
Carriere et al., "CD4 Masking during Human Immunodeficiency Virus Type 1 Infection, Quantified on Peripheral Blood Lymphocytes, is a Potential Marker of Disease Progression" J. Inf. Dis. 1996;173: 565-73.
Carter et al., Humanization of an anti-p185HER2 antibody for human cancer therapy, Proc. Natl. Acad. Sci. USA 89, 4285-4289 (1992).
Canva-Delcambre, V., et al., "Treatment of severe Crohn's disease with anti-CD4 monoclonal antibody," Aliment. Pharmacol. Ther. 1996;10:721-727.
Chapman et al, "Therapeutic antibody fragments with prolonged in vivo half-lives," Nature Biotechnol. 1999;17:780-783.
Chen et al., Induction of autoantigen-specific Th2 and Tr1 regulatory T cells and modulation of autoimmune diabetes. J. Immunol. Jul. 15, 2003; 171: 733-744.
Chothia, C., et. al, "Conformation of immunoglobulin hypervariable regions," Nature 1989;342:877-883.
Chothia, C., et al,, "Canonical Structures for the Hypervariable Regions of Immunoglobulins," J. Mol. Biol. 1987;196:901-917.
Cohen, J. L., et al, "CD4+CD25+ Immunoregulatory T Cells: New Therapeutics for Graft-Versus-Host Disease," J. Exp, Med. 2002;196(3):401-406.
Coloma, M. J., et al., "Primer Design for the Cloning of Immunoglobulin Heavy-Chain Leader-Variable Regions from Mouse Hybridoma Cells Using the PCR," BioTechniques 1991;11(2):152-156.
Common Terminology Criteria for Adverse Events, Aug. 9, 2006, web page: http://ctep.cancer.gov/protocolDevelopment/electronic_applications/docs/ctcaev3.pdf.

(56) References Cited

OTHER PUBLICATIONS

Chen et al., Regulatory T cell clones induced by oral tolerance: suppression of autoimmune encephalomyelitis. Science 265:1237-1240 (1994).
Choy et al., Monoclonal antibody therapy in rheumatoid arthritis, B. J. Rheumatol. 1998;37: 484-490.
Choy et al., Pharmacokinetic, pharmacodynamic and clinical effects of a humanized IgG1 anti-CD4 monoclonal antibody in the peripheral blood and synovial fluid of rheumatoid arthritis. Rheumatology 39(10): 1139-46 (2000).
Choy et al., Repeat-cycle study of high-dose intravenous 4162W94 anti-CD4 humanized monoclonal antibody in rheumatoid arthritis. A randomized placebo-controlled trial. Rheumatology 41 (10):1142-8 (2002).
Choy et al., "Anti-CD4 monoclonal antibodies in rheumatoid arthritis," Springer Semin. Immunopathol. 1998;20:261-273.
Casset et al., "A peptide mimetic of an anti-CD4 monoclonal antibody by rational design," Biochem Biophys. Res. Comm. 2003;307:198-205.
Choy et al., "Chimaeric anti-CD4 monoclonal antibody cross-linked by monocyte Fcγ receptor mediates apoptosis of human CD4 lymphocytes," Eur. J. Immunol. 1993;23:2676-2681.
Choy, E. H. S., et al., "Percentage of Anti-CD4 Monoclonal Antibody-Coated Lymphocytes in the Rheumatoid Joint is Associated With Clinical Improvement," Arthritis & Rheumatism 1996;39(1):52-56.
Choy et al., Efficacy of a novel PEGylated humanized anti-TNF fragment (CDP870) in patients with rheumatoid arthritis: a phase II double-blinded, randomized, dose-escalating trial. Rheumatology 2002; 41: 1133-1137.
Committee for Medicinal Products for Human Use (CHMP). Guideline on clinical investigation of medicinal products for the treatment of psoriasis. Nov. 18, 2004.
Cronstein, Low-Dose Methotrexate: A Mainstay in the Treatment of Rheumatoid Arthritis (Pharmacol Rev 57:163-172, 2005).
Dantal, J., et al., "Anti-CD4 MAb Therapy in Kidney Transplantation—A Pilot Study in Early Prophylaxis of Rejection," Transplantation 1996;62(10):1502-1506.
Darby, C. R., et al., "Nondepleting Anti-CD4 Antibodies in Transplantation," Transplant, 1994;57(10):1419-1426.
Dieckmann, D., et al, "Ex Vivo Isolation and Characterization of CD4+CD25+ T Cells with Regulatory Properties from Human Blood," J. Exp. Med. 2001;193(11):1303-1310.
Dieckman et al., Activated CD4+CD25+ T cells suppress antigen-specific CD4+ and CD8+ T cells but induce a suppressive phenotype only in CD4+ T cells. Immunology 2005; 115(3): 305-14.
Dowd et al., β-Turn Phe in HIV-1 Env Binding Site of CD4 and CD4 Mimetic Miniprotein Enhances Env Binding Affinity but is Not Required for Activation of Co-Receptor/17b Site, Biochemistry 41, 7038-7046 (2002).
DuBois D; DuBois EF: A formula to estimate the approximate surface area if height and weight be known. Arch Int Med 1916 17:863-71.
Dynabeads Reg CD4+CD25+ T Cell Kit Leaflet (Invitrogen) Copyright 2008.
Dynal Pure and Functional Treg cells: Isolate human and mouse regulatory T cells with Dynabeads (Invitrogen) Copyright 2008.
Earle et al., In vitro expanded human CD4+CD25+ regulatory T cells suppress effector T cell proliferation. Clin. Immunol. (2005) 115: 3-9.
Edmundson A. B., et al., "A Search for Site-Filling Ligands in the Mcg Bence-Jones Diener: Crystal Binding Studies of Fluorescent Compounds," Mol, Immunol, 1984;21(7):561-576.
Ehrenstein et al., Compromised function of regulatory T cells in rheumatoid arthritis and reversal by anti-TNFalpha therapy. J. Exp. Med. 2004; 200(3): 277-285.
Ellis and Mohanakumar, Dissociation of autologous and allogeneic mixed lymphocyte reactivity by using a monoclonal antibody specific for human T helper cells, J. Immunol. 1983, 131(5): 2323-7.
Fehérvari and Sakaguchi, CD4+ Tregs and immune control. J Clin Invest, 114 (9):1209-1217, 2004.
Felgner, P. L. et al., "Lipofection: A highly efficient, lipid-mediated DNA-transfection procedure," Proc. Natl. Acad. Sci. USA 1987;84:7413-7417.
Felson, D.T., et al. The American College of Rheumatology preliminary core set of disease activity measures for rheumatoid arthritis clinical trials. The Committee on Outcome Measures in Rheumatoid Arthritis Clinical Trials. Arthritis Rheum 36, 729-740 (1993).
Fontenot, J.D., Gavin, M.A. & Rudensky, A.Y. Foxp3 programs the development and function of CD4+CD25+ regulatory T cells. Nat Immunol 4, 330-336 (2003).
Fellouse et al., "Synthetic antibodies from a four-amino-acid code: A dominant role for tyrosine in antigen recognition" PNAS Aug. 2004; 101:12467-12472.
Foote, J., et al., "Antibody Framework Residues Affecting the Conformation of the Hypervariable Loops," J. Mol. Biol. 1992;224:487-499.
Fournel et al., "Clonal deletion and clonal anergy mediated by antibodies to the human CD4 protein," pp. 255-264 from Rejection and tolerance: proceedings of the 25th Conference on Transplantation and Clinical Immunology, published by Springer, 1994.
Fleischmann et al., Efficacy and safety of certolizumab pegol monotherapy every 4 weeks in patients with rheumatoid arthritis failing previous disease-modifying antirheumatic therapy: the FAST4WARD study. Ann Rheum Dis. Jun. 2009;68(6):805-11. Epub Nov. 17, 2008.
Fleischmann RM., Safety of biologic therapy in rheumatoid arthritis and other autoimmune diseases: focus on rituximab. Semin Arthritis Rheum. Feb. 2009;38(4):265-80. Epub Mar. 12, 2008.
Furst et al., Adalimumab, a fully human anti tumor necrosis factor-alpha monoclonal antibody, and concomitant standard antirheumatic therapy for the treatment of rheumatoid arthritis: results of STAR (Safety Trial of Adalimumab in Rheumatoid Arthritis). J. Rheumatol. Dec. 2003;30(12):2563-71.
Felson et al., Preliminary definition of improvement in rheumatoid arthritis. Arthritis & Rheumatism, 1995, 38(6), 727-735.
Fitch, T-cell clones and T-cell receptors, Microbiol. Rev. 50, 50-69 (1986).
Froebel et al., 1999. Standardization and quality assurance of lymphocyte proliferation assays for use in the assessment of immune function. J. Immunol. Methods 227: 85-97.
Fuss et al., Nonclassical CD1d-restricted NK T cells that produce IL-13 characterize an atypical Th2 response in ulcerative colitis. J. Clin. Invest. (2004): 113(10): 1490-1497.
Abramowicz et al., Release of tumor necrosis factor, interleukin-2, and gamma-interferon in serum after injection of OKT3 monoclonal antibody in kidney transplant recipients. Transplantation. Apr. 1989;47(4):606-8.
Abramowicz et al, Anaphylactic shock after retreatment with OKT3 monoclonal antibody. N Engl. J Med. Sep. 3, 1992;327(10):736.
Allez and Mayer, Regulatory T cells: peace keepers in the gut, Inflamm. Bowel Dis. (Sep. 2004);10(5):666-76.
American College of Rheumatology Subcommittee on Rheumatoid Arthritis. Guidelines for the management of rheumatoid arthritis: 2002 update. Arthritis Rheum. (2002) 46(2):328-46.
Andersson, J., et al. CD4+ FoxP3+ regulatory T cells confer infectious tolerance in a TGF-beta-dependent manner. J Exp Med 205, 1975-1981 (2008).
Azuma et al., Human CD4+ CD25+ regulatory T cells suppress NKT cell functions. Cancer Research (2003); 63: 4516-4520.
Anderson et al., (1983) Antigens on human plasma cells identified by monoclonal antibodies. J Immunol. 130:1132-8.
Andersson et al., Neutralizing IL-21 and IL-15 inhibits pro-inflammatory cytokine production in rheumatoid arthritis. Scand J Immunol. Jul. 2008:68(1):103-11. Epub May 9, 2008.
Anderson, D., et al. A primatized MAb to human CD4 causes receptor modulation, without marked reduction in CD4+ T cells in chimpanzees: in vitro and in vivo characterization of a MAb (IDEC-CE9.1) to human CD4. Clin Immunol Immunopathol 84, 73-84 (1997).

(56) References Cited

OTHER PUBLICATIONS

Anonymous: T regalizumab (BT-061) shows efficacy in Chronic Plaque Psoriasis. Nov. 24, 2011, pp. 1-2.
Ansel et al., Pharmaceutical Dosage Forms and Drug Delivery Systems, Lippincott Williams & Wilkens, Philadelphia (1999), pp. 126-127.
Apostolou, I., Sarukhan, A., Klein, L. & von Boehmer, H. Origin of regulatory T cells with known specificity for antigen. Nat Immunol 3, 756-763 (2002).
Asano et al., Autoimmune disease as a consequence of developmental abnormality of a T cell subpopulation. J Exp. Med. 184:387-396 (1996).
Ashkenazi et al., Mapping the CD4 binding site for human immunodefincinecy virus by alanine-scanning mutagenesis, PNAS USA 87, 7150-7154 (1990).
Bach, Regulatory T cells under Scrutiny, Nat Rev Immunol. Mar. 3, 2003;3(3):189-98.
Baecher-Allan et al. Functional analysis of highly defined, FACS-isolated populations of human regulatory CD4+CD25+ T cells, Clinical Immunology 115 (2005) 10-18.
Baecher-Allan et al. Inhibition of Human CD4+CD25+high Regulatory T Cell Function, Journal of Immunology (2002), 169:6210-6217.
Baecher-Allan et al., Human Regulatory T cells and their role in autoimmune disease. Immunol. Review 212: 203-216 (2006).
Bachelez et al., Treatment of recalcitrant plaque psoriasis with a humanized non-depleting antibody to CD4. J. Autoimmunity 1998; 11: 53-62.
Bartholomew, M.; et al., "Functional analysis of the effects of a fully humanized anti-CD4 antibody on resting and activated human T cells" Immunology 1995;85(1):41-48.
Baca et al., Antibody Humanization Using Monovalent Phage Display, J. Biol. Chem. 1997;272(16):10678¬ 10684.
Bayrry et al., Rescuing CD4+CD25+ regulatory T-cell functions in rheumatoid arthritis by cytokine-targeted monoclonal antibody therapy. Drug Discov. Today. 2007; 12 (13-14): 548-552.
Balandina, A., Saoudi, A., Dartevelle, P. & Berrih-Aknin, S. Analysis of CD4+CD25+ cell population in the thymus from myasthenia gravis patients. Ann N Y Acad Sci 998, 275-277 (2003).
Becker et al., Functional activation of human CD4+CD25+ regulatory T cells by an anti-CD4 antibody, 9th Basic Science Symposium of the Transplantation Society, Nantes, Abstract No. 24, Jun. 22, 2005.
Becker et al., Induction of suppressive activity in human CD4+CD25+ regulatory T cells by an anti-CD4 antibody, Abstract Marburg 2005.
Becker et al., Funktionelle Aktivierung humaner CD4+CD25+ regulatorischer T-Zellen durch einer anti-CD4 Antikörper (Functional activation of human CD4+CD25+ regulatory T cells by an anti-CD4 antibody), Allergieworkshop 2005, Abstract and Presentation, Johannes Gutenberg Universität Mainz.
Bennett, C.L., et al. The immune dysregulation, polyendocrinopathy, enteropathy, X-linked syndrome (IPEX) is caused by mutations of FOXP3. Nat Genet 27, 20-21 (2001).
Brooks, P. & Hochberg, M. Outcome measures and classification criteria for the rheumatic diseases. A compilation of data from OMERACT (Outcome Measures for Arthritis Clinical Trials), ILAR (International League of Associations for Rheumatology), regional leagues and other groups. Rheumatology (Oxford) 40, 896-906 (2001).
Becker et al., Protection from graft-versus-host disease by HIV-1 envelope protein gp120-mediated activation of human CD4+CD25+ regulatory T cells, Blood 114, 1263-1269 (2009).
Beyersdorf et al., Selective targeting of regulatory T cells with CD28 superagonists allows effective therapy of experimental autoimmune encephalomyelitis. J. Exp. Med. (2005) 202(3): 445-455.
Beste et al., Small antibody-like proteins with prescribed ligand specificities derived from the lipocalin fold, Proc. Natl. Acad. Sci. USA 96, 1898-1903 (1999).
Blaze et al., T cell activation, from atopy to asthma: more a paradox than a paradigm. Allergy Sep. 2003; 58(9): 844.
Biotest AG/Research Update, DGAP publisher, Sep. 8, 2008, pp. 1-2.
Biotest AG, Analystenkonferenz Slides, Sep. 29, 2008.
Beissert et al., Regulatory T cells. J Investigative Dermatology, 126:15-24, 2006.
Becker et al., CD4-mediated activation of human CD4+CD25+ regulatory T cells, Experimental Dermatology 2006, 15, Abstract, p. 204 (33rd Meeting of the Arbeitsgemeinschaft Dermatologische Forschung (ADF), Aachen, Germany, Mar. 23-25, 2006.
Brass et al., Identification of Host Protein Required for HIV Infection Through a Functional Genomics Screen, Science 319, 921-926 (2008).
Bruhns et al., Specificity and affinity of human Fcgamma receptors and their polymorphic variants for human IgG subclasses. Blood 2009. 113: 3716. Epub. Nov. 18, 2008.
Burgdorf et al., Distinct Pathways of Antigen Uptake and Intracellular Routing in CD4 and CD8 T Cell Activation, Science 316, 612-616 (2007).
Bone and Handy, Ab initio studies of internal rotation barriers and vibrational frequencies of (C2H2)2, (CO2)2, and C2H2—CO2, Theor. Chim. Acta 78, 133-163 (1990).
Bonomo et al., Pathogenesis of post-thymectomy autoimmunity. Role of syngeneic MLR-reactive T cells. J. Immunol. 154: 6602-6611 (1995).
Bopp et al., Cyclic adenosine monophosphate is key component of regulatory T cell-mediated suppression. J. Exp. Med. 2007; 204: 1303-1310.
Borselino et al., Expression of ectonucleotidase CD39 by Foxp3+ Treg cells: hydrolysis of extracellular ATP and immune suppression. Blood (2007) 110, 1225-1232.
Boshart, M., et al,,. "A Very Strong Enhancer is Located Upstream of an Immediate Early Gene of Human Cytomegalovirus," Cell 1985;41:521-530.
Briand et al., Application and limitations of the multi antigen peptide (MAP) system in the production and evaluation of anti-peptide and anti-protein antibodies. J Immunol Methods (1992). 156; 2: pp. 255-265.
Camara et al., Human CD4+CD25+ regulatory cells have marked and sustained effects on CD8+ T cell activation. Eur. J. Immunol. 2003; 33: 3473-3483.
Cammarota et al., Identification of a CD4 binding site on the beta2 domain of HLA-DR molecules, Nature 356, 799-801 (1992).
Cao and Leroux-Roels Antigen-specific T cell responses in human peripheral blood leucocyte (hu-PBL)-mouse chimera conditioned with radiation and an antibody directed against the mouse IL-2 receptor beta-chain.Clin. Exp. Immunol. Oct. 2000;122(1): 117-123.
Cao et al., Isolation and functional characterisation of regulatory CD25brightCD4+ T cells from the target organ of patients with rheumatoid arthritis. Eur J Immunol, 33: 215-223, 2003.
Tracey et al., Tumor necrosis factor antagonist mechanisms of action: a comprehensive review. Pharmacol Ther. Feb. 2008;117(2):244-79. Epub Oct. 26, 2007.
Tamm et al., IgG binding sites on human Fcgamma receptors. Intern. Rev. Immunol. 1997; 16: 57-85.
Tak, P. P., et al., "Reduction of Synovial inflammation After Anti-CD4 Monoclonal Antibody Treatment in Early Rheumatoid Arthritis," Arth. Rheum. 1995;38(1):1457-1465.
Takahashi, T., et al., "Immunologic self-tolerance maintained by CD4+CD25+naturally anergic and suppressive T cells: Induction of autoimmune disease by breaking their anergic/suppressive state," Internatl. Immunol. 1998;10 (12):1969-1980.
Takahashi, N., et al., "Structure of Human Immunoglobulin Gamma Genes: Implication for Evolution of a Gene Family," Cell 1982;29(2):671-679.
Taylor, P. A., et al., "The infusion of ex vivo activated and expanded CD4+CD25+ immune regulatory cells inhibits graft-versus-host disease lethality," Blood 2002;99(10):3493-3499.
Thornton, A. M., et al., "Suppressor Effector Function of CD4+CD25+ Immunoregulatory T Cells is Antigen Nonspecific," J. Immunol. 2000;164:183-190.

(56) References Cited

OTHER PUBLICATIONS

Thornton and Shevach, CD4+CD25+ immunoregulatory T cell suppress polyclonal T cell activation in vitro by inhibiting interleukin-2-production, J. Exp. Med. 1998; 188(2): 287-96.
Tifft et al., The Folding and Cell Surface Expression of CD4 Requires Glycosylation, J. Biol. Chem. 267, 3268-3273 (1992).
Traggiai et al., Development of a human adaptive immune system in cord blood cell-transplanted mice. Science 304, 104-7, 2004.
Tribbick et al., Multipin peptide libraries for antibody and receptor epitope screening and characterization. J Immunl. Methods (2002) 267: 27-35).
Trickett et al, T cell stimulation and expansion using anti-CD3/CD28 beads, J. Immunol. Methods, 2003; 275: 251-255.
Tuosto et al., Differential susceptibility of monomeric HIV gp120-mediateds apoptosis in antigen-activated CD4+ T cell populations, Eur. J. Immunol. 25, 2907-2916 (1995).
The Biotest AG Company Presentation dated Jan. 2008, pp. 1-33.
The Merck Manual of Diagnosis and Therapy, Merck Research Laboratories, 1999, pp. 940-941, 949-951 and 968-969.
Valencia, X., et al., TNF downmodulates the function of human CD4(+) CD25 hi T regulatory cells. Blood (2006); 108 (1): 253-261.
Van Der Lubbe, P. A., et al., "Chimeric CD4 Monoclonal Antibody cM-T412 as a Therapeutic Approach to Rheumatoid Arthritis," Arthritis & Rheumatism 1993;36(10):1375-1379.
Verbraecken J, Van de Heyning P, De Backer W, Van Gaal L. Body surface area in normal-weight, overweight, and obese adults. A comparison study. Metabolism. Apr. 2006;55(4):515-24.
Van Amelsfort et al., CD4(+)CD25(+) regulatory T cells in rheumatoid arthritis: differences in the presence, phenotype, and function between peripheral blood and synovial fluid. Arthritis Rheum, 50 (9): 2775-2785, 2004.
Van de Putte et al., Efficacy and safety of the fully human anti-tumour necrosis factor α monoclonal antibody adalimumab (D2E7) in DMARD refractory patients with rheumatoid arthritis: a 12 week, phase II study. Ann Rheum Dis. 2003; 62: 1168-1177.
Van de Putte et al., Efficacy and safety of adalimumab as monotherapy in patients with rheumatoid arthritis for whom previous disease modifying antirheumatic drug treatment has failed. Ann. Rheum. Dis. (2004); 63: 508-516.
Viglietta et al., Loss of functional suppression by CD4+CD25+ regulatory T cell in patients with multiple sclerosis. J Exp Med 199: 971-979, 2004.
Veillette et al., The CD4 and CD8 T cell surface antigens are associated with the internal membrane tyrosine-protein kinase p56lck, Cell 55, 301 (1988).
Vieira, J., et al., "Production of Single-Stranded Plasmid DNA," Methods Enzymol. 1987;153:3-11.
Vogt et al., Construction of an Artificial Receptor Protein ("Anticalin") Based on the Human Apolipoprotein D, ChemBioChem 5, 191-199 (2004).
Voo et al., Identification of IL-17-producing FOXP3+ regulatory T cells in humans, Proc. Natl. Acad. Sci. USA 106, 4793-4798 (2009) Epub Mar. 9, 2009.
Ward, S., et al., "Binding activities of a repertoire of single immunoglobulin variable domains secreted from *Escherichia coli*," Nature 1989;341;544-546.
Wendling, D., et al., "Treatment of Rheumatoid Arthritis with Anti CD4 Monoclonal Antibody. Open Study of 25 Patients with the B-F5 Clone," Clin. Rheumatol. 1992;11(4):542-547.
Wendling, D., et al., "A Randomized, Double Blind, Placebo Controlled Multicenter Trial of Murine Anti-CD4 Monoclonal Antibody Therapy in Rheumatoid Arthritis," J. Rheumatol. 1998;25(8):1457-1461.
Wendling et al., Combination therapy of anti-CD4 and anti-IL6 monoclonal antibodies in a case of severe spondylarthropathy. British J. of Rheumatol. 1996. 35(12): 1330.
Wessels et al., Recent insights in the pharmacological actions of methotrexate in the treatment of rheumatoid arthritis. Rheumatology (Oxford). Mar. 2008;47(3):249-55. Epub Nov. 28, 2007.

Walsh et al., Tregs and transplantation tolerance, J. Clin. Invest. 2004; 114(10): 1398-1403.
Wang et al., Crystal structure of the human CD4 N-terminal two-domain fragment complexed to a class II MHC molecule, Proc. Natl. Acad. Sci. USA 98, 10799-10804 (2001).
Wascher et al., Cell-type specific response of peripheral blood lymphocytes to methotrexate in the treatment of rheumatoid arthritis. Clin Investig. Jul. 1994;72(7):535-40.
Webster's New World Dictionary, Third College Edition, 1988, pp. 1067-1068.
Wendling et al., Therapeutic use of monoclonal anti-CD4 antibody in rheumatoid arthritis. J Rheumatol 18, 325-327, 1991.
Wijdenes et al., Monoclonal antibodies in human organ transplantation and auto-immune disease. Therapie 1992; 47: 283-7.
Wijdenes et al., A new type of monoclonal antibody to CD4 for the therapy of rheumatoid arthritis (RA). Poster, EULAR 2005.
Wijngaarden et al., A shift in the balance of inhibitory and activating Fcgamma receptors on monocytes toward the inhibitory Fcgamma receptor IIb is associated with prevention of monocyte activation in rheumatoid arthritis.Arthritis Rheum. Dec. 2004;50(12):3878-87.
Wijngaarden et al., Down-regulation of activating Fcgamma receptors on monocytes of patients with rheumatoid arthritis upon methotrexate treatment. Rheumatology (Oxford). Jun. 2005;44(6):729-34. Epub Mar. 9, 2005.
Wijngaarden et al., Treatment of rheumatoid arthritis patients with anti-TNF-alpha monoclonal antibody is accompanied by down-regulation of the activating Fcgamma receptor I on monocytes. Clin Exp Rheumatol. Jan.-Feb. 2008;26 (1):89-95.
Willerford et al., Interleukin-2 receptor alpha chain regulates the size and content of the peripheral lymphoid compartment. Immunity 3: 521-530 (1995).
Willkommen and Löwer. Theoretical considerations on viral inactivation or elimination. Brown F (ed): Virological Safety Aspects of Plasma Derivatives Dev Biol Stand. Basel, Karger 1993, vol. 81: 109-116.
Yamaguchi et al., Control of immune responses by antigen-specific regulatory T cells expressing the folate receptor. Immunity. Jul. 2007;27(1):145-59. Epub Jul. 5, 2007.
Yi et al., The effects of antibody treatment on regulatory CD4+CD25+ T cells. Transplant Immunol. 2007; 19(1): 37-44.
Zhou et al., Structural definition of a conserved neutralization epitope on HIV-1 gp120, Nature 445, 732-737 (2007).
Zhu, Z., et al., "Inhibition of human leukemia in an animal model with human antibodies directed against vascular endothelial growth factor 2. Correlation between antibody affinity and biological activity," Leukemia 2003;17:604¬611.
Search Report from GB Patent App. No. 0706965.1 (Jul. 9, 2007).
International Search Report from PCT Patent App. No. PCT/EP2009/052810 (Jul. 13, 2009).
Anderson, A. E., et al., "Tregs and Rheumatoid Arthritis," ACTA Rheumatol. Port. 2008;33:17-33.
Biotest Half-Year Report of Jun. 30, 2008, pp. 1-16.
Cools, N., et al., "Regulatory T Cells and Human Disease," Clinical and Developmental Immunology, vol. 2007, pp. 1-11.
Dimasi, J. A., et al., "The price of innovation: new estimates of drug development costs," J. Health Economics 2003;22:151-185.
Feldmann, M., et al., "Role of cytokines in rheumatoid arthritis: an education in pathophysiology and therapeutics," Immunol. Rev. 2008;223:7-19.
Korn, T., et al., "Dynamics of antigen-specific regulatory T-cells in the context of autoimmunity," Seminars in Immunol. 2007;19:272-278.
Non-Final Office Action for co-pending U.S. Appl. No. 12/880,837 (Dec. 2, 2014).
Non-Final Office Action for co-pending U.S. Appl. No. 13/074,357 (Dec. 8, 2014).
Non-Final Office Action for co-pending U.S. Appl. No. 12/880,623 (Nov. 28, 2014).
Pincus, T., "Quantitative measure for assessing rheumatoid arthritis in clinical trials and clinical care," Best Practice & Research Clinical Rheumatology 2003;17(5):753-781.
Moebius et al., "The Human Immunodeficiency Virus gp120 Binding Site on CD4: Delineation by Quantitative Equilibrium and

(56) References Cited

OTHER PUBLICATIONS

Kinetic Binding Studies of Mutants in Conjunction with a High-Resolution CD4 Atomic Structure", J. Exp. Med. 176, 507-517, 1992.

Ohlson et al., "Detection and characterization of weak affinity antibody antigen recognition with biomolecular interaction analysis", J. Mol. Recognit. May-Jun. 1997; 10(3): 135-8, 1997.

Pakula et al., "Genetic analysis of protein stability and function", Annu. Rev. Genet., 1989; 23, 289-310, p. 289 & 306, 1989.

Salemi et al., "HIVgp120 activates autoreactive CD4-specific T cell responses by unveiling of hidden CD4 peptides during processing", Journal of Experimental Medicine, 1995, vol. 181 pp. 2253-2257, 1995.

Wang, W., "Oral protein drug delivery", Journal of Drug Targeting, 1996, vol. 4, No. 4, pp. 195-232, 1996.

Biotest AG Press release—Biotest Phase IIb study of Tregalizumab (BT-061) in moderate to severe rheumatoide Arthritis did not meet the primary endpoint—potential one time effect of up to—EUR 30 million, Apr. 24, 2015, pp. 1-3, 2015.

Biotest half-year report of Aug. 11, 2015—Biotest increase revenues in first half year 2015 by 8.9%, pp. 1-3, 2015.

Severin et al., "Biochemistry", textbook M.: Meditsina, 2000, 168 p.; p. 7 in Russian with English translation, 2009.

Tarantul, V. Z., Explanatory dictionary of biotechnology. Russian-English, M. Yaziki slavyanskih kultur, 2009, p. 510, 2009.

Final Office Action for co-pending U.S. Appl. No. 12/880,837 (Jun. 10, 2015).

Final Office Action for co-pending U.S. Appl. No. 13/074,357 (Sep. 17, 2015).

Tamura, M., et al., "Structural Correlates of an Anticarcinoma Antibody: Identification of Specificity-Determining Residues (SDRs) and Development of a Minimally Immunogenic Antibody Variant by Retention of SDRs Only," J. Immunol. 2000;164(3):1432-1441.

Wailoo, A., et al., Agency for Healthcare Research and Quality, 540 Gaither Road, Rockville, MD 20850, Oct. 12, 2006, pp. 1-74.

Office Action from U.S. Appl. No. 13/074,357 (Mar. 30, 2016).

Dore, J.-M., et al., "Identification and location on syndecan-1 core protein of the epitopes of B-B2 and B-B4 monoclonal antibodies," FEBS Lett. 1998;426:67-70.

Hartl, D., et al., "Quantitative and functional impairment of pulmonary CD4+CD25hi regulatory T cells in pediatric asthma," J. Allergy Clin. Immunol. 2007;119:1258-1266.

Van Amelsfort, J. M. R., et al., "Proinflammatory Mediator-Induced Reversal of CD4+, CD25+ Regulatory T Cell-Mediated Suppression in Rheumatoid Arthritis," Arthritis & Rheumatism, Mar. 2007, vol. 56, No. 3, pp. 132-742.

Williams, R. O., et al., "Synergy between anti-CD4 and anti-tumor necrosis factor in the amelioration of established collagen-induced arthritis," Proc. Natl. Acad. Sci. USA 1994;91:2762-2766.

Freidlin, I. S., "Regulatory T Cells: Origin and Function," Med. Immunol. 2005;7(4):347-354, with English language translation thereof.

Moore, J. P., et al., "A Monoclonal Antibody to CD4 Domain 2 Blocks Soluble CD4-Induced Conformational Changes in the Envelope Glycoproteins of Human Immunodeficiency Virus Type 1 (HIV-1) and HIV-1 Infection of CD4+ Cells," J. Virol. 1992;66(8):4784-4793.

Krueger, G. G., et al., "A randomized, double-blind, placebo-controlled phase III study evaluating efficacy and tolerability of 2 courses of alefacept in patients with chronic plaque psoriasis," J. Am. Acad. Dermatol. 2002;47:821-833.

Office Action from U.S. Appl. No. 12/880,623 (Feb. 8, 2016).

Makrides, S. C., "Components of Vectors for Gene Trasfer and Expression in Mammalian Cells," Protein Expression and Purification 1999;17:183-202.

Non-Final Office Action from co-pending U.S. Appl. No. 14/176,485 (Dec. 9, 2016).

\* cited by examiner mB-F5 V$_H$

CAG GAA TAC CTT GTG GAG ACC GGG GGA GGC TTG GTG AGG CCT GGA AAT TCT CTG AAA

CTC TCC TGT GTC ACC TCG GGT TTC AGT TTC AGT GAC TGC GGA ATG TAC TGG CTT CGC

CAG CCT CCA GGG AAG GGG CTG GAG TGG ATT GGT GTG ATT TCA GTC AAA TCT GAG AAT

TAT GGA GCA AAT TAT GCA GAG TCT GTG AGG GGC AGA TTC ACT ATT TCA AGA GAT GAT

TCA AAA AGC AGT GTC TAT CTG CAG ATG AGC AGA TTG AGA GAG GAA GAC ACT GCC ACT

TAT TAT TGT AGT GCC TCC TAT TAT AGG TAC GAC GTG GGG GCC TGG TTT GCT TAC TGG

GGC CAA GGG ACT CTG GTC ACT GTC TCT GCA

FIGURE 3 mB-F5 V$_K$

GAC ATT GTG CTG ACA CAG TCT CCT TCT TCC TTA GTT GTA TCT CTG GGG CAG AGG GCC

ACC ATC TCA TGC AGG GCC AGC AAA AGT GTC AGT ACA TCT GGC TAC AGT TAT ATA TAT

TGG TAC CAA CAG ATC CCA GGA CAG CCA CCC AAA CTC CTC ATC TAT CTT GCA TCC ATC

CTA GAA TCT GGG GTC CCT GGC AGG TTC AGT GGC AGT GGG TCT GGG ACA GAC TTC ACC

CTC AAC ATC CAT CCT GTG GAG GAG GAC GAT GCT GCA ACC TAT TAC TGT CAG CAC AGT

AGG GAA CTT CCG TGG ACG TTC GGT GGA GGC ACC AAG CTG GAG ATC AAA CGG GCT GAT

GCT GCA CCA ACT GTA TCC ATC TTC CCA CCA TCC AGT GAG CA

FIGURE 4

```
GA GGA GCT CCA GAC AAT GTC TGT CTC CTT CCT CAT CTT CCT GCC CGT GCT GGG CCT

CCC ATG GGG TCA GTG TCA GGG AGA TGC CGT ATT CAC AGC AGC ATT CAC AGA CTG AGG

GGT GTT TCA CTT TGC TGT TTC CTT TTG TCT CCA GGT GTC CTG TCA GAG GAA CAG CTT
                                                            E   E   Q   L
GTG GAG TCT GGG GGA GGC TTG GTG AAA CCC GGA GGT TCT CTG AGG CTC TCC TGT GCA
 V   E   S   G   G   G   L   V   K   P   G   G   S   L   R   L   S   C   A

GCC TCG GGT TTC AGT TTC AGT GAC TGC CGG ATG TAC TGG GTT CGC CAG GCT CCA GGG
 A   S   G   F   S   F   S   D   C   R   M   Y   W   V   R   Q   A   P   G

AAG GGG CTG GAG TGG ATT GGT GTG ATT TCA GTC AAA TCT GAG AAT TAT GGA GCA AAT
 K   G   L   E   W   I   G   V   I   S   V   K   S   E   N   Y   G   A   N

TAT GCA GAG TCT GTG AGG GGC AGA TTC ACT ATT TCA AGA GAT GAT TCA AAA AAC ACG
 Y   A   E   S   V   R   G   R   F   T   I   S   R   D   D   S   K   N   T

GTC TAT CTG CAG ATG AAC AGC TTG AAG ACC GAA GAC ACT GCC GTT TAT TAT TGT AGT
 V   Y   L   Q   M   N   S   L   K   T   E   D   T   A   V   Y   Y   C   S

GCC TCC TAT TAT AGG TAC GAC GTG GGG GCC TGG TTT GCT TAC TGG GGC CAA GGG ACT
 A   S   Y   Y   R   Y   D   V   G   A   W   F   A   Y   W   G   Q   G   T

CTG GTC ACT GTC TCT TCA GGT AAG AAT GGC CAA GCT TG
 L   V   T   V   S   S
```

FIGURE 5

```
GGA GGA TCC AAT TAT CTG CTG ACT TAT AAT ACT ACT AGA AAG CAA ATT TAA ATG ACA

TAT TTC AAT TAT ATC TGA GAC AGC GTG TAT AAG TTT ATG TAT AAT CAT TGT CCA TTC

CTG ACT ACA GGT GCC TAC GGG GAC ATC GTG ATG ACC CAG TCT CCA GAC TCC CTG GCT
                                 D   I   V   M   T   Q   S   P   D   S   L   A

GTG TCT CTG GGC GAG AGG GCC ACC ATC AAC TGC AGG GCC AGC AAA AGT GTC AGT ACA
 V   S   L   G   E   R   A   T   I   N   C   R   A   S   K   S   V   S   T

TCT GGC TAC AGT TAT ATA TAT TGG TAC CAG CAG AAA CCA GGA CAG CCT CCT AAG CTG
 S   G   Y   S   Y   I   Y   W   Y   Q   Q   K   P   G   Q   P   P   K   L

CTC ATT TAC CTT GCA TCC ATC CTA GAA TCT GGG GTC CCT GAC CGA TTC AGT GGC AGC
 L   I   Y   L   A   S   I   L   E   S   G   V   P   D   R   F   S   G   S

GGG TCT GGG ACA GAT TTC ACT CTC ACC ATC AGC AGC CTG CAG GCT GAA GAT GTG GCA
 G   S   G   T   D   F   T   L   T   I   S   S   L   Q   A   E   D   V   A

GTT TAT TAC TGT CAG CAC AGT AGG GAA CTT CCG TGG ACG TTC GGC CAA GGG ACC AAG
 V   Y   Y   C   Q   H   S   R   E   L   P   W   T   F   G   Q   G   T   K

GTG GAA ATC AAA CGT GAG TAG AAT TTA AAT TTT AAG CTT CTT
 V   E   I   K
```

FIGURE 6

```
           FR1                    CDR1              FR2
           1            2          3                 4
       12345678901234567890123 456777778901234 567890123456789
                                    ABCD mB-F5    DIVLTQSPSSLVVSLGQRATISC RASKSVSTSGYSYIY WYQQIPGQPPKLLIY
hB-F5L4M DIVMTQSPDSLAVSLGERATINC RASKSVSTSGYSYIY WYQQKPGQPPKLLIY
hB-F5L4L ---L------------------- --------------- -H------------
FK-001   DIVMTQSPDSLAVSLGERATINC                 WYQQKPGQPPKLLIY

CDR2              FR3
         5         6        7         8
       0123456 789012345678901234567890012345678 mB-F5    LASILES GVPCRFSGSGSGTDFTLNIHPVEEEDAATYYC
hB-F5L4M LASILES GVPDRFSGSGSGTDFTLTISSLQAEDVAVYYC
hB-F5L4L ------- ---------------------------------
FK-001           GVPDRFSGSGSGTDFTLTISSLQAEDVAVYYC

CDR3       FR4
         9          10
       901234567 8901234567 mB-F5    QHSRELPWT FGGGTKLEIK
hB-F5L4M QHSRELPWT FGQGTKVEIK
hB-F5L4L --------- F---------
FK-001             FGQGTKVEIK
```

FIG. 20

```
                    FR1                        CDR1      FR2
           1             2             3         
           1234567890123456789012345678901    12345    67890123456789 mB-F5      QEYLVETGGGLVRPGNSLKLSCVTSGFSFS    DCRMY    WLRQPPGKGLEWIG
hB-F5H37V  EVQLVESGGGLVKPGGSLRLSCAASGFSFS    DCRMY    WVRQAPGKGLEWIG
hB-F5H37L  -E------------------------------  -----    -L------------
M26        EVQLVESGGGLVKPGGSLRLSCAASGFTFS             WVRQAPGKGLEWVG
            *                        *                             *

CDR2                                      FR3
           5             6             7             8             9
           0122223456789012345    678901234567890122223456789012234
              ABC                                    ABC
mB-F5      VISVKSENYGANYAESVRG    RFTISRDDSKSSVYLQMSRLREEDTATYYCSA
hB-F5H37V  VISVKSENYGANYAESVRG    RFTISRDDSKNTVYLQMNSLKTEDTAVYYCSA
hB-F5H37L  -------------------    --------------------------------
M26                               RFTISRDDSKNTLYLQMNSLKTEDTAVYYCTT
                                          *                      **

CDR3            FR4
           10             11
           5678900000012  34567890123
              ABCDE
mB-F5      SYYRYDVGAWFAY  WGQGTLVTVSA
hB-F5H37V  SYYRYDVGAWFAY  WGQGTLVTVSS
hB-F5H37L  -------------  -----------
M26                       WGQGTLVTVSS
```

FIG. 21

METHOD FOR TREATING PSORIASIS

This application is a continuation under 35 U.S.C. §120 of PCT Patent Application No. PCT/EP2009/052810, filed on Mar. 10, 2009, which claims priority under 35 U.S.C. §119 to Great Britain Patent Application Nos. 0804687.2, filed on Mar. 13, 2008, and 0817809.7, filed on Sep. 29, 2008, which are incorporated in their entireties by reference. The Sequence Listing in electronic format filed herewith is also hereby incorporated by reference in its entirety (File Name: 2010-09-13T_060-010_Seq_List; File Size: 13 KB; Date Created: Sep. 13, 2010).

BACKGROUND OF THE INVENTION

The present invention is concerned with treatment of autoimmune diseases. The invention involves an agent such as a humanised monoclonal antibody with a long-term effect that may be administered to patients in therapy less frequently than previously described. It is particularly beneficial for patients having diseases or characteristics that cannot be removed in the short term, or require indefinite treatment for effective relief from symptoms. The invention envisages uses and methods of treatment employing the compositions and medicaments comprising the agent.

Autoimmunity is the failure of an organism to recognise its own constituent parts (down to sub-molecular levels) as "self", which results in an immune response against its own cells and tissues. Any disease that results from such an aberrant immune response is termed an autoimmune disease. Autoimmune diseases include multiple sclerosis (MS), rheumatoid arthritis (RA), psoriasis, psoriatic arthritis, colitis ulcerosa, Crohn's disease, myasthenia gravis (MG), autoimmune polyglandular syndrome type II (APS-II), Hashimoto's thyreoiditis (HT), type-1 diabetes (T1D), systemic lupus erythematosus (SLE) and autoimmune lymphoproliferative syndrome (ALS).

Autoimmune disease occurs when T cells recognise and react to 'self' molecules, that is, molecules produced by the cells of the host. Activation of 'autoreactive' T cells by presentation of autoantigens processed by antigen presenting cells (APC) leads to their clonal expansion and migration to the specific tissues, where they induce inflammation and tissue destruction.

Normally, T cells are tolerant with regard to autologous tissue and only react on presentation of heterologous structures. Central tolerance and peripheral tolerance comprise the two mechanisms by which the immune system hinders autoreactive T cells from inducing their deleterious functions. Central tolerance is mediated through negative selection. This process entails the elimination, through clonal deletion of autoreactive T cells, during ontogenic development in the thymus.

Peripheral tolerance is the backup available if central tolerance fails and autoreactive cells escape the thymus. This mechanism of tolerance occurs continuously throughout life, keeping autoreactive cells in check through immune ignorance (anergy), peripheral deletion and/or active suppression.

T regulatory cells (Tregs, formerly also designated "suppressor cells") as part of active suppression maintain peripheral tolerance and regulate autoimmunity (Suri-Payer et al., J. Immunol. 157: 1799-1805 (1996); Asano et al., J. Exp. Med. 184:387-396 (1996); Bonomo et al., J. Immunol. 154: 6602-6611 (1995); Willerford et al., Immunity 3: 521-530 (1995); Takahashi et al., Int. Immunol. 10: 1969-1980 (1998); Salomon et al., Immunity 12: 431-440 (2000); Read et al., J. Exp. Med. 192: 295-302 (2000). In general, regulatory T cells inhibit the activation and/or function of T helper type 1 (TH1) and TH2 effector cells. Dysregulation in Treg cell frequency or functioning can lead to debilitating autoimmune diseases (Baecher-Allan et al., Immunol. Review 212: 203-216 (2006); Shevach, Annu. Rev. Immunol. 18: 423-449 (2000); Salomon et al., Immunity 12: 431-440 (2000); Sakaguchi et al., Immunol. Rev. 182: 18-32 (2001)).

Several subsets of regulatory T cells have been characterized. The family of Tregs consists of two key subsets: naturally arising e.g. $CD4^+CD25^+$ Tregs and peripherally induced, Tr1 and Th3 Tregs. Furthermore NKTregs and $CD8^+$ Tregs have been described in humans and rodents (Fehervari et al., J. Clin. Investigation 114: 1209-1217 (2004)).

Thymus-derived Treg cells (naturally occurring $CD4^+CD25^+$Treg) are the main regulatory cells involved regulating autoimmunity or pathogenic immune responses.

i) they are $CD4^+$ T cells and constitute 5-10% of peripheral $CD4^+$ T cells ii) they mature in the thymus iii) they are generally characterized by the combined expression of the IL-2 receptor (CD25), the low molecular isoform of the CD45 molecule, CD152 (CTLA-4), and the transcription factor FoxP3.

The role of Tregs is exemplified best by experiments involving reconstitution of immunodeficient nude mice with $CD4^+$ cells that were depleted of $CD25^+$ cells. $CD4^+CD25^-$ reconstituted nude mice develop various organ-specific autoimmune diseases, such as gastritis, oophoritis, orchitis, and thyreoiditis (Suri-Payer et al.; J. Immunol. 160: 1212-1218 (1998)).

Inclusion of the $CD4^+CD25^+$ subset into reconstitution experiments with nude mice prevents the onset of these diseases (Sakaguchi et al., J. Immunol. 155: 1151-1164 (1995)). The protective value of $CD4^+CD25^+$ cells against organ-specific autoimmunity has also been shown in several other models of autoimmunity (e.g. autoimmune gastritis, prostatitis, oophoritis, glomerulonephritis, epidimytis and thyreoiditis) caused by neonatal thymectomy performed 3 days after birth (d3Tx) or inflammatory bowel disease caused by reconstitution of SCID mice with CD45RBhigh, $CD4^+CD25^-$ T cells. Administration of anti-CD25 antibody in vivo in mice also induces organ-localised autoimmune disease.

The discovery of the importance of the transcriptional regulator FoxP3 in mouse $CD4^+CD25^+$ T regulatory cell function and the previous observations that patients with IPEX syndrome (immune dysregulation, polyendocrinopathy, enteropathy, and X-linked inheritance), a severe inflammatory disease similar to that seen in mice deficient in $CD4^+CD25^+$ regulatory cells (scurfy syndrome), have mutations in FoxP3, provided a direct correlation between an autoimmune animal model, mouse regulatory T cells, and a human autoimmune disease (Sakaguchi et al., J. Immunol. 155: 1151-1164 (1995)).

The pharmaceutical mechanism of regulatory T cells is not fully clear. $CD4^+CD25^+$ Tregs inhibit polyclonal and antigen-specific T cell activation. The suppression is mediated by a cell contact-dependent mechanism that requires activation of $CD4^+CD25^+$ Tregs via the TCR but Tregs do not show a proliferative response upon TCR activation or stimulation with mitogenic antibodies (anergic) (Shevach, Nature Rev. Immunol 2: 389 (2002). Once stimulated, they are competent to suppress in an antigen-independent manner the response of CD4+ T cells and CD8+ T cells as well as inhibit B-cell activation and their clonal expansion.

There are additional data indicating that suppressor activity of CD4$^+$CD25$^+$ Tregs partially also relies on anti-inflammatory cytokines like TGF-β (Kingsley et al., J. Immunol. 168: 1080 (2002); Nakamura et al., J. Exp. Med. 194: 629-644 (2001)). The functional significance of TGF-β secretion is furthermore supported by the findings that TGF-β-deficient mice develop autoimmune disease and that administration of neutralizing antibodies to TGF-β abrogates in vivo the prevention of autoimmunity or tolerance-inducing activity of CD4$^+$ T cells in some models.

Within the CD4$^+$ T cell subset at least 2 more different types of cells with suppressive function may exist, which are induced after exposure to specific, exogenous antigen (called 'adaptive or inducible regulatory T cells'): Type 1 T regulatory (Tr1) cells and Th3 cells. These cell types appear to be distinguishable from CD4$^+$CD25$^+$ Tregs based on their cytokine production profiles. However, the relationship between these different types is unclear and the modes of action are overlapping.

Tr1 cells were induced by repetitive stimulation of TCR in the presence of IL-10 and were shown to mainly down-regulate immune responses via the production of high levels of IL-10 together with moderate amounts of TGF-β (Chen et al., J. Immunol. 171: 733-744 (2003)).

Th3 cells (identified in a model of EAE after oral delivery of antigen) produce high amounts of TGF-β and variable amounts of IL-4 and IL-10. IL-4, itself, was shown to be a key factor for the differentiation of Th3 cells, in contrast to Tr1 cells that are differentiated with IL-10 (Chen et al., Science 265:1237-1240 (1994)).

Suppression of T cell function by using immunosuppressive drugs is a principal therapeutic strategy that has been used successfully to treat autoimmune diseases. However these drugs induce a general immunosuppression due to their poor selectivity, resulting in inhibition of not only the harmful functions of the immune system, but also useful ones. As a consequence, several risks like infection, cancer and drug toxicity may occur.

Agents interfering with T cell function are therapeutic mainstays for various autoimmune diseases.

The approach of using agents aiming at the activation of regulatory T cells for the therapy of autoimmune diseases have been up to now proven to be extremely difficult. Activation of Tregs via the TCR using the agonistic anti-CD3 antibody OKT-3 (Abramowicz et al, N Engl. J. Med. 1992 Sep. 3; 327(10):736) or via the co-stimulatory molecule CD28 using the superagonistic anti-CD28 antibody TGN 1412 leads to complete depletion of the regulatory T cell population as well as other conventional T cells and the systemic induction and release of excessive amounts of pro-inflammatory cytokines including IFN-γ, TNF-α, IL-1 and IL-2, resulting in a clinically apparent cytokine release syndrome (CRS) in humans (Suntharalingam et al, N Engl. J. Med. 2006 Sep. 7; 355(10):1018-28).

After the first two to three injections of 5 mg of the monoclonal antibody OKT3 most patients develop a cytokine release syndrome with high levels of tumour necrosis factor-alpha, interleukin-2, and gamma-interferon appearing within 1-2 hrs in the circulation of kidney transplant recipients. (Abramowicz et al, Transplantation. 1989 April; 47(4):606-8). This results in a narrow therapeutic window which limits the usefulness of this antibody in the treatment of autoimmune disease.

Treatment with a total dose of 5-10 mg of TGN1412 (0.1 mg anti-CD28 per kilogram of body weight) lead to a systemic inflammatory response with multiorgan failure within 90 minutes after receiving a single intravenous dose of the TGN 1412 (Suntharalingam et al, N Engl. J. Med. 2006 Sep. 7; 355(10):1018-28).

It is generally agreed that CD4 T cells play a major part in initiating and maintaining autoimmunity. Accordingly, it has been proposed to use mAbs against CD4 T cells surface molecules, and in particular anti-CD4 mAbs, as immunosuppressive agents. Although numerous clinical studies confirmed the potential interest of this approach, they also raised several issues to be addressed in order to make anti-CD4 mAbs more suitable for use in routine clinical practice.

Several different mechanisms of action for CD4 mAbs have been proposed including: (1) antagonism of CD4-MHC II interactions resulting in inhibition of T cell activation, (2) CD4 receptor modulation as determined by a decrease in cell surface expression of CD4, (3) partial signaling through the CD4 receptor in the absence of T cell receptor cross-linking which can suppress subsequent T cell activation and trigger CD4 T cell apoptotic death, (4) Fc-mediated complement-dependent cytotoxicity (CDC) or antibody-dependent cellular cytotoxicity (ADCC) leading to CD4 T cell depletion, and (5) stimulation of regulatory T cells.

Fc-mediated complement-dependent cytotoxicity (CDC) or antibody-dependent cellular cytotoxicity (ADCC) leading to CD4 T cell depletion is the main observed mechanism and is especially demonstrated for antibodies of the IgG1 subclass. Only a few CD4 antibodies have been attributed to the other mechanisms like TRX-1, TNX-355, IDEC-151, OKTcdr4A with only TRX-1 being an IgG1 (Schulze-Koops et al., J Rheumatol. 25(11): 2065-76 (1998); Mason et al., J Rheumatol. 29(2): 220-9 (2002); Choy et al., Rheumatology 39(10): 1139-46 (2000); Herzyk et al., Infect Immun. 69(2): 1032-43 (2001); Kon et al., Eur Respir J. 18(1): 45-52 (2001); Mourad et al., Transplantation 65(5): 632-41 (1998); Skov et al., Arch Dermatol. 139(11): 1433-9 (2003); Jabado et al., J. Immunol. 158(1): 94-103 (1997)).

Dose-dependent depletion of CD4$^+$ T cells at "high" doses (multiple cycles with dosages >100 mg) and transient sequestration (short-lived depletion) at "lower" doses (multiple cycles with dosages >10 mg), is observed with several CD4 antibodies (Mason et al., J. Rheumatol. 29 (2): 220-229 (2002); Kon et al., Eur. Respir J. 18(1):45-52 (2001)) and HuMax-CD4 (Skov et al., Arch Dermatol. 139(11): 1433-1439 (2003), Choy et al., Rheumatology 41 (10):1142-8 (2002)). Despite of their depletional activity, mAbs to CD4 failed to provide clinical benefit and consistent efficacy in autoimmune diseases investigated e.g. rheumatoid arthritis (Strand et al., Nature Reviews 6: 75-92 (2007)). Furthermore depletion of CD4$^+$ T cells is generally considered as scenario, which might cause a severe immunosuppression.

The B-F5 antibody (murine IgG1 anti-human CD4) was tested in different autoimmune diseases.

A small number of patients with severe psoriasis have been treated with the murine B-F5 antibody and some positive effects were described (Robinet et al., Eur J Dermatol 1996: 6: 141-6, and Robinet et al., J Am Acad Dermatol 1997; 36: 582-8).

In rheumatoid arthritis patients, the results observed in a placebo controlled trial with a daily dose of B-F5 did not indicate a significant improvement (Wendling et al. J Rheumatol; 25 (8):1457-61, 1998).

In multiple sclerosis (MS) patients, some positive effects were observed after a 10 days treatment in patients with relapsing-remitting forms, some of who were still relapse-free at the 6th month post-therapy (Racadot et al., J Autoimmun, 6(6):771-86, 1993). Similar effects were observed by Rumbach et al. (Mutt Scler; 1(4):207-12, 1996).

In severe Crohn's disease, no significant improvement was observed in patients receiving B-F5 for 7 consecutive days or (Canva-Delcambre et al., Aliment Pharmacol Ther 10(5):721-7, 1996).

In prevention of allograft rejection, it was reported that B-F5 bioavailability was not sufficient to allow its use for prophylaxis of allograft rejection (Dantal et al. Transplantation, 27; 62(10):1502-6, 1996).

It appears from the above that a first issue to be solved is the need for using longer term doses of mAb to obtain a clinical improvement. In general, the long term use of disease modifying therapeutics results in increased numbers of adverse events or loss of clinical effects, necessitating a dose increase ("dose-creep") to maintain response (Strand et al., Nature Reviews Drug Discovery 6: 75-92, (2007)) due to immunogenicity. The lesser and/or the less frequent disease modifying therapeutics have to be administered the lower those adverse events will be, plus there is an immediate beneficial effect for the patients requiring lower and/or less doses of the therapeutics.

Another drawback of therapy with monoclonal antibodies in humans is that these antibodies are generally obtained from mouse cells, and provoke anti-mouse responses in the human recipients. This not only results in a lower efficiency of the treatment and even more of any future treatment with mouse monoclonal antibodies, but also in an increased risk of anaphylaxis.

This drawback can, in principle, be avoided by the use of humanized antibodies, obtained by grafting the complementarity-determining regions (CDRs) of a mouse monoclonal antibody, which determine the antigen-binding specificity, onto the framework regions (FRs) of a human immunoglobulin molecule. The aim of humanization is to obtain a recombinant antibody having the same antigen-binding properties as the mouse monoclonal antibody from which the CDR sequences were derived, and far less immunogenic in humans.

In some cases, substituting CDRs from the mouse antibody for the human CDRs in human frameworks is sufficient to transfer the antigen-binding properties (including not only the specificity, but also the affinity for antigen). However, in many antibodies, some FR residues are important for antigen binding, because they directly contact the antigen in the antibody-antigen complex, or because they influence the conformation of CDRs and thus their antigen binding performance.

Thus, in most cases it is also necessary to substitute one or several framework residues from the mouse antibody for the human corresponding FR residues. Since the number of substituted residues must be as small as possible in order to prevent anti-mouse reactions, the issue is to determine which amino acid residue(s) are critical for retaining the antigen-binding properties. Various methods have been proposed for predicting the more appropriate sites for substitution. Although they provide general principles that may be of some help in the first steps of humanization, the final result varies from an antibody to another. Thus, for a given antibody, it is very difficult to foretell which substitutions will provide the desired result.

Previously the humanization of mouse B-F5 has been attempted, and success has been achieved in producing humanized B-F5 (hereinafter referred to as hB-F5) having similar CD4 binding properties to the parent mouse B-F5.

Thus, in WO 2004/083247, the humanised antibody BT061 (humanised B-F5, or simply hB-F5) has been found to be useful in treating autoimmune diseases, such as psoriasis and rheumatoid arthritis. This antibody is an antibody that is capable of activating CD4+CD25+ regulatory T cells. The patent application discloses compositions for parenteral administration, formulated to allow the administration of a dose of from 0.1-10 mg, preferably from 1-5 mg. Dosage regimes envisaged are an intravenous 1 mg per day dose and a 5 mg every second day dose for rheumatoid arthritis patients over a period of 10 days.

The study was also described by Wijdenes et al., in an abstract and poster presented at the EULAR conference, June 2005. The treatment of 11 patients suffering from rheumatoid arthritis was disclosed. The patients were treated with 5 intravenous infusions of 5 mg BT061 every other day with concomitant treatment with 150 mg Diclophenac.

The antibody described in this study is not disclosed to be suitable for use in higher doses or longer term doses, and it is still desirable to find treatments at longer term doses so as to treat a greater number of patients.

CD4$^+$CD25$^+$ regulatory T cells are able to maintain peripheral tolerance and regulate autoimmunity by inhibiting the proliferation and cytokine production both of antigen specific CD4$^+$ and CD8$^+$ T cells.

Previous studies in mice demonstrated that murine CD4$^+$CD25$^+$ T cells suppress both proliferation and IFN-$\gamma$ production by CD8$^+$ T cells induced either by polyclonal or Ag-specific stimuli. Furthermore CD4$^+$CD25$^+$ T cells inhibit the activation of CD8$^+$ responders by inhibiting both IL-2 production and up-regulation of IL-2R$_\alpha$-chain (CD25) expression (Piccirillo et al., J. Immunol. 167: 1137-1140 (2001)). In contrast to regulatory T cells, conventional T cells express CD25 only upon activation by an immunogen stimulus.

In humans, CD4$^+$CD25$^+$ T cells preactivated by anti-CD3 or anti-CD28 antibody affect CD8$^+$ T cells by leading to reduced proliferation in response to polyclonal and allogeneic stimulation and reduced production of IFN-$\gamma$. Suppressed CD8+ T cells keep their anergic phenotype despite multiple re-stimulations with their cognate antigen and IL-2 for up to 3 weeks. (Camara et al., Eur. J. Immunol. 33:3473-3483 (2003), Dieckman et al., Immunology. 115(3):305-14 (2005)).

SUMMARY OF THE INVENTION

Having regard to the above prior art, it is an aim of the present invention to treat patients having autoimmune diseases with lesser and/or lower doses. In particular, it is an aim of the present invention to find treatments that may be applied to patients at low frequency during a long term therapy, in order to minimize the number of injections needed to obtain a clinical benefit.

Astonishingly, the inventors have observed that BT061 specifically stimulates CD4$^+$CD25$^+$ Tregs which suppress the proliferation of CD8+ T cells by inhibiting the production of IL-2 and IFN-$\gamma$ by alloreactive CD8$^+$ T cells. Furthermore BT061 pre-activated CD4$^+$CD25$^+$ Tregs render suppressed CD8$^+$ T cells unable to express CD25 upon re-stimulation for up to 10 days enabling for the first time a long-term therapeutic effect in treating patients with this antibody, as CD25 expression is one of the hallmarks of activation of such CD8+ T cells. The failure to express CD25 thus results in a reduction of unwanted activation of the immune system.

Accordingly, the invention provides a pharmaceutical composition for treating an autoimmune disease comprising a pharmaceutically acceptable carrier and an agent capable of activating CD4+CD25+ regulatory T cells, wherein the composition is to be administered to a subject at most every 3 days.

Preferably, the period between administrations is at least 4 weeks, at least 12 weeks, at least twenty four weeks, at least 6 calendar months or at least a year. In one embodiment the treatment period is greater than one year and the composition is administered yearly over a period of 1, 2, 3, 4 or 5 years.

In particular, the composition is to be administered most every 6 days, preferably at most every 10 days. Typically the medicament may be administered to a subject every 3-31 days, more preferably every 3-10 days, or every 3-6 days.

The long term nature of the therapy is not especially limited, provided that it is longer than the time required for immediate/acute treatment of the patient concerned. However, periods of at least 6-months, 1 year, 18 months, 2 years and 5 years are envisaged, as well as indefinite periods (e.g. the lifetime of the patient, or until the patient is cured, or displays no symptoms).

When treating patients with an agent capable of activating CD4+CD25+ regulatory T cells both an immediate effect and a long-term therapeutic effect can be demonstrated. Without being bound by theory, this is believed to be due to the fact that agent stimulates CD4+CD25+ Tregs which not only directly inhibit CD8+ T cells but also render CD8+ T cells unable to express CD25 upon re-stimulation. It is thought that long-term effects are further mediated by a combination of effectiveness at low levels and a slow decline of the effective concentration of antibody given in a clinical setting, resulting in extended periods at an effective level of the agent.

It will be appreciated from the above regimes that the inventors have found that, surprisingly, the humanised antibody BT061 (humanised B-F5, or simply hB-F5) does not substantially modulate nor induce release of pro-inflammatory cytokines, as compared to other T cell interacting antibodies (e.g. anti-CD3 antibodies), but stimulates CD4+ CD25+ Tregs which directly inhibit CD8+ T cells plus also renders CD8+ T cells unable to express CD25 upon re-stimulation. Based on the inventors' investigation, dosages may be administered at larger intervals and for a far longer period than disclosed previously in WO 2004/083247.

The concentration of the agent is not especially limited, provided that it is present in a concentration that is appropriate for the patient. However, for high doses preferably, the concentration of the agent is from 10 to 150 mg/ml, 15 to 150 mg/ml, from 15 to 100 mg/ml, from 15 (or greater than 10) to 75 mg/ml, or from 20 to 60 mg/ml. Most preferably, the concentration of the agent is (approximately) any one of 10 mg/ml, 12.5 mg/ml, 20 mg/ml, 25 mg/ml, 50 mg/ml, 60 mg/ml, 70 mg/ml, 80 mg/ml, 90 mg/ml or 100 mg/ml.

In alternative preferred embodiments for lower doses, the concentration of the agent is from 0.1 µg/ml to 30 mg/ml or, 0.1 to 1000 µg/ml, and more preferably from 1-500 µg/ml and 2-250 µg/ml. Most preferably, the concentration of the agent is (approximately) any one of 15 µg/ml, 25 µg/ml, 125 µg/ml, 250 µg/ml, or 500 µg/ml, 1 mg/ml, 12.5 mg/ml or 25 mg/ml.

The invention also provides the use of an agent as defined herein for the manufacture of a medicament for treating autoimmune disease wherein the agent is to be administered to a subject in a dosage regimen described herein. Further the invention provides an agent as defined herein for use in the treatment of autoimmune disease wherein the agent is to be administered to a subject in a dosage regimen described herein.

The dosage volume applied to a subject using the composition is not especially limited, provided that it is delivered over a long term compared to regimes already known, and is therefore suitable for treating individuals who may benefit from long term therapy such as, but not limited to, severe cases with a long history of the disease and insufficient response to current therapies. The concentration of the agent within the dosage volumes can be varied in order to provide the required doses, which are described in this application.

The dosage volume will vary depending on the method of administration. Parenteral administration is preferred. Examples of parenteral administration are intramuscular administration, intravenous administration or subcutaneous administration. Where the composition is to be administered by intravenous infusion the dosage volume may be from 0.1 or 0.5 ml up to 500 ml, preferably between 15 and 25 ml, and typically about 20 ml. Where the composition is to be administered by subcutaneous or intramuscular injection, the dosage volume may be between 0.1 to 3 ml, preferably between 0.5 and 1.5 ml, and typically about 1 ml.

However, in some embodiments the composition may be provided in concentrated form and diluted to the strength required for the individuals concerned. Preferably, in these situations the composition is provided in relatively small volumes of about 1, 2, 3, 4 or 5 ml. In alternative embodiments, the composition is provided at the required strength and dosage volume described above (i.e. ready for administration). In one specific embodiment the pharmaceutical compositions for subcutaneous administration are provided in a ready for administration form which does not require dilution so that they can be easily administered by non-medical personnel.

As has been mentioned previously, it was not known that the agents capable of treating autoimmune diseases could be administered in the long term therapies at low frequencies that are envisaged by the present invention. Whilst known doses of the agents capable of treating autoimmune disease are effective in some individuals or disease types, the realisation that it may be effective for longer periods of time and tolerated for longer periods has opened up the way for more effective treatment of some autoimmune diseases and classes of patients.

BRIEF DESCRIPTION OF THE FIGURES

The invention will be illustrated by way of example only, with reference to the following Figures, in which:

FIG. 3 shows the nucleotide sequence encoding the mouse B-F5 $V_H$ region (SEQ ID No: 5);

FIG. 4 shows the nucleotide sequence encoding the mouse B-F5 $V_k$ region (SEQ ID No: 6);

FIG. 5 shows the nucleotide sequence (SEQ ID No: 3) of a fragment of the plasmid encoding the $V_H$ region of humanized BF-5. The sequence encoding the V region is underlined and the corresponding polypeptide sequence (SEQ ID No: 17) is indicated below the nucleotide sequence;

FIG. 6 shows the nucleotide sequence (SEQ ID No: 4) of a fragment of the plasmid encoding the $V_K$ regions of humanized BF-5. The sequence encoding the V region is underlined and the corresponding polypeptide sequence (SEQ ID No: 2) is indicated below the nucleotide sequence;

FIG. 16A shows a bar chart of the number of tender joints for patients from the dose group receiving 25 mg subcutaneous BT061. FIG. 16B shows a bar chart of the number of swollen joints in patients from the same dose group. Six patients in each group received the antibody dose while two received a placebo.

FIG. 20 shows the alignment of the polypeptide sequences of murine B-F5 $V_K$ (SEQ ID No: 8), FK-001 (SEQ ID Nos: 9, 10, 11 and 12), L4L (SEQ ID No: 18), and L4M (SEQ ID No: 2) in the design of the humanised form of B-F5 (i.e. BT061).

FIG. 21 shows the alignment of the polypeptide sequences of murine B-F5 $V_H$ (SEQ ID No: 7), M26 (SEQ ID Nos: 13, 14, 15 and 16), H37L (SEQ ID No: 1), and H37V (SEQ ID No: 17) in the design of the humanised form of B-F5.

DETAILED DESCRIPTION OF THE PREFERRED EMBODIMENTS

Figure 1:
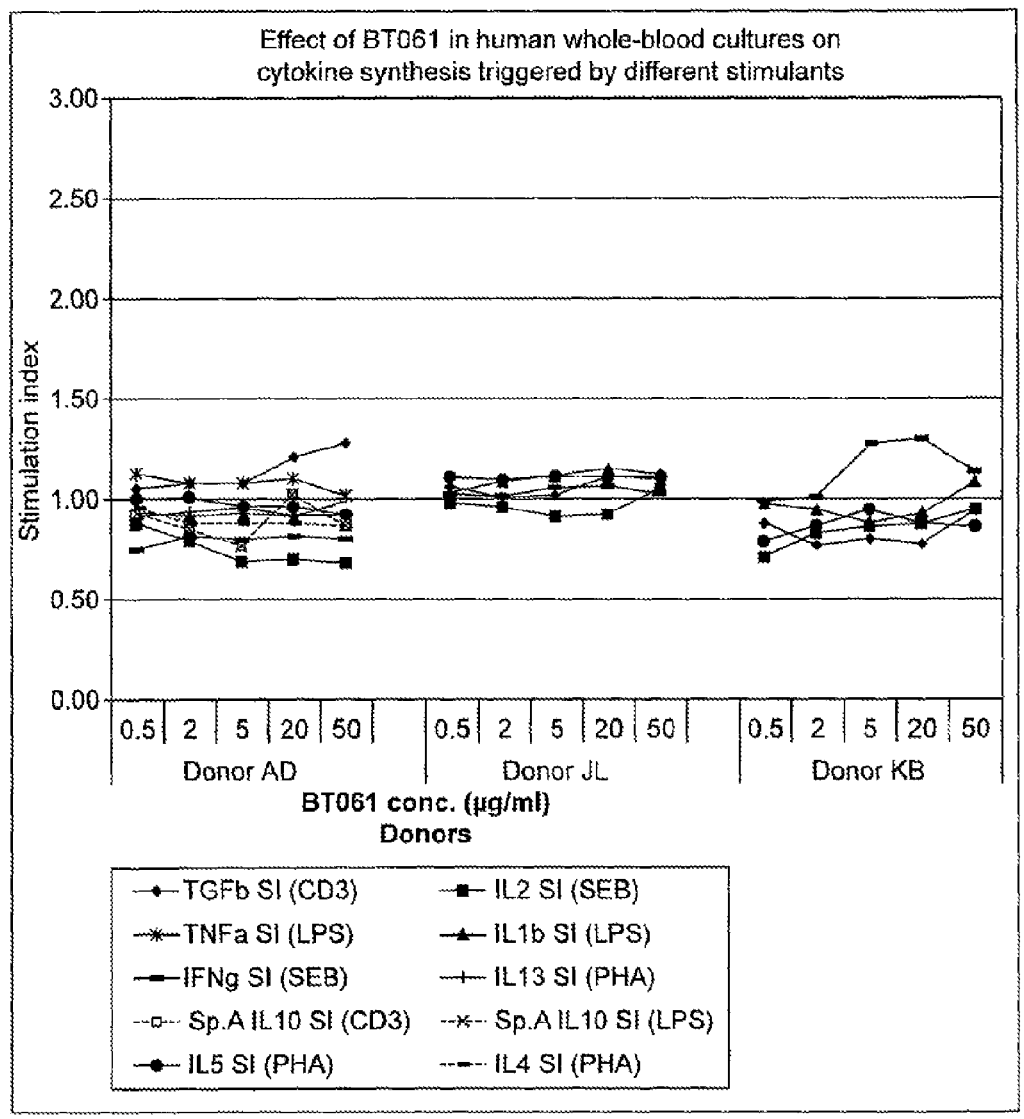
FIG. 1 shows the effect of BT061 on the cytokine synthesis of whole-blood cultures from 3 healthy donors. The cultures were stimulated in separate experiments with 4 different types of activators: CD3=anti-CD3 antibodies; LPS lipopolysaccharide; PHA=phytohaemagglutinin+anti-CD28 antibodies; SEB=staphylococcal enterotoxin B+anti-CD28 antibodies. Different cytokines were determined to measure effects on various leukocyte sub-populations: Treg cells (CD3: TGF-β, IL-10); monocytes/macrophages (LPS: IL-10, TNFα, IL-1β); Th2 cells (PHA: IL-4, IL-5, IL-13); Th1 cells (SEB: IL-2, IFNγ)
Figure 2:
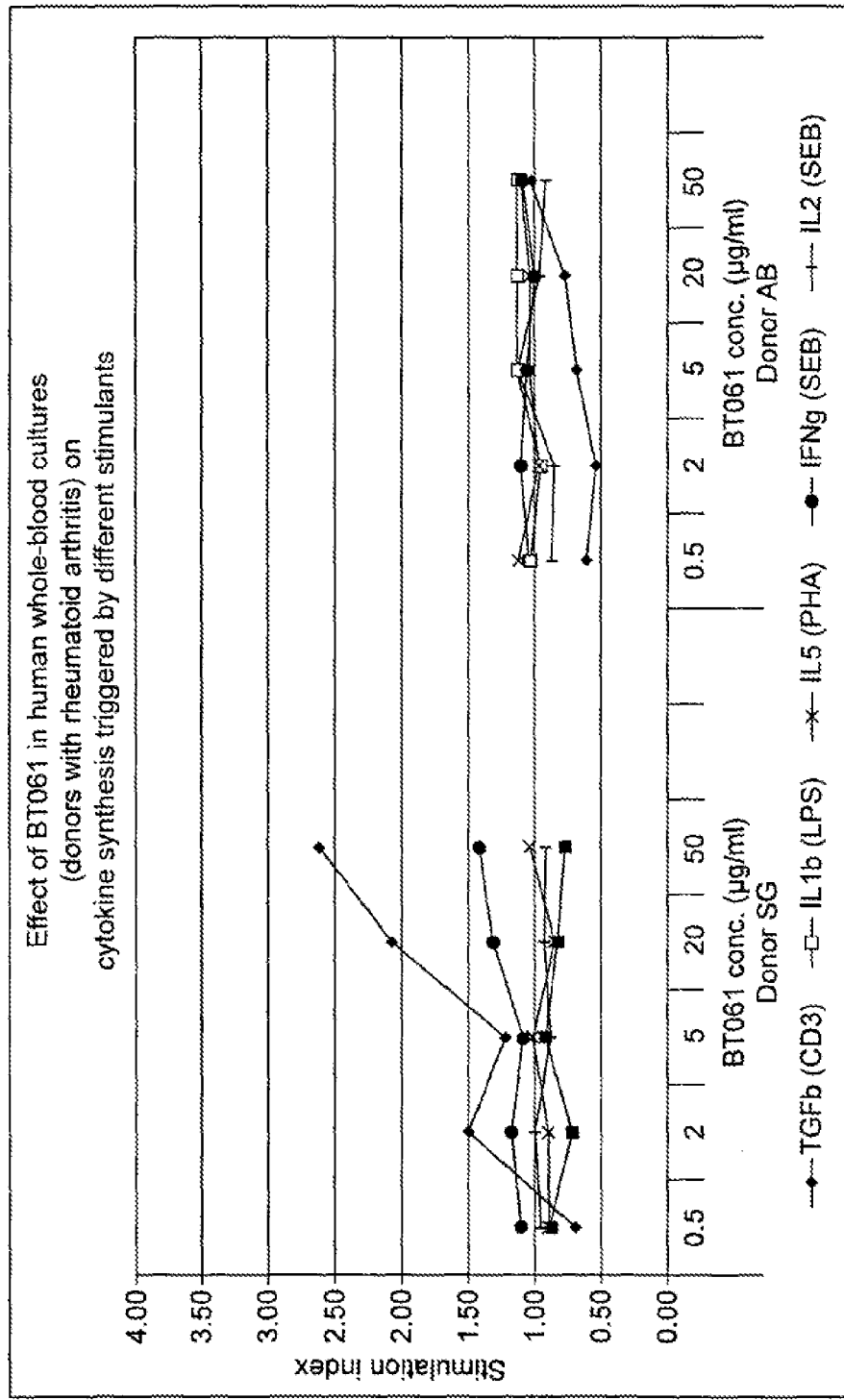
FIG. 2 shows the effect of BT061 in human whole-blood cultures (donors with rheumatoid arthritis) on cytokine synthesis triggered by different stimulants.

The invention will now be described in more detail.

The agents that are suitable for use in the present invention are those which are capable of activating CD4+CD25+ regulatory T cells. The agent may be a polypeptide, a protein or an antibody. Where the agent is an antibody it may be a monoclonal antibody. Preferably the antibody is a monoclonal anti-CD4 antibody. The antibody may also preferably be an IgG1 antibody and may be an unmodified IgG1 antibody.

In a preferred aspect of the invention the agent does not cause a substantial increase in the level of pro-inflammatory cytokines in the subject's blood plasma after administration as compared to anti-CD3 antibodies. In particular, the levels of IFN-γ, TNF-α, IL-6 and/or IL-2 after administration of the agent are not substantially raised compared to plasma levels measured in healthy subjects (see Table A1). Specifically, if the ULN for a specific cytokine given in Table A1 is taken as X then within 96 hours after administration of the agent of the invention there may be less than a 20 fold increase in X. Preferably there may be less than a 10 fold increase in X. More preferably these levels are during the period of 10 minutes after the start of administration to 96 hours after completion of administration.

It is possible that in autoimmune patients, cytokine levels prior to administration of the agent are already higher than those observed in healthy subjects (ULN given in Table A1) e.g. due to a modified activation status of immune cells compared to the activation status of the cells in healthy subjects. In those cases, the concentration for a specific cytokine directly prior to administration of the agent is taken as X and within 96 hours after administration of the agent of the invention there may be less than a 20 fold increase in X. Preferably there may be less than a 10 fold increase in X. More preferably these levels are during the period of 10 minutes after the start of administration to 96 hours after the completion of administration.

TABLE A1

Cytokine levels measured in plasma of healthy volunteers.

| Cytokine | ULN (pg/mL) |
|---|---|
| Il-2 | 19.4 |
| IL-6 | 4.4 |
| TNF-alpha | 2.8 |
| IFN-gamma | 3.8 |

The ULN (upper limit of normal) is calculated based on mean values measure in 39 individual subjects + 2 × standard deviation.

In a further preferred aspect of the invention the agent does not cause a substantial long-lasting decrease in the cell count of CD4+ lymphocytes in the subject's blood plasma. Specifically, within the period of 72 to 96 hours after administration the cell count of CD4+ lymphocytes in the subject's blood plasma may be above 250 cells/µl (or at least 250 cells/µl).

Preferably the cytokine and CD4+ lymphocyte effects described above are seen in at least 80% of patients treated.

To prevent negative impact on the immune system, e.g. a decrease in the lymphocyte cell count or induction of cytokine release, it is known in the art to utilise antibodies (especially T cell interacting antibodies) of subclass IgG2, IgG3 or IgG4 because antibodies of the IgG1 subclass display higher Fc receptor interactions. It is also known in the art to modify antibodies (especially T cell interacting antibodies) by Fc mutation, deglycosylation, glycomodification or glycoengineering to reduce Fc receptor interactions.

The present inventors have found that the avoidance of antibodies of the IgG1 subclass and modifications are not necessary for the agent of the present invention. In particular, the agent of the present invention does not display substantial long-lasting CD4+ cell depletion or induce substantial cytokine release as compared to anti-CD3 antibodies.

Accordingly, in a preferred aspect of the invention the agent is an unmodified IgG1 antibody, i.e. an antibody which does not include an Fc mutation, and has not been subject to deglycosylation, glycomodification or glycoengineering to reduce Fc receptor interactions, or a fragment or a derivative thereof.

The antibodies which are most suitable for use in the present invention are humanized anti-CD4 antibodies, or fragments or derivatives thereof, which are capable of activating CD4+CD25+ regulatory T cells. Examples of antibodies which are capable of capable of activating CD4+ CD25+ regulatory T cells are discussed in Becker et al., (European Journal of Immunology (2007), Vol. 37: pages 1217-1223). Generally, the antibody used in the invention further comprises a human constant region (Fc). This constant region can be selected among constant domains from any class of immunoglobulins, including IgM, IgG, IgD, IgA and IgE, and any isotype, including IgG1, IgG2, IgG3 and IgG4. Preferred constant regions are selected among constant domains of IgG, in particular IgG1.

The present invention also includes any fragment of the antibody comprising the V regions thereof. This comprises in particular Fab, Fab', F(ab)'$_2$, Fv and scFv fragments.

In a particularly preferred aspect of the present invention the antibody is a humanized anti-CD4 antibody or fragment or derivative thereof derived from the mouse monoclonal anti-CD4 antibody B-F5. An example of such an antibody is the BT061 antibody.

BT061 antibody, fragments and derivatives thereof.

The humanized antibody BT061 (hB-F5) is derived from mouse B-F5 mAb, and has V domains defined by the following polypeptide sequences:

H chain V domain:
(SEQ ID NO: 1)
EEQLVESGGGLVKPGGSLRLSCAASGFSFSDCRMYWLRQAPGKGLEWIGV

ISVKSENYGANYAESVRGRFTISRDDSKNTVYLQMNSLKTEDTAVYYCSA

S YYRYDVGAWFAYWGQGTLVTVSS

L chain V domain:
(SEQ ID NO: 2)
DIVMTQSPDSLAVSLGERATINCRASKSVSTGSYSYIYWYQQKPGQPPKL

LIYLASILESGVPDRFSGSGSGTDFTLTISSLQAEDVAVYYCQHSRELPW

TFG QGTKVEIK.

Derivatives of this antibody are also suitable for use in the present invention. Derivatives include those with V domains defined by polypeptide sequences having at least 80%, preferably at least 90%, most preferably at least 95% sequence identity with SEQ ID NO: 1 or SEQ ID No: 2.

Particularly preferred antibodies are those which comprise the complementarity-determining regions (CDRs) of the mouse B-F5 mAb, and retain the ability of hB-F5 to activate CD4+CD25+ regulatory T cells. The location of the CDRs within the V$_H$ and V$_K$ domains is shown in FIGS. 20 and 21. Such antibodies can optionally have variations in the sequence of the CDRs that do not substantially affect the specificity and/or affinity of binding.

Generally, the hB-F5 antibody used in the invention further comprises a human constant region (Fc). As indicated above, this constant region can be selected among constant domains from any class of immunoglobulins, including IgM, IgG, IgD, IgA and IgE, and any isotype, including IgG1, IgG2, IgG3 and IgG4. Preferred constant regions are selected among constant domains of IgG, in particular IgG1.

The present invention also includes any fragment of a BT061 antibody comprising the V regions thereof. This comprises in particular Fab, Fab', F(ab)'$_2$, Fv and scFv fragments.

A polynucleotide encoding the V domain of the H chain or of the L chain of a BT061 antibody may be fused with a polynucleotide coding for the constant region of a human H or L chain, for the purpose of expressing the complete H and L chains obtained in this way; a sequence coding a signal peptide allowing the secretion of the protein can also be added.

The invention also makes use of expression cassettes wherein a polynucleotide as described above is linked to appropriate control sequences allowing the regulation of its transcription and translation in a chosen host cell, and recombinant vectors comprising a polynucleotide or an expression cassette of the invention.

These recombinant DNA constructs can be obtained and introduced in host cells by the well-known techniques of recombinant DNA and genetic engineering.

The invention also makes use of a host cell, transformed by a polynucleotide of the invention. Useful host-cells within the framework of the present invention can be prokaryotic or eukaryotic cells. Among suitable eukaryotic cells, one will mention, by way of example, plant cells, cells of yeasts such as *Saccharomyces*, cells of insects such as *Drosophila*, or *Spodoptera*, and mammal cells such as HeLa, CHO, 3T3, C127, BHK, COS, etc.

The construction of expression vectors used in the invention, and the transformation of host-cells can be made by the standard techniques of molecular biology.

The BT061 (hB-F5) antibody used in the invention can be obtained by culturing a host cell containing an expression vector comprising a nucleic acid sequence encoding said antibody, under conditions suitable for the expression thereof, and recovering said antibody from the host cell culture.

Construction of Humanized B-F5

Design of Humanized B-F5 $V_H$ and $V_K$ Regions

DNA sequences encoding mouse B-F5 $V_H$ and $V_K$ regions are respectively shown in FIG. 3 and FIG. 4 and under sequence identifiers SEQ ID NO:5 and SEQ ID NO:6. The human $V_H$ and $V_K$ on which the mouse CDRs are grafted were selected by searching databases for human $V_H$ most like the original mouse B-F5 $V_H$ and $V_K$. $V_H$ region of a human antibody (M26; Accession Number A36006) had the highest homology with B-F5 $V_H$. VK region of another human antibody (FK-001; NAKATANI et al., *Biotechnology*, 7 (1989), 805-810)) had the highest homology with B-F5 $V_K$.

Two types of $V_K$ differing between them in that the $4^{th}$ residue was Leucine or Methionine were constructed and designated as L4L and L4M. Two types of VH differing between them in that the $37^{th}$ amino acid residue was Leucine or Valine, were constructed and designated as H37L and H37V. The alignment of the polypeptide sequences of B-F5, FK-001, L4L, and L4M is shown in FIG. 20. The alignment of the polypeptide sequences of B-F5, M26, H37L, and H37V is shown in FIG. 21. The FR residues previously reported to be important for the packing of CDRs (Chothia et al., Nature 342 (1989), 877; Foote et al., J. Mol. Biol., 224 (1992), 487) are boxed.

By combining these $V_H$ and $V_K$, 4 versions of V regions were designed.

Expression of Humanized B-F5

The subsequent steps for production of humanized B-F5 were the same as those disclosed in U.S. Pat. No. 5,886,152 for humanized B-B10.

Briefly, expression plasmids for the H chain ($V_H$ humanized region fused to the constant region of a human y-1 chain (TAKAHASHI et al., *Cell*, 29 (1982), 671-679)) and the L chain (VK humanized region fused to the constant region of FK-001 K chain) of humanized B-F5 were constructed separately. In these plasmids, the expression of humanized B-F5 is driven by the promoter/enhancer of the gene of human monoclonal IgM, FK-001. FIGS. 5 and 6 respectively show the fragments of the plasmids encoding the VH and $V_K$ regions of humanized BF-5. The sequences encoding the V region are underlined and the corresponding polypeptide sequences are indicated underneath the nucleotide sequence. Both plasmids and pSV2neo were simultaneously introduced into mouse myeloma Sp2/0 (ATCC CRL-1581) using Lipofectin$^{mi}$. Transfectomas producing human IgG were selected by ELISA, using an anti-human IgG (y chain) antibody and an anti-human Ig K chain antibody.

Characterisation of the Different Versions of Humanized B-F5

Estimation of CD4 Binding Activity

Culture supernatants of transfectomas producing the four versions of hB-F5 were collected, and concentrated. The different antibodies were purified from culture supernatants by affinity chromatography using protein A Sepharose and assessed for their CD4 binding activity by measuring, by means of competitive ELISA, their inhibitory activities against the binding of biotinylated mB-F5 to soluble CD4 coated on microtiter plates. Incubation, time is 2 hours for 37° C. and overnight for 4° C.

The relative binding activities of hB-F5s (binding activity of mB-F5 was taken as 100%) are shown in Table A below:

TABLE A

| Antibody | Temp (° C.) | Relative binding activity (% of mB-F5) |
| --- | --- | --- |
| H37L/L4L | 4 | 80 |
|  | 37 | 30 |
| H37L/L4M | 4 | 80 |
|  | 37 | 30 |
| H37V/L4L | 4 | 10-20 |
|  | 37 | 10 |
| H37V/L4M | 4 | 10-20 |
|  | 37 | 10 |

From the results shown in Table A, it appears that the 37th residue of Leucine, is critical to maintain CD4 binding activity of hB-F5 because the CD4 binding activity is several-fold reduced by conversion of $^{37}$Leu to $^{37}$Val. On the contrary, the 4th residue of $V_K$ is found to be not so important for the CD4 binding activity. As the structural difference between $^{37}$Leu and $^{37}$Val of $V_H$ is not clearly demonstrated by molecular modeling, the superiority of H37L to H37V in CD4 binding activity was unexpected.

H37L/L4L and H37L/L4M were chosen for evaluation.

Investigation of the In Vitro Biological Activities of Humanized B-F5

The in vitro biological activities of mouse B-F5 and humanized B-F5s (H37L/L4M IgG1 and H37L/L4L IgG 1) were evaluated. Humanized B-F5s of IgG2 type (H37L/L4M IgG2 and H37L/L4L IgG2) were also tested.

The in vitro biological activities of mB-F5 and the four types of hB-F5s were evaluated using peripheral blood mononuclear cells (PBMCs) from healthy donors. PBMCs were activated by ConA (2.5 pg/ml, 3 days) or PPD (10 pg/ml, 4 days) in the presence of murine or hB-F5s, and were monitored for their proliferative responses by 3H-thymidine incorporation.

Murine and hB-F5s could moderately inhibit ConA-induced proliferation, but the activities varied from antibody to antibody and/or from donor to donor. Also, murine and hB-F5s were able to inhibit Ag-specific PBMC proliferation induced by PPD.

IgG1 type of hB-F5 inhibited PPD-induced proliferation more effectively (as high as 70% inhibition) than mB-F5. IgG1 type seemed to be more effective than IgG2 type of which inhibitory activity was almost the same as mB-F5. For IgG1 type, H37L/L4M was more effective than H37L/L4L.

IgG2 type of H37L/L4M and H37L/L4L had almost the same inhibitory activities. In short, the inhibitory activities of B-F5s against PPD-induced PBMC proliferation were as follows: H37L/L4M IgG1>H37L/L4L IgG1>H37L/L4M IgG2=H37L/L4L IgG2=mB-F5.

Considering the efficacy of the in vitro biological activity and the smaller number of mouse amino acids, H37L/L4M IgG1 was chosen for further evaluation, and it is this antibody which is named BT061 and is employed to demonstrate the present invention in the Examples provided in this application.

Compositions and Uses

As has been mentioned, the pharmaceutical composition and medicaments used in the present invention, are preferably capable of treating an autoimmune disease in patients benefiting from longer term therapies.

In some embodiments (higher doses) the preferred doses of the agent are those from 10 mg to 100 mg, 10 mg to 80 mg, 15 mg to 80 mg, 20 mg to 75 mg, preferably from 20 mg to 60 mg and most preferably from 25 mg to 60 mg.

Alternatively, the dosage may be defined based on the cumulative dose over plurality of doses. In particular, for a plurality of doses over a period of 10 days it is preferred that the cumulative dose is between greater than 25 mg but less than or equal to 200 mg, more preferably between 28 mg and 100 mg, and most preferably between 30 mg and 100 mg. Further, the cumulative dose over a period of 5 days are preferably greater than 15 mg but less than or equal to 100 mg, more preferably between 18 mg and 100 mg and most preferably between 20 mg and 100 mg. In this aspect of the invention it is particularly preferred that the dosages are administered subcutaneously.

In an alternative embodiment (lower doses) the preferred doses are those of 0.2 mg to 30 mg, 0.2 to 20 mg per dose, 0.3 mg to 7.5 mg, 0.3 to 5 mg per dose or preferably 0.3 to 1 mg per dose.

Alternatively, the dosage may be defined based on the cumulative dose over plurality of doses. In particular, for a plurality of doses over a period of 10 days it is preferred that the cumulative dose is between 0.2 to less than 25 mg, more preferably between 0.2 and 20 mg and most preferably between 0.2 to less than 10 mg. Further, the cumulative dosage over a period of 5 days should be between 0.2 to less than 15 mg, preferably between 0.2 and 12 mg, and more preferably between 0.2 to less than 5 mg.

In this aspect of the invention it is preferred that, when the dose is to be administered intravenously, the dosages over a period of 10 days are between 0.2 to less than 10 mg, most preferably between 0.2 and 7.5 mg. Alternatively, where the doses are to be administered subcutaneously or intramuscularly, it is preferred that the dosages over a period of 10 days are between 1 mg to 30 mg, more preferably between 5 mg and 30 mg.

The dose can also be calculated on the basis of the body weight of the subject or the body surface area (BSA) of the subject. Body surface area (BSA) can be calculated according to any known method. Examples of BSA calculation methods are as follows:

$$BSA(m^2) = ([Height(cm) \times Weight(kg)]/3600)^{1/2} \quad \text{Mosteller formula}$$

(Mosteller R D: Simplified Calculation of Body Surface Area. *N Engl J Med* 1987 Oct. 22; 317(17):1098)

$$BSA(m^2) = 0.20247 \times Height(m)^{0.725} \times Weight(kg)^{0.425} \quad \text{DuBois and DuBois formula}$$

(DuBois D; DuBois E F: A formula to estimate the approximate surface area if height and weight be known. *Arch Int Med* 1916 17:863-71.

$$BSA(m^2) = 0.024265 \times Height(cm)^{0.3964} \times Weight(kg)^{0.5378} \quad \text{Haycock formula}$$

(Haycock G. B., Schwartz G. J., Wisotsky D. H. Geometric method for measuring body surface area: A height weight formula validated in infants, children and adults. *The Journal of Pediatrics* 1978 93:1:62-66)

$$BSA(m^2) = 0.0235 \times Height(cm)^{0.42246} \times Weight(kg)^{0.51456} \quad \text{Gehan and George formula}$$

(Gehan E A, George S L, Estimation of human body surface area from height and weight. *Cancer Chemother Rep* 1970 54:225-35)

$$BSA(m^2) = 0.0003207 \times Height(cm)^{0.3} \times Weight(grams)^{(0.7285-(0.0188 \times LOG(grams)))} \quad \text{Boyd formula}$$

According to the higher dose embodiments of the invention the dose of the agent to the subject in terms of body weight is from 0.1 to 2 mg/kg, preferably 0.15 to 1.5 mg/kg, and most preferably 0.2 to 1 mg/kg. In terms of BSA the dose of the agent to the subject is from 5 to 60 mg/m² BSA, preferably from 6 to 50 mg/m², and most preferably 8 to 40 mg/m².

In these aspects of the invention, where the dose is based on the body surface area or the body weight of the subject it is preferred that the doses over a period of 10 days are between 10 mg/m² and 120 mg/m², more preferably between 16 mg/m² and 120 mg/m², or between 0.2 mg/kg and 4 mg/kg, more preferably between 0.4 mg/kg and 4 mg.kg. It is particularly preferred that the dosages are administered subcutaneously.

According to the lower dose embodiments of the invention the dose of the agent to the subject in terms of body weight is from 1 to 500 µg/kg, preferably 2 to 400 µg/kg, more preferably 2 to 250 µg/kg and most preferably 2.5 to 20 µg/kg. In terms of BSA the dose of the agent to the subject is from 0.12 to 15 mg/m², more preferably 0.20 to 10 mg/m² and most preferably 0.30 to 0.50 mg/m².

In these aspect of the invention where the dose is based on the body surface area or the body weight of the subject it is preferred that, when the dose is to be administered intravenously, the dosages over a period of 10 days are between 0.20 to 10 mg/m², more preferably between 0.20 to 4 mg/m², or between 2 to 250 µg/kg, more preferably between 2 to 100 µg/kg. Alternatively, where the doses are to be administered subcutaneously or intramuscularly, it is preferred that the dosages over a period of 10 days are between 0.30 to 20 mg/m², more preferably between 0.5 to 20 mg/m², or between 2.5 to 500 µg/kg more preferably between 20 to 500 µg/kg.

The frequency of administration is not especially limited, provided that it affords the advantages of the log term treatment. In the invention, it is preferred that the plurality of doses are administered on at least the following bases: 3-daily, weekly, every four weeks, every 6 weeks, every 12 weeks, every 24 weeks, every calendar month, every 3 calendar months, every six calendar months or yearly. Thus, the doses may be separated by at least three days, or alternatively by at least one week, by at least 10 days, by at least one month, by at least 3 months, by at least 6 months, or by at least one year (meaning that the doses are taken at least every 3 days, every week, every 10 days, every month, every 3 months, every 6 months, or every year). In a further alternative the plurality of doses are taken from every 3 to 31 days, every 3-10 days, every 3-6 days or from every 1-12 months.

The invention also provides a kit for a use as defined above, wherein the kit comprises a plurality of medicament dosages as defined above for simultaneous, sequential or separate administration to a subject.

It also provides a method of treatment of an autoimmune disease, which method comprises administering a medicament as defined above, in a manner as defined above, to a subject.

As has been mentioned, the pharmaceutical composition and medicaments used in the present invention, are preferably capable of treating an autoimmune disease in patients benefiting from longer term therapies. Such patients include but are not limited to severe cases with a long history of the disease.

Generally the pharmaceutical composition and medicaments used according to the present invention are for treating an autoimmune disease. Preferably the autoimmune disease is selected from psoriasis, rheumatoid arthritis, multiple sclerosis, type-1 diabetes, inflammatory bowel diseases, Crohn's disease, Hashimoto's thyreoiditis, autoimmune thyreoiditis, autoimmune myasthenia gravis, systemic lupus erythematosus, ulcerative colitis, atopic dermatitis, myocarditis and transplantation-related diseases such as graft-versus-host or host-versus graft reactions, or general organ tolerance issues.

In a particularly preferred aspect of the invention the pharmaceutical compositions are for treating the autoimmune disease psoriasis. In particular, such pharmaceutical compositions are to be administered intravenously or subcutaneously in the dosages specified herein.

Psoriasis is a disorder which causes psoriatic lesions or plaques on the sufferer's skin.

The Psoriasis Area and Severity Index (PASI) score is commonly used to evaluate and record the level of psoriasis exhibited by sufferers. PASI scoring involves the assessment of erythema (E), infiltration (I), and desquamation (D), and body surface area involvement (A) over 4 body regions (head (h), trunk (t), upper (u) and lower (l) extremities). Table B below shows how the scoring system works.

TABLE B

PASI scoring system

| Degree of severity (per body region) | Value given | Surface involved (per body region) | Value given |
|---|---|---|---|
| No symptoms | 0 | <10% | 1 |
| Slight | 1 | 10-29% | 2 |
| Moderate | 2 | 30-49% | 3 |
| Marked | 3 | 50-69% | 4 |
| Very marked | 4 | 70-89% | 5 |
|  |  | 90-100% | 6 |

Because the head, upper extremities, trunk, and lower extremities correspond to approximately 10, 20, 30, and 40% of body surface area, respectively, the PASI score is calculated by the formula:

$$PASI=0.1(E_h+I_h+D_h)A_h+0.2(E_u+I_u+D_u)A_u+0.3(E_t+I_t+D_t)A_t+0.4(E_l+I_l+D_l)A_l$$

PASI score ranges from 0-72. A score of 0 means no psoriasis, while a score of 72 represents the most severe psoriasis.

In a preferred embodiment of this aspect the pharmaceutical composition of the present invention is capable of treating psoriasis by providing at least a 40%, and preferably at least a 50%, improvement in the PASI score of the patient. Preferably the subject has a PASI score of at least 10 prior to treatment. These effects may be seen at least 56 days after administration of a single dose of the antibody, more preferably at least 75 days after administration of a single dose of the antibody. In particular, these effects may be seen in at least 80% of patients.

In a further aspect of the present invention the pharmaceutical compositions are for treating rheumatoid arthritis.

Rheumatoid arthritis is an autoimmune disease which causes chronic inflammation of joints and surrounding tissues, and can also affect other tissues and body organs.

Improvement in rheumatoid arthritis exhibited by a treated patient is commonly assessed using the American College of Rheumatology (ACR) core set of parameters (Felson et al., Arthritis & Rheumatism, 1995, 38(6), 727-735). This system defines a value of ACR 20 as a 20% improvement in tender and swollen joint counts and 20% improvement in 3 of the 5 remaining ACR core set measures: patient and physician global assessments, pain, disability, and an acute phase reactant, such as C-reactive protein (CRP).

In particular, the pharmaceutical compositions for treating rheumatoid arthritis are preferably to be administered intramuscularly or subcutaneously in the dosages specified herein.

Present treatment of arthritis includes first line drugs for controlling pain and inflammation classified as non-steroidal anti-inflammatory drugs (NSAIDs), e.g., aspirin, ibuprofen, naproxen, etc. Secondary treatment of arthritis includes corticosteroids (e.g. prednisone and dexamethasone), slow acting antirheumatic drugs (SAARDs) or disease-modifying anti-rheumatic drugs (DMARDs), e.g., methotrexate, pencillinamine, cyclophosphamide, gold salts, azothipoprine, leflunomide, etc.

Corticosteroids, the synthetic versions of the body's cortisone hormone, are used to inhibit RA progression (e.g. prednisone and dexamethasone).

Another group of drugs called biological-response modifiers (BRMs) has also been developed for treatment of RA including antagonists to TNF-alpha (adalimumab, infliximab, etanercept) which work through binding to its receptor or directly binding to the TNF-alpha protein.

In one embodiment of this aspect of the invention the compositions are to be administered in combination with drugs currently used to treat rheumatoid arthritis. In particular, the compositions are to be administered with one of the drugs mentioned above, preferably methotrexate.

Known drugs, such as methotrexate, and the pharmaceutical composition of the present invention can be administered simultaneously, sequentially or separately.

The invention will now be described further in relation to the following non-limiting specific embodiments.

EXAMPLES

Example 1

Investigation of the Immuno-Modulating Capacities of BT061 Regarding T Cell Proliferation Method Whole-blood cultures were performed with freshly drawn peripheral blood. Briefly, using 19G needles blood from three healthy volunteers was collected into heparinised syringes. The blood was seeded into 96-well culture plates not later than 60 min after donation.

The antibody used in the invention (BT061, lot 40588, or lot 70A0013B) was added to the cultures before stimulation of the leukocytes at 5 different concentrations (see "Test substances" below) The cells were allowed to interact with the antibody for 90 min at 37° C., 5% $CO_2$ in humidified atmosphere, then four different stimulants were added to separate cultures:

(a) anti-CD3 antibodies (R&D Systems; 50 ng/ml)
(b) phytohaemagglutinin (PHA, Biochrom KG; 3 pa/ml) together with anti-CD28 antibodies (Becton-Dickinson; 1 μg/ml);
(c) lipopolysaccharide (LPS, subtype O55:B15 from Sigma Aldrich; 1 μg/ml);
(d) SE-B (Bernhard-Nocht-Institut; 25 ng/ml) together with anti-CD28 antibodies (Becton-Dickinson; 1 μg/ml).

All whole-blood cultures were incubated for 24 hrs at 37° C., 5% $CO_2$ (humidified atmosphere). Then the culture supernatants were collected for the determination the cytokine endpoints, except for PHA/antiCD28 stimulated cultures, which were incubated for 48 hrs in order to obtain a sufficient stimulation of Th2 cells.

The results are set out in FIG. 1.

Results

BT061 displayed no significant effect on the major activities of monocytes/macrophages and on Th1 as well as Th2 activities in whole blood cultures from healthy volunteers. There was a concentration-dependent effect on Treg cells (demonstrated as an increase in TGF-beta release).

In particular, the results confirm that there is:

No modulation of the inflammatory cytokine IL-2 at concentrations of up to 50 μg/ml corresponding to high dose application of up to 150 mg in patients No induction of the inflammatory cytokine IFN-gamma at concentrations of up to 50 μg/ml corresponding to high dose application of up to 150 mg in patients No modulation of the Th1/Th2 cytokines at concentrations of up to 50 μg/ml corresponding to high dose application in patients Only very sporadic up-regulation of IL-6 by a marginal increment occurred, the implications of which are discussed controversial Increase in TGF-beta release (Treg cells)

No significant effect on major regulatory activities of monocytes/macrophages and on Th1 and Th2 activities.

Example 2

Testing of BT061 for its Influence on Cultivated Human PBMCs Primed for an Anti-Tetanus Toxoid Response and Cytokine Assay Method Proliferation Assay Freshly isolated PBMC were cultivated in 96 well flat bottom microtiter-plates in a volume of 200 μl/well ($4\times10^5$ cells/well). The test-item (Anti CD4 mAb BT061) was used in the concentrations of 20 μg/ml, 4 μg/ml and 0.8 μg/ml (additionally 40 μg/ml within the pre test); Tetanus-Toxoid was used in concentrations of 25 μg/ml, 5 μg/ml and 1 μg/ml. For the negative control cell culture medium was taken. All cultures were set up as triplicates.

For the ConA-stimulation a concentration of 2.5 μg/ml and a volume of 200 μDwell was used. The PBMC was adjusted to a density of $1\times10^6$/ml and dispensed in a volume of 100 μl per well.

At the end of the culture period, cell proliferation was detected by adding 0.4 μCi of $^3$H-thymidine per well for sixteen hours. At the end of the culture period the cells were detached from the surface using EDTA solution and harvested on glass fibre filters using a scatron cell harvester. The amount of radioactivity incorporated into DNA in each well was measured in a scintillation counter and is proportional to the number of proliferating cells, which in turn is a function of the number of leukocytes that were stimulated to enter the S-phase of the cell cycle. The readout parameter was counts per minute (cpm) and the stimulation index (SI) for each concentration defined as $cpm_{compound}/cpm_{blank}$.

Cytokine Assays

All cytokines were quantified in the culture supernatants using commercial ELISA kits, according to the respective manufacturers instructions. The reagents employed are set out in Table 1 below:

TABLE 1

| substance | source | code | lot |
|---|---|---|---|
| Human IFN-γ OptEIA Set | BD Biosciences | 555142 | MF31099 |
| Human IL-1 ELISA Set | Bender | BMS243/2MST | n.a. |
| Human IL-4 OptEIA Set | BD Biosciences | 555194 | MF10142 |
| Human IL-5 OptEIA Set | BD Biosciences | 555202 | MF31662 |
| Human IL-6 OptEIA Set | BD Biosciences | 555220 | MF25815 |
| Human IL-10 OptEIA Set | BD Biosciences | 555157 | MF24968 |
| Human TGF-β OptEIA Set | BD Biosciences | 559119 | 47704 |
| Human TNF-α OptEIA Set | BD Biosciences | 555212 | MF31447 |

* additional material, required for the Interleukin-1 ELISA

Interleukin (IL)-1 levels in culture supernatants were determined using the human IL-1 ELISA Set A (Bender) test kit according to the manufacturers instructions. The range of the test, predetermined by the standard delivered with the kit, was specified at 1.3 to 130 pg/ml for undiluted samples.

IL-4, 5, 6 and 10 levels in culture supernatants as well as transforming growth factor (TGF) β1 and tumour necrosis factor (TNF) a were determined using the OptEIA (BD biosciences) test kit according to the manufacturers instructions. The range of the tests, predetermined by the standards delivered with the kits was specified at 3.8 to 330 pg/ml for IFN-γ, 6.3 to 616 pg/ml (for IL-4, 5, 10 and TNF), measuring undiluted samples and 7.6 to 660 pg/ml for IL-6 using twofold dilutions of the samples.

Two (for monocyte cultures) or eight (for PBMC cultures) cytokine determinations by ELISA, each from independent micro-cultures were included in the calculation of mean and standard deviation. Titres above the upper range of the test (e.g. 616 pg/ml in the case of TNF) were set to this value for calculation. The lower range of the test was subtracted from each mean value prior calculation.

Results

BT061 (also termed humanised B-F5, or simply hB-F5) is able to suppress dose-dependently the tetanus-toxoid specific T cell proliferation; there has been no effect on the total number of T cells. General suppression of cytokine release has been demonstrated.

Table 2 below shows the influence of the anti CD4 mAb BT061 on a tetanus-toxoid-specific T-cell proliferation assay, measured in triplicates.

Displayed are the means and SD of the $^3$H-Tdr-incorporation, measured in triplicates as well as the stimulation index (SI, defined as $cpm_{compound}/cpm_{nil}$) for each concentration and the level of significance in the unpaired, two sided t-test against the medium control (n.s.: not significant; *: $p<0.05$; : $p<0.01$; *: $p<0.001$).

TABLE 2

| anti CD4 (BT061) | Tetanus Toxoid | | | |
|---|---|---|---|---|
| | 25 µg/ml | 5 µg/ml | 1 µg/ml | nil |
| 20 µg/ml | | | | |
| Mean (cpm) | 5123 | 2426 | 2589 | 456 |
| SD (cpm) | 597 | 989 | 1069 | 363 |
| Mean (SI) | 11.23 | 5.32 | 5.67 | 1.00 |
| SD (SI) | 10.24 | 6.40 | 6.85 | 1.59 |
| t-test (compound vs. nil) | | | | |
| p = | 0.000*** | 0.032* | 0.031* | |
| 4 µg/ml | | | | |
| Mean (cpm) | 6591 | 5005 | 2957 | 358 |
| SD (cpm) | 468 | 518 | 1333 | 57 |
| Mean (SI) | 18.39 | 13.97 | 8.25 | 1.00 |
| SD (SI) | 4.21 | 3.65 | 5.02 | 0.32 |
| t-test (compound vs. nil) | | | | |
| p = | 0.000*** | 0.000*** | 0.028* | |
| 0.8 µg/ml | | | | |
| Mean (cpm) | 8787 | 6748 | 3902 | 414 |
| SD (cpm) | 1886 | 763 | 218 | 12 |
| Mean (SI) | 21.24 | 16.31 | 9.43 | 1.00 |
| SD (SI) | 5.18 | 2.32 | 0.80 | 0.06 |
| t-test (compound vs. nil) | | | | |
| p = | 0.002 | 0.000 | 0.000 | |
| nil | | | | |
| Mean (cpm) | 13783 | 10244 | 6970 | 650 |
| SD (cpm) | 1826 | 758 | 1351 | 95 |
| Mean (SI) | 21.22 | 15.77 | 10.73 | 1.00 |
| SD (SI) | 5.91 | 3.47 | 3.65 | 0.29 |
| t-test (compound vs. nil) | | | | |
| p = | 0.000*** | 0.000*** | 0.001** | |

| Viab-ctr | ConA | nil |
|---|---|---|
| Mean (cpm) | 94473 | 404 |
| SD (cpm) | 4200 | 239 |
| Mean (SI) | 233.94 | 1.00 |
| SD (SI) | 148.86 | 1.18 |
| t-test (compound vs. nil) | | |
| p = | 0.000*** | |

Tables 3A and 3B

These tables show the influence of the anti CD4 mAb BT061 on the cytokine production of tetanus-toxoid-stimulated PBMC cultures. Mean and SD of eight individual micro cultures are given.

TABLE 3A

| BT061 µg/ml | Tet. Tox. µg/ml | IL-1 pg/ml mean | SD | IL-4 pg/ml mean | SD | IL-5 pg/ml mean | SD | IL-6 pg/ml mean | SD |
|---|---|---|---|---|---|---|---|---|---|
| 20 | 25 | 0.0 | 0.0 | 0.0 | 0.0 | 26.3 | 10.1 | 141.8 | 16.9 |
| 4 | 25 | 0.0 | 0.0 | 0.0 | 0.0 | 53.0 | 20.4 | 143.3 | 40.3 |
| 0.8 | 25 | 0.0 | 0.0 | 0.0 | 0.0 | 83.7 | 41.8 | 144.2 | 15.2 |
| 0 | 25 | 0.1 | 0.2 | 0.2 | 0.6 | 150.1 | 59.5 | 133.3 | 13.5 |
| 25 | 0 | 0.5 | 0.0 | 0.0 | 0.0 | 0.0 | 0.0 | 124.8 | 16.9 |
| 0 | 0 | 0.0 | 0.0 | 0.0 | 0.0 | 0.0 | 0.0 | 123.7 | 14.5 |

TABLE 3B

| BT061 µg/ml | Tet. Tox. µg/ml | IL-10 pg/ml mean | SD | IFN-γ pg/ml mean | SD | TGF-β1 pg/ml mean | SD | TNF α pg/ml mean | SD |
|---|---|---|---|---|---|---|---|---|---|
| 20 | 25 | 22.9 | 4.5 | 0.9 | 1.6 | 35.5 | 46.1 | 2.2 | 3.1 |
| 4 | 25 | 20.9 | 5.3 | 3.3 | 3.6 | 15.9 | 23.8 | 2.1 | 2.2 |
| 0.8 | 25 | 21.4 | 4.1 | 17.9 | 24.1 | 14.3 | 27.1 | 5.5 | 4.0 |
| 0 | 25 | 27.2 | 5.9 | 41.0 | 34.8 | 12.4 | 27.6 | 8.5 | 5.5 |
| 25 | 0 | 8.7 | 2.5 | 0.0 | 0.0 | 8.8 | 18.4 | 0.0 | 0.0 |
| 0 | 0 | 6.7 | 1.9 | 0.0 | 0.0 | 5.4 | 13.1 | 0.0 | 0.0 |

This table shows the influence of the anti CD4 mAb BT061 on the production of inflammatory cytokines LPS-stimulated monocyte cultures. Mean and SD of two individual micro cultures are given.

TABLE 4

| | IL-1 pg/ml | | | | IL-6 pg/ml | | | | TNF α pg/ml | | | |
|---|---|---|---|---|---|---|---|---|---|---|---|---|
| BT061 | LPS 1 µg/ml | | nil | | LPS 1 µg/ml | | nil | | LPS 1 µg/ml | | nil | |
| µg/ml | mean | SD | mean | SD | mean | SD | mean | SD | mean | SD | mean | SD |
| 20.0 | 40 | 14.7 | 0 | 0 | 253 | 2.4 | 121 | 12.2 | 609 | 0.0 | 0.3 | 0.4 |
| 4.0 | 39 | 8.1 | 0 | 0 | 256 | 14.9 | 135 | 8.9 | 597 | 12.7 | 0.0 | 0 |
| 0.8 | 34 | 14.8 | 0.2 | 0.3 | 257 | 16.6 | 128 | 5.9 | 605 | 5.7 | 0.0 | 0 |
| 0.0 | 56 | 2.2 | 0 | 0 | 233 | 16.6 | 117 | 14.1 | 600 | 3.2 | 0.6 | 0.8 |

The data in Tables 2-4 demonstrate the following:

A dose dependent suppression of tetanus toxoid-induced T cell proliferation (recall response) has been demonstrated even at high doses of BT061, showing that BT061 does not abrogate all immune responses. Doses used apply to a corresponding high dose application of up to 60 mg in patients General suppression of cytokine release (dose-dependent reduction of IFN-gamma, IL-5 and TNF-alpha, with no change in IL-1, IL-4, IL-6, IL-10) and without affecting Th1/Th2 balance.

An increase in TGF-beta release

Example 3

A Flow Cytometric Test for BT061 (Anti-CD4 mAb) Induced ADCC (Antibody-Dependent, Cell-Mediated Cytotoxicity)

HuT 78 target cells were labelled with BT061 (hB-F5) and incubated with PBMC cells as effectors. Dead cells could be detected due to the uptake of the DNA dye propidium iodine after an incubation time of 30 minutes. Results are shown in Table 5.

TABLE 5

| Concentration [µg/ml] | Tecelac/ATG) (positive control) mean fluorescence intensity | Negative control mean fluorescence intensity | Specific cell death (ADCC) [%] |
|---|---|---|---|
| 75 | 31.78 | 11.96 | 19.82 |
| 37.05 | 25.09 | 12.70 | 12.39 |
| 18.75 | 22.25 | 10.59 | 11.66 |
| 9.38 | 14.95 | 10.63 | 4.32 |

| Concentration [µg/ml] | hB-F5 mean fluorescence intensity | Negative control mean fluorescence intensity | Specific cell death (ADCC) [%] |
|---|---|---|---|
| 70.85 | 10.96 | 13.41 | −2.45 |
| 35.43 | 11.06 | 14.05 | −2.99 |
| 17.71 | 11.68 | 12.16 | −0.48 |
| 8.86 | 10.54 | 10.23 | 0.31 |

The data in the table demonstrate that there was no induction of ADCC by BT061 (hB-F5) even at high concentrations Example 4

Apoptosis

In a flow cytometric test for BT061 (anti-CD4 mAb) induced apoptosis, PBMCs from full blood were incubated with BT061 or the positive control.

After an incubation time of 7 days, the detection of apoptotic cells was performed by staining of apoptotic cells with Annexin-V-Fluoresceine. The results are shown in Table 6.

TABLE 6

7 d stimulation experiments

| Antibody concentration [µg/ml] | Stimulus | |
|---|---|---|
| | Positive control (ATG/Tecelac) | BT061 |
| | Increase of the ratio of apoptotic cells [%] | |
| 400 | 0.8 | −6.9 |
| 200 | 13.6 | −6.4 |
| 100 | 19.5 | −0.7 |
| 50 | 17.3 | −0.4 |
| 25 | 18.3 | −0.5 |
| 12.50 | 8.2 | −0.1 |

The data demonstrate that there was no induction of apoptosis even at high concentrations of BT061.

Example 5

Complement Binding

In a flow cytometric test for binding of the complement factor C1qPBMCs have been isolated and incubated with BT061 (anti-CD4 mAb), followed by an incubation with purified recombinant C1q.

ATG (Tecelac) served as the positive control.

Detection was performed with a FITC labelled detection antibody against C1q. Results are shown in Table 7 below.

TABLE 7

| antibody concentration [µg/ml] | anti-CD4 mAb BT061 | Positive control |
|---|---|---|
| | Mean fluorescence intensity | |
| 150 | 199 | 782 |
| 75.0 | 200 | 766 |
| 37.5 | 205 | 732 |
| 18.8 | 217 | 672 |
| 9.4 | 210 | 541 |
| 4.7 | 198 | 491 |
| 2.3 | 199 | 371 |
| 1.2 | 193 | 302 |

The data show that no complement binding can be seen, even at high concentrations.

Example 6

Figure 7:
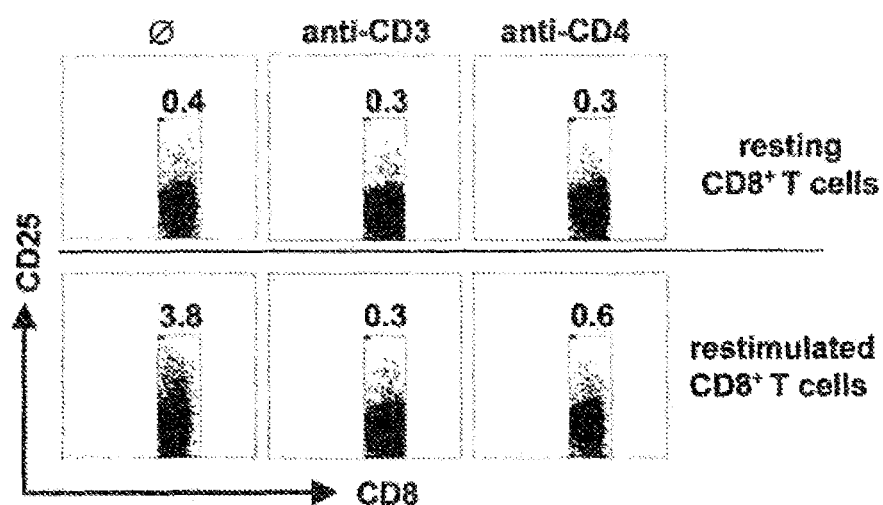
FIG. 7 shows that BT061 (anti-CD4 mAb)-activated CD25+ Tregs suppress cytokine synthesis and CD25 re-expression of CD8+ T cells. Top: CD4-activated CD25+ Tregs suppress cytokine synthesis of co-activated CD8+ T cells. Bottom: CD4-activated CD25+ Tregs suppress CD25 re-expression of CD8+ T cells. The dot plots show gated CD8+ T cells only. A representative result of three is shown. Numbers indicate percentages of positive cells.

CD4-Activated CD25+ Tregs Suppress Cytokine Synthesis and CD25 Re-Expression of CD8+ T Cells FIG. 7 shows that CD4-activated CD25+ Tregs suppress cytokine synthesis and CD25 re-expression of CD8+ T cells. Top: CD4-activated CD25+ Tregs suppress cytokine synthesis of co-activated CD8+ T cells.

Method

CD25+ Tregs were stimulated with/without anti-CD3 mAb or anti-CD4 mAb (B-F5, 1 µg/ml each) for 48 h. Thereafter, cells were co-cultured with irradiated T cell-depleted syngeneic PBMC and allogeneic CD8+ T cells (ratio 1:1). Production of cytokines was analysed on day 7. Alloreactive CD8+ T cells were re-stimulated with PHA/PMA for 5 h in presence of monensin, fixed and stained with anti-CD8 and cytokine-specific mAbs according to the respective manufacturer instruction (all BD PharMingen). Cytokine synthesis was analysed by flow cytometry drawing a gate on CD8+ lymphocytes. CD25 re-expression by CD8+ T cells was measured according to following procedure: CD25+ Tregs were stimulated with/without anti-CD3 mAb or anti-CD4 mAb (B-F5, 1 µg/ml each) for 48 h. Thereafter, cells were co-cultured with T cell-depleted syngeneic PBMC and allogeneic CD8+ T cells. On day 10, CD8+ T cells were re-stimulated with allogeneic CD3-depleted PBMC from the same donor as used for primary stimulation (ratio 1:1) and CD25 re-expression of CD8+ T cells was analyzed 24 h after re-stimulation flow cytometry.

Results

Activated CD25+ Tregs do not only suppress the proliferation of conventional T cells but also inhibit the production of cytokines and the ability of CD8+ T cells to express the a-chain of the IL-2 receptor, CD25. As shown in FIG. 7, CD4-activated CD25+ Tregs effectively inhibited IL-2 and IFN-γ production of alloreactive CD8+ T cells, similar to anti-CD3-stimulated CD25+ Tregs. Simultaneously, they rendered suppressed CD8+ T cells unable to express CD25 upon re-stimulation (FIG. 7). Taken together, these data demonstrate that CD4 stimulation fully activates the suppressive properties of CD25+ Tregs.

Example 7

Safety and Tolerability of Escalating Doses of BT061

A study was conducted to monitor the safety and tolerability of BT061 using escalating doses of the antibody in healthy male and female volunteers between the ages of ≥18 to ≤75 years.

Thirty volunteers received BT061 by intravenous administration in 10 dosage groups, with 3 volunteers per group. Further, 15 volunteers received BT061 by subcutaneous administration in 5 dosage groups also with 3 volunteers per group. The administration of BT061 intravenously is illustrated Table 8 below:

TABLE 8

Intravenous dose of BT061 Administration of BT061

| Total dose of BT061 mab | Volume of BT061-12.5 mg | Volume of BT061-25 mg | Volume of BT061-50 mg |
|---|---|---|---|
| 3.5 µg | 0.28 µl | — | — |
| 20 µg | 1.6 µl | — | — |
| 100 µg | 8 µl | — | — |
| 500 µg | 40 µl | — | — |
| 2.5 mg | 0.2 ml | — | — |
| 5 mg | 0.4 ml | — | — |
| 10 mg | 0.8 ml | — | — |
| 20 mg | — | 0.8 ml | — |
| 40 mg | — | — | 0.8 ml |
| 60 mg | 0.8 ml | — | 1 ml |

Each dose is diluted with 0.9% sodium chloride injection up to a total volume of 20 ml. The dose is administered as a single continuous intravenous infusion over 2 hours.

The administration of BT061 subcutaneously is illustrated in Table 9 below:

TABLE 9

Subcutaneous dose of BT061 Administration of BT061

| Total dose of BT061 mab | Volume of BT061-12.5 mg | Volume of BT061-25 mg | Volume of BT061-50 mg |
|---|---|---|---|
| 5 mg | 0.4 ml | — | — |
| 10 mg | 0.8 ml | — | — |
| 20 mg | — | 0.8 ml | — |
| 40 mg | — | — | 0.8 ml |
| 60 mg | — | — | 1 ml + 0.2 ml |

Each dose is injected as a single bolus injection.

The volunteers were assessed over a period of 3 months after the injection.

For subcutaneous application plasma samples were taken before administration and at 3, 6, 12, 24, 36, 48, 56, 72, 88, 96, 120, 144 and 168 hours after administration and on day 75.

For intravenous application, plasma samples were taken before administration and at 30 minutes, 1, 2, 3, 6, 12, 24, 36, 48, 72, 96, 120, 144 and 168 hours after administration.

The plasma samples were analyzed using standard ELISA methodology to establish cytokine levels. The relevant cytokines analyzed included: IFN-γ, TNF-α, IL-6, and IL-2.

The plasma samples were also analyzed using standard methods of flow cytometry to measure the number of CD4+ lymphocytes.

Results

It was found that intravenous and subcutaneous doses up to 60 mg were generally well tolerated.

Cytokine Levels

Induction of cytokine release is a common immediate complication occurring with the use of T cell interacting therapeutic antibodies, such as ATG, OKT3, CAMPATH-1H and humanized anti-CD3 mAbs (TRX4, Visilizumab and Teplizumab). The symptoms mainly include moderate fever, headaches and self-limiting gastrointestinal manifestations. Side effects correlated with cytokine induction after antibody administration require the application of additional drugs such as the antihistamine diphenhydramine hydrochloride and/or the anti-inflammatory agent ibuprofen.

With the use of OKT3 (muromonab-CD3), a murine CD3 specific therapeutic monoclonal antibody, there have even been deaths reported, and severe side effects limit the clinical use of this antibody mainly to immunosuppressed patients.

Although humanized FcR-non-binding CD3-specific monoclonal antibodies that are presently used in the clinic for the treatment of autoimmune disease (Teplizumab and TRX4) exhibit reduced side effects induced by T-cell activation and/or by activation of Fc receptor expressing cells after the first dose, as compared with FcR-binding CD3-specific antibodies such as OKT3, some degree of T-cell activation and activation of Fc receptor expressing cells is still observed that leads to cytokine release generally connected to cytokine dependent side effects.

In the present study it was surprisingly found that cytokine induction observed in healthy volunteers after intravenous or subcutaneous application of BT061 was low and transient as compared to anti-CD3 antibodies. Cytokine induction generally increased with increasing dosage. However, even at the highest doses of 40 to 60 mg cytokine induction is much lower than that seen with other T cell interacting monoclonal antibodies (FIGS. 8A and B).

Figures 8A, 8B:
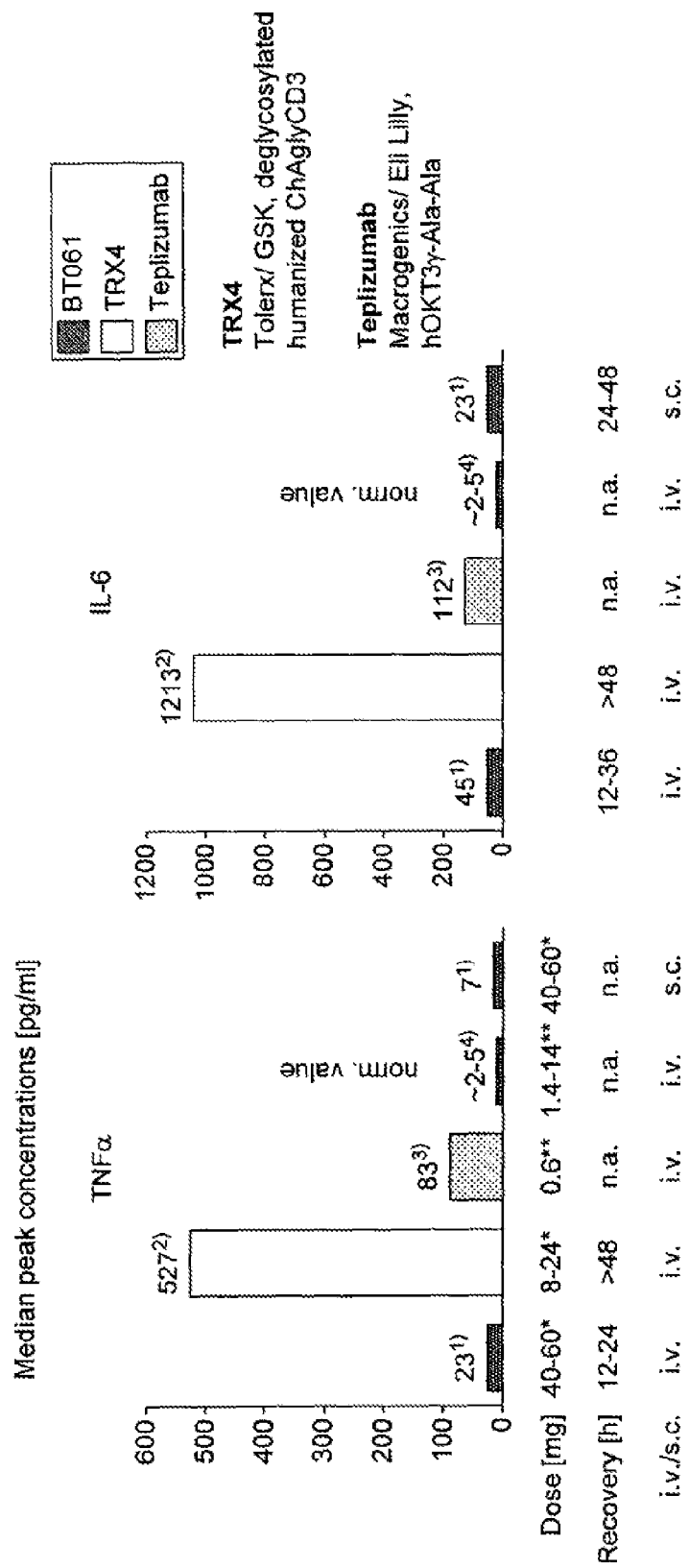
FIGS. 8A and 8B respectively show the TFNα and IL-6 release observed in a clinical trial with BT061 (single intravenous infusion or subcutaneous injection) in healthy volunteers in comparison to the levels reported with the anti-CD3 monoclonal antibodies. Dose levels and time to recovery are included in the figures. Results for TRX4 indicated in Figures as "2)" reported in Keymeulen et al., 2005 N. Engl. J. Med. Type 1 Diabetes patients. Results for Teplizumab indicated in Figures as "3)" reported in Herold et al., 2002 N. Engl. J. Med. Type I Diabetes patients. Normal values indicated in Figures as "4)" reported in Straub et al., 2007, Athr. & Rheumat. "*)" represents a single dose, "**)" represents a cumulative dose injected until peak concentration was reached.
Figure 9:
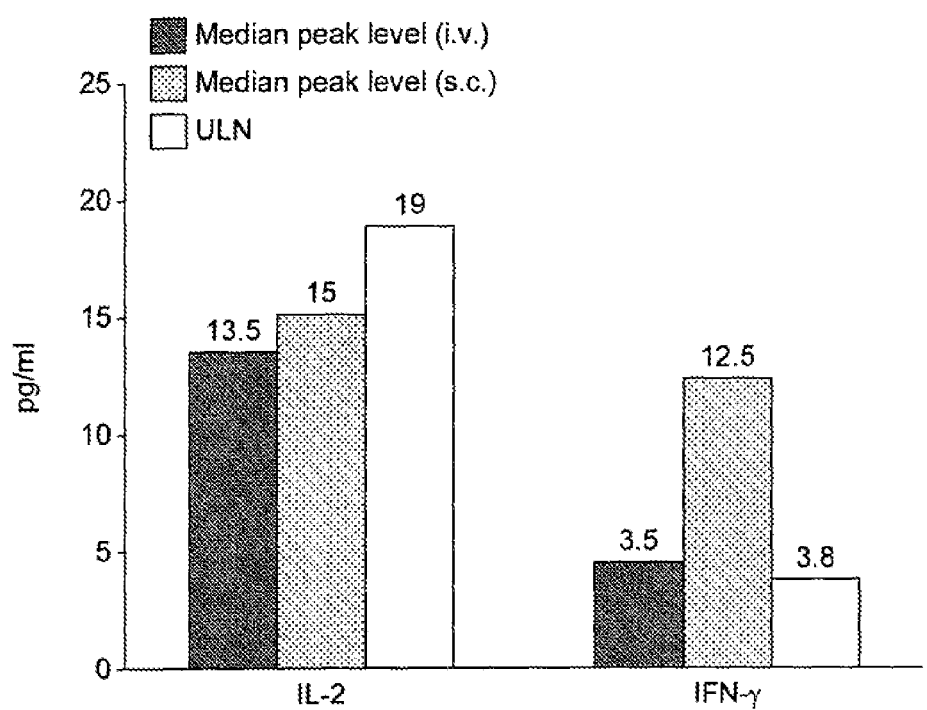
FIG. 9 shows IL-2 and IFN-γ plasma levels after administration of a single intravenous or subcutaneous dose of BT061 in healthy volunteers. ULN=upper limit of normal; LLN=lower limit of normal.

The median peak concentrations for the cytokines observed at any time point within 96 hours after administration using the highest doses (40 mg to 60 mg of BT061) are shown in FIGS. 8 and 9.

The median peak concentration for each cytokine is calculated as follows: The median of the highest cytokine concentrations observed after administration of the antibody.

FIGS. 8A and B show the TNFα and IL-6 release observed in healthy volunteers after intravenous or subcutaneous administration of BT061 in comparison to those released after administration of anti-CD3 monoclonal antibodies, Teplizumab and TRX4. The normal values of these cytokines were taken from Straub et al., (2007, Arthr. & Rheumat.). FIG. 9 shows the IL-2 and IFN-γ plasma levels after administration of intravenous or subcutaneous BT061. The median peak levels were calculated from the 40 and 60 mg dose group measured within 4 days after antibody injection. The upper limit of normal (ULN) was calculated based on cytokine levels measured in 39 healthy subjects, where ULN=mean value+2×standard deviation.

In comparison to Teplizumab and TRX4 (results taken from Herold et al., 2002, New Engl. J. Med, and Keymeulen et al., 2005 New Engl. J. Med, respectively) BT061 induced only marginal and transient cytokine release. TNF-α and IL-6 levels were slightly increased. FIG. 8 shows that the median peak values of IL-6 and TNFα cytokine levels detected in plasma after application of BT061 (40 and 60 mg) are lower than those seen after treatment with the CD3 specific therapeutic antibodies Teplizumab and TRX4.

Further, in contrast to the anti-CD3 mAbs, BT061 did not lead to substantially increased levels of IFN-γ and IL-2 (FIG. 9) as was reported for the application of TRX4 (Keymeulen et al. 2005).

CD4+ Lymphocytes

In addition, the trial also included a study of the numbers of CD4-positive lymphocytes in plasma samples collected.

The results of the intravenous administration are shown below in Tables 10, 11 and 12. Table 13 shows the results of the trial with subcutaneous administration. The results are shown graphically in FIGS. 10 and 11.

Tables 10A and 10B: CD4+ Cell Counts in Individual Healthy Volunteers after 3.5 mg to 2.5 mg Intravenous Administration of BT061

TABLES 10A and B

| TIME | DOSE | | | | | |
|---|---|---|---|---|---|---|
| | 3.5 µg | 3.5 µg | 3.5 µg | 20 µg | 20 µg | 20 µg |
| Predose | 998 | 878 | 1025 | 955 | 1209 | 666 |
| 3 h | 1098 | 746 | 1020 | 708 | 1121 | 642 |
| 6 h | 922 | 710 | 1063 | 746 | 1091 | 590 |
| 12 h | 898 | 1183 | 942 | 1016 | 1667 | 1055 |
| 24 h | 868 | 825 | 769 | 699 | 1043 | 517 |
| 36 h | 948 | 1035 | 1148 | 861 | 1549 | 836 |
| 48 h | 798 | 542 | 834 | 566 | 1119 | 711 |
| 72 h | 798 | 626 | 766 | 622 | 942 | 575 |
| 96 h | 469 | 715 | 838 | 583 | 978 | 531 |
| 120 h | 736 | 643 | 843 | 604 | 942 | 472 |
| 144 h | 663 | 593 | 766 | 635 | 1200 | 510 |
| 168 h | 753 | 576 | 695 | 616 | 1012 | 505 |
| day 14 | 716 | 615 | 625 | 696 | 867 | 645 |
| day 21 | 941 | 378 | 707 | 637 | 971 | 633 |
| day 28 | 821 | 569 | 840 | 652 | 863 | 649 |
| day 42 | 922 | 442 | 784 | 676 | 1044 | 700 |
| day 56 | 573 | 597 | 828 | 839 | 871 | 553 |
| day 75 | 1821 | 512 | 692 | 659 | 1058 | 553 |
| day 90 | | | | | | |
| minimum cell count (72 h to day 75) | 469 | 378 | 625 | 583 | 863 | 472 |
| Maximum Reduction of CD4+ cells (%) | 53.0 | 56.9 | 39.0 | 39.0 | 28.6 | 29.1 |

| TIME | DOSE | | | | | | | |
|---|---|---|---|---|---|---|---|---|
| | 100 µg | 100 µg | 100 µg | 500 µg | 500 µg | 500 µg | 2.5 mg | 2.5 mg |
| Predose | 1164 | 800 | 543 | 759 | 493 | 1240 | 891 | 782 |
| 3 h | 452 | 791 | 319 | 111 | 566 | 1058 | 392 | 461 |
| 6 h | 353 | 627 | 314 | 805 | 381 | 1115 | 487 | 512 |
| 12 h | 465 | 1065 | 477 | 955 | 643 | 1505 | 669 | 881 |
| 24 h | 399 | 606 | 347 | 687 | 439 | 1017 | 521 | 701 |
| 36 h | 559 | 1016 | 485 | 869 | 688 | 1542 | 976 | 1207 |
| 48 h | 384 | 644 | 413 | 730 | 509 | 1108 | 574 | 815 |
| 72 h | 400 | 749 | 503 | 696 | 484 | 969 | 537 | 689 |
| 96 h | 475 | 698 | 400 | 800 | 390 | 1026 | 499 | 785 |
| 120 h | 401 | 650 | 511 | 830 | 488 | 1168 | 501 | 782 |
| 144 h | 372 | 573 | 432 | 705 | 394 | 953 | 518 | 745 |
| 168 h | 348 | 646 | 426 | 740 | 475 | 1073 | 568 | 773 |
| day 14 | 400 | 771 | 451 | 713 | 600 | 1398 | 663 | 883 |
| day 21 | 391 | 805 | 404 | 651 | 533 | 1241 | 530 | 758 |
| day 28 | 497 | 775 | 503 | 752 | 445 | 1109 | 590 | 914 |
| day 42 | 569 | 758 | 455 | 700 | 617 | 1120 | 770 | 901 |
| day 56 | 489 | 607 | 441 | 674 | 616 | 1311 | 634 | 1017 |
| day 75 | 466 | 735 | 459 | 645 | 522 | 1026 | 731 | 1032 |
| day 90 | | | | | | | | |
| minimum cell count (72 h to day 75) | 348 | 573 | 400 | 645 | 390 | 953 | 499 | 689 |
| Maximum Reduction of CD4+ cells (%) | 70.1 | 28.4 | 26.3 | 15.0 | 20.9 | 23.1 | 44.0 | 11.9 |

TABLE 11

CD4+ cell counts in individual healthy volunteers
after 2.5 mg to 20 mg intravenous administration of BT061

| TIME | DOSE | | | | | | | |
|---|---|---|---|---|---|---|---|---|
| | 2.5 mg | 5 mg | 5 mg | 5 mg | 10 mg | 10 mg | 10 mg | 20 mg |
| Predose | 1080 | 1116 | 623 | 1160 | 840 | 835 | 1281 | 700 |
| 3 h | 488 | 313 | 108 | 111 | 104 | 143 | 132 | 63 |
| 6 h | 514 | 445 | 164 | 246 | 122 | 82 | 120 | 110 |
| 12 h | 699 | 763 | 346 | 573 | 297 | 285 | 366 | 199 |
| 24 h | 726 | 617 | 282 | 539 | 470 | 496 | 772 | 351 |
| 36 h | 985 | 1102 | 505 | 721 | 414 | 985 | 1417 | 677 |
| 48 h | 738 | 807 | 390 | 687 | 388 | 794 | 942 | 493 |
| 72 h | 711 | 736 | 419 | 700 | 440 | 830 | 919 | 504 |
| 96 h | 680 | 791 | 395 | 806 | 516 | 641 | 918 | 538 |
| 120 h | 649 | 669 | 438 | 750 | 543 | 674 | 1002 | 558 |
| 144 h | 662 | 723 | 407 | 676 | 448 | 549 | 942 | 579 |
| 168 h | 579 | 111 | 309 | 652 | 473 | 525 | 876 | 510 |
| day 14 | 726 | 692 | 354 | 475 | 357 | 701 | 908 | 484 |
| day 21 | 601 | 811 | 480 | 514 | 481 | 654 | 978 | 618 |
| day 28 | 874 | 681 | 339 | 602 | 414 | 755 | 887 | 496 |
| day 42 | 923 | 843 | 300 | 694 | 507 | 614 | 889 | 639 |
| day 56 | 847 | | 450 | 571 | 551 | 805 | 1006 | 420 |
| day 75 | 1239 | | 365 | 627 | 685 | 853 | 1080 | 537 |
| day 90 | | 721 | | | | | | |
| minimum cell count (72 h to day 75) | 579 | 669 | 300 | 475 | 357 | 525 | 876 | 420 |
| Maximum Reduction of CD4+ cells (%) | 46.4 | 40.1 | 51.8 | 59.1 | 57.5 | 37.1 | 31.6 | 40.0 |

Figure 10:
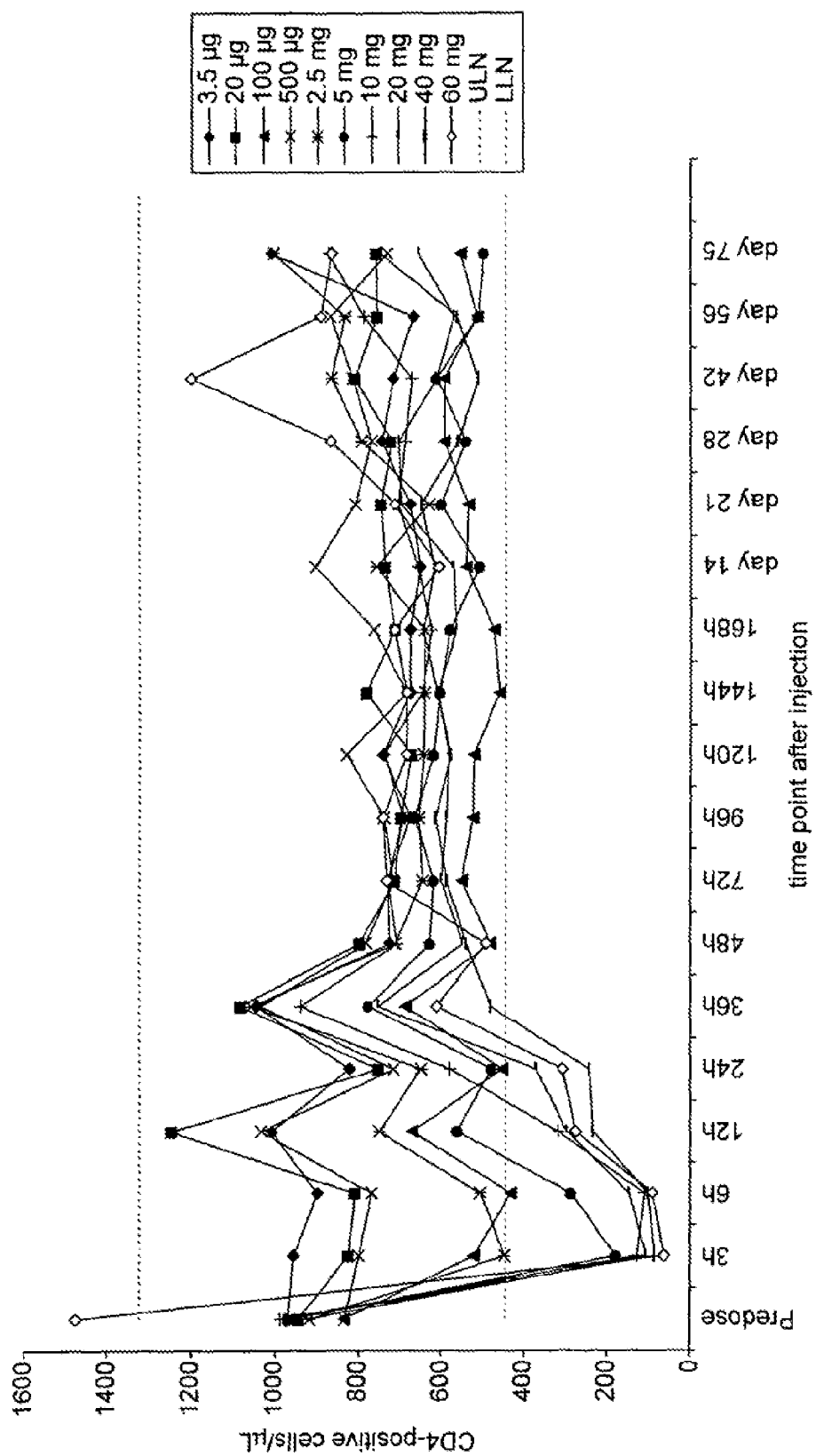
FIG. 10 shows a kinetic of CD4 cell counts (cells per ml of plasma) in volunteers treated with a single intravenous dose of BT061. Mean values of 3 patients per dose group are shown. Dotted lines indicate the upper limit of normal (ULN) and the lower limit of normal (LLN).

In particular, FIG. 10 shows the CD4 cell counts (cells per ml plasma) in volunteers treated with the single intravenous dose of BT061. The data points represent the mean values of the 3 patients in each dose group. Dotted lines indicate the upper limit of normal (ULN) and the lower limit of normal (LLN). The ULN and the LLN (mean value+(or −) the standard deviation) were calculated, based on cell counts from healthy volunteers, as 443 CD4 cells per µl (lower limit of normal; LLN) and 1324 CD4 cells per µl (upper limit of normal; ULN).

Figure 11:
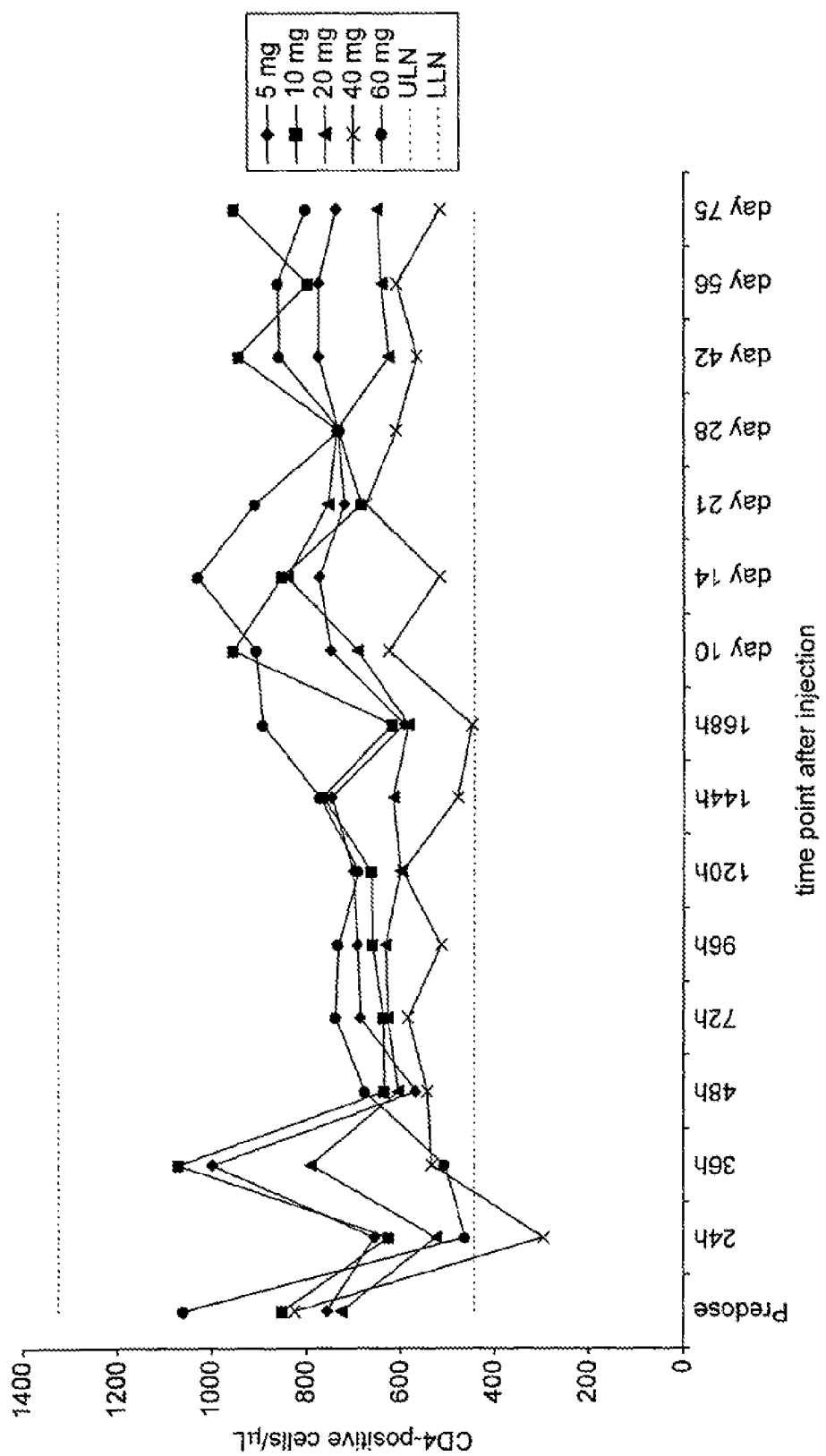
FIG. 11 shows a kinetic of CD4 cell counts (cells per ml of plasma) in volunteers treated with a single subcutaneous dose of BT061. Mean values of 3 patients per dose group are shown. Dotted lines indicate the upper limit of normal (ULN) and the lower limit of normal (LLN).
Figure 12A:
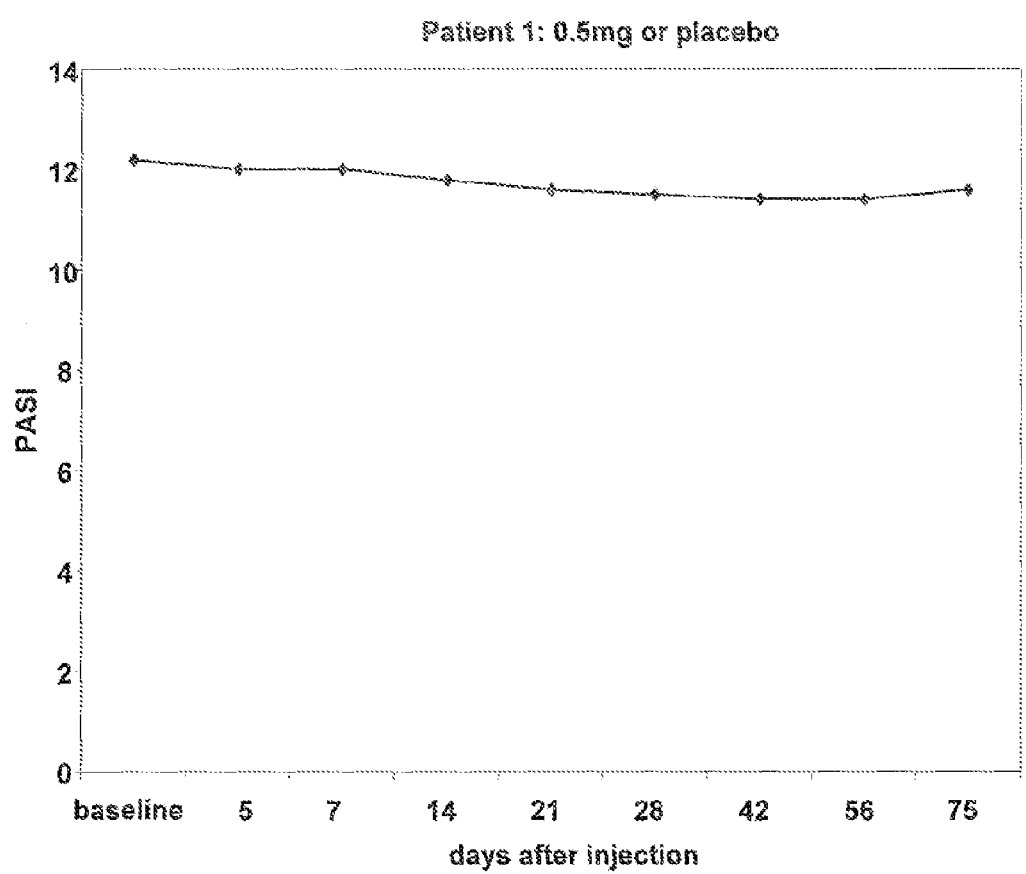
FIG. 12 parts A to H provide graphs showing data from the clinical trials with psoriasis patients of dose group I as described in Example 8, in which patients are treated with a 0.5 mg intravenous injection of BT061 or a placebo. Parts A to H of FIG. 8 provide graphs of the PASI scores of patients 1 to 8 of dose group I, respectively.
Figure 12B:
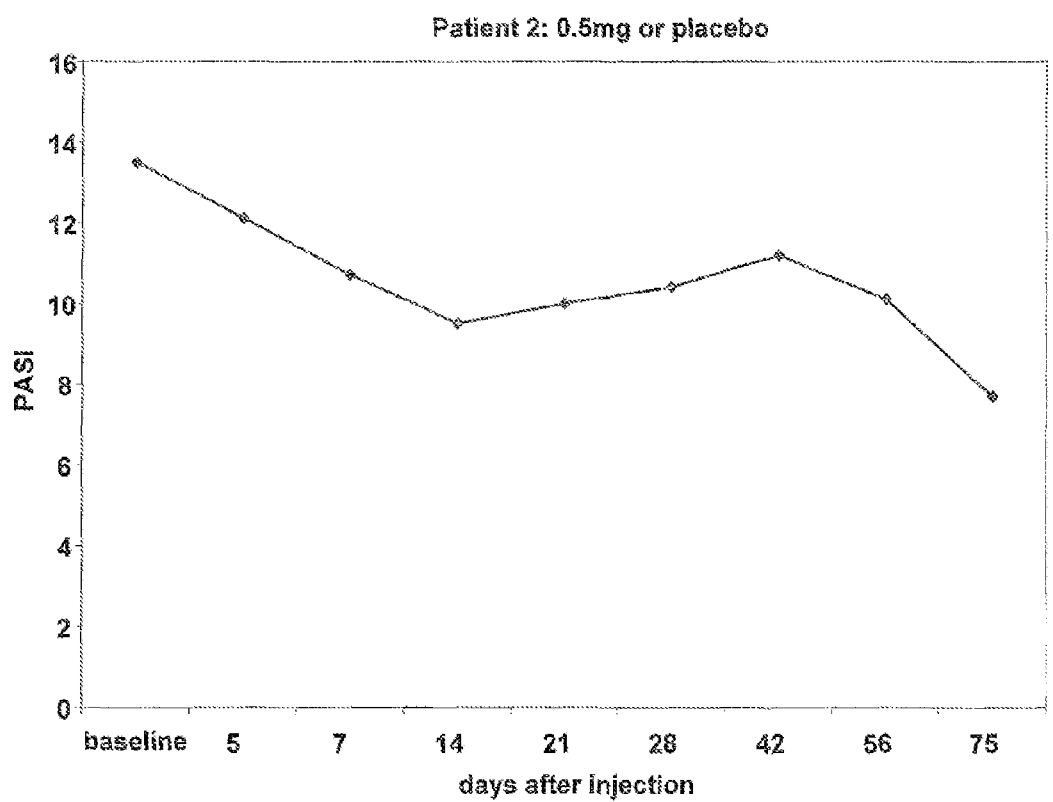
Figure 12C:
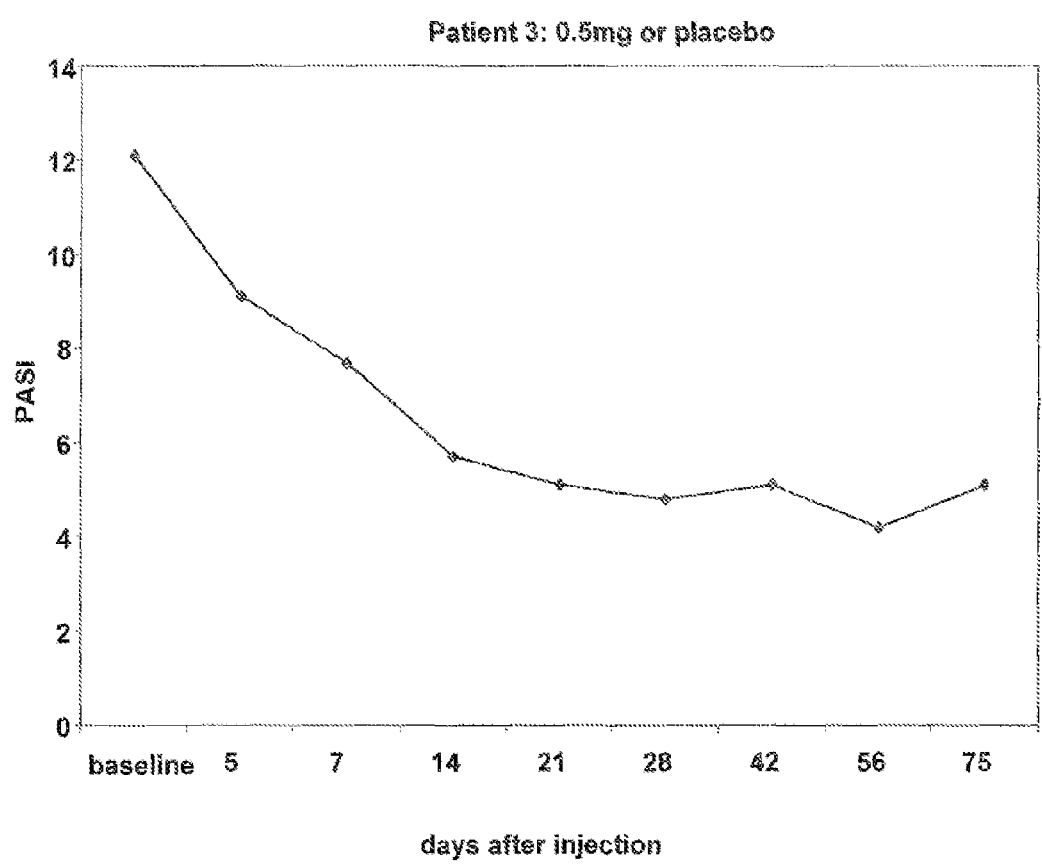
Figure 12D:
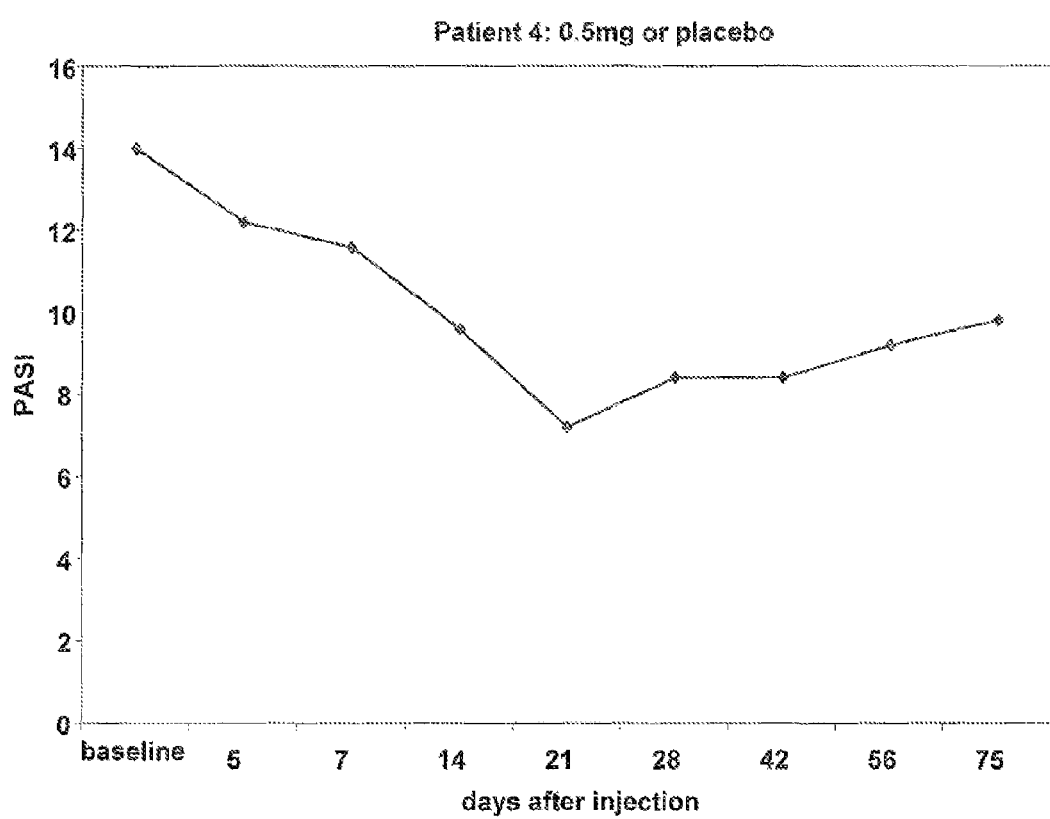
Figure 12E:
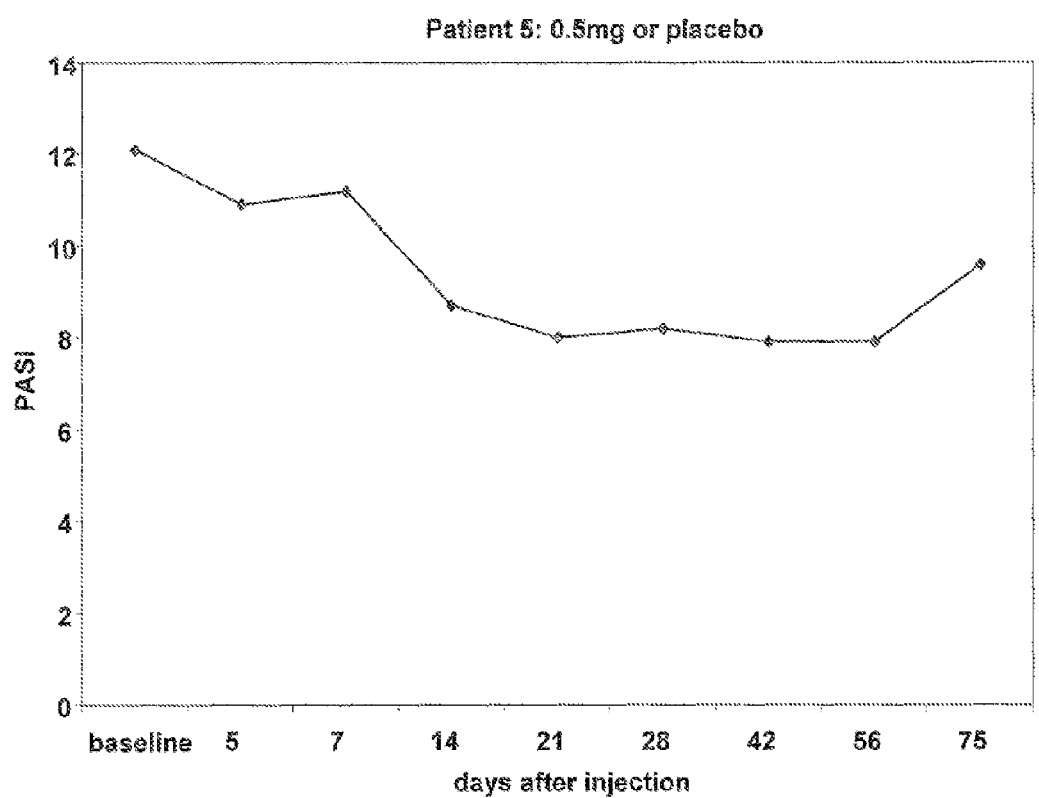
Figure 12F:
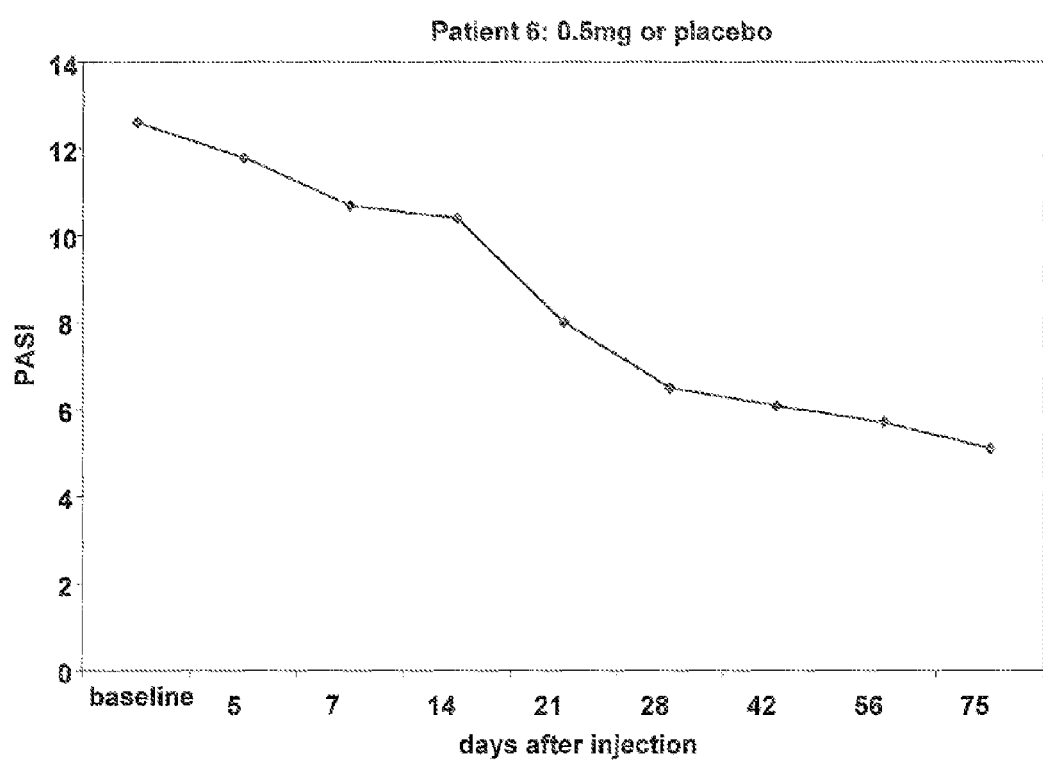
Figure 12G:
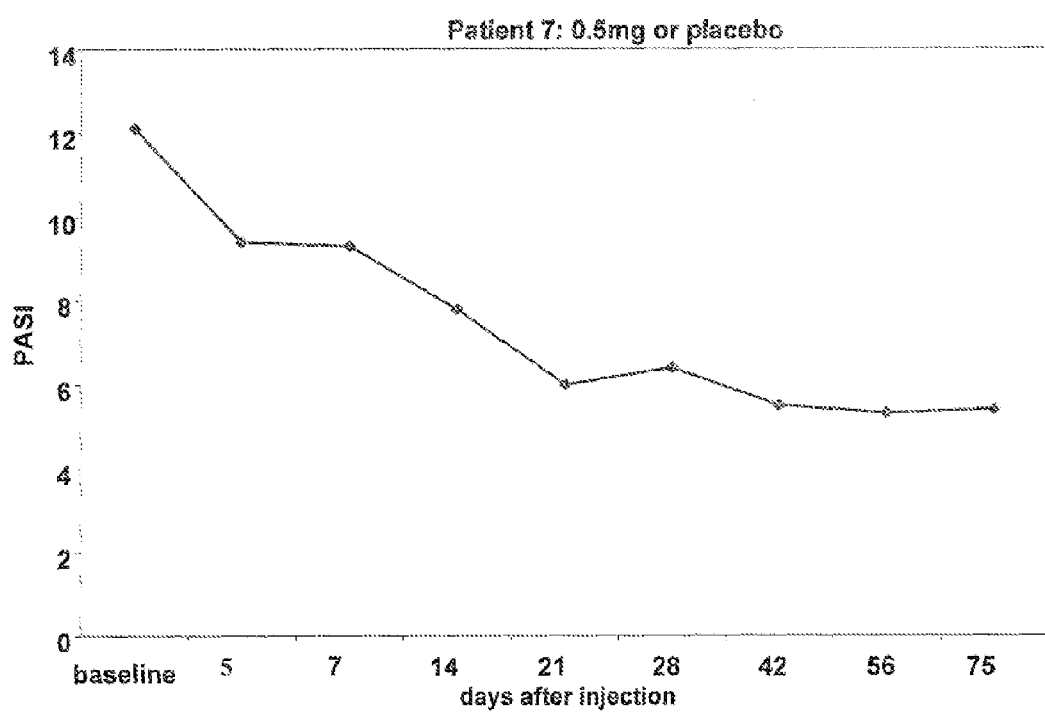
Figure 12H:
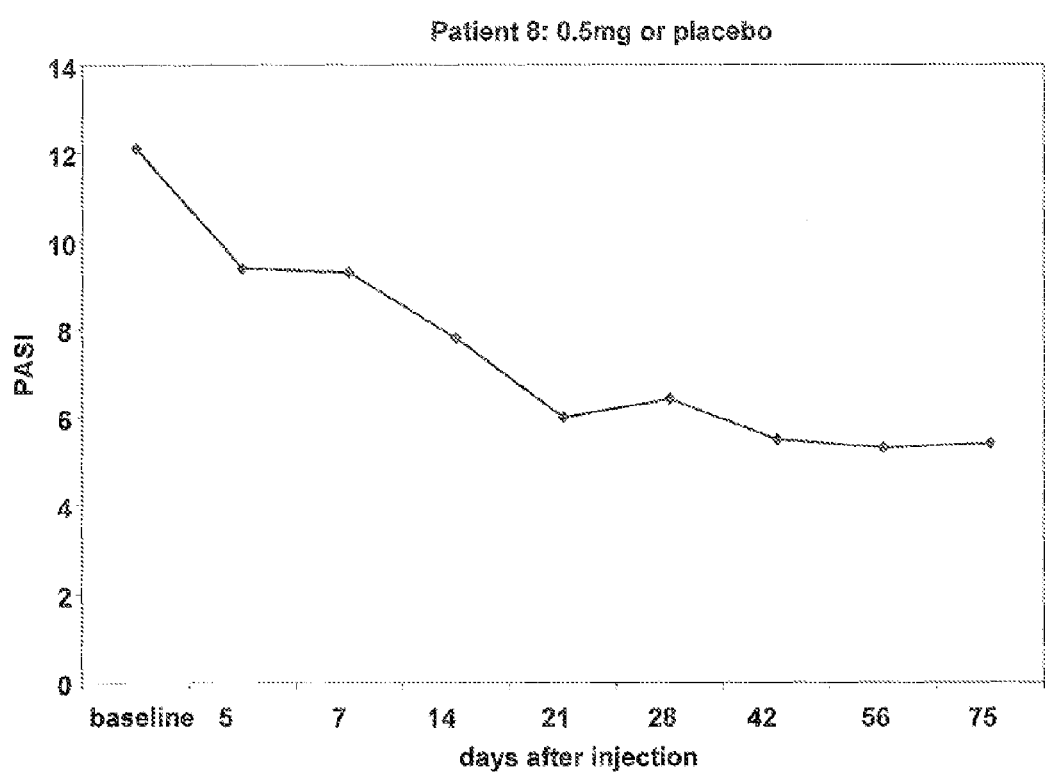
Figure 13A:
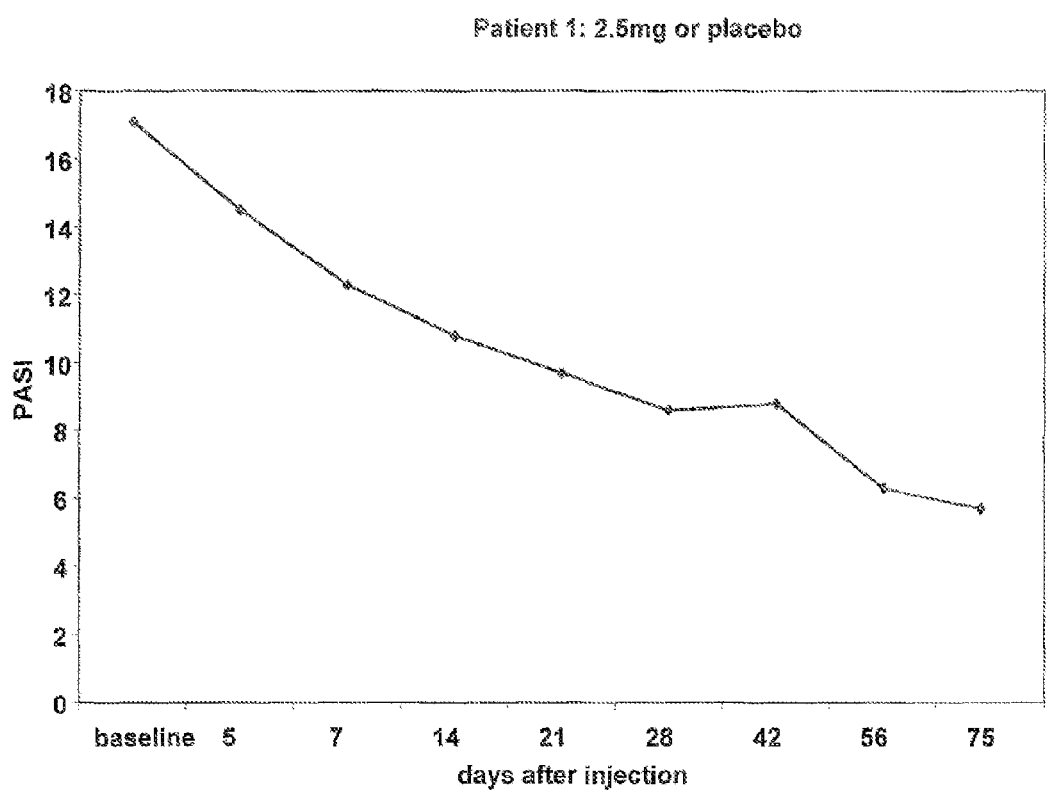
FIG. 13 parts A to H provide graphs showing data from the clinical trials with psoriasis patients of dose group II as described in Example 8, in which patients are treated with a 2.5 mg intravenous injection of BT061 or a placebo. Parts A to H of FIG. 9 provide graphs of the PASI scores of patients 1 to 8 of dose group II, respectively.
Figure 13B:
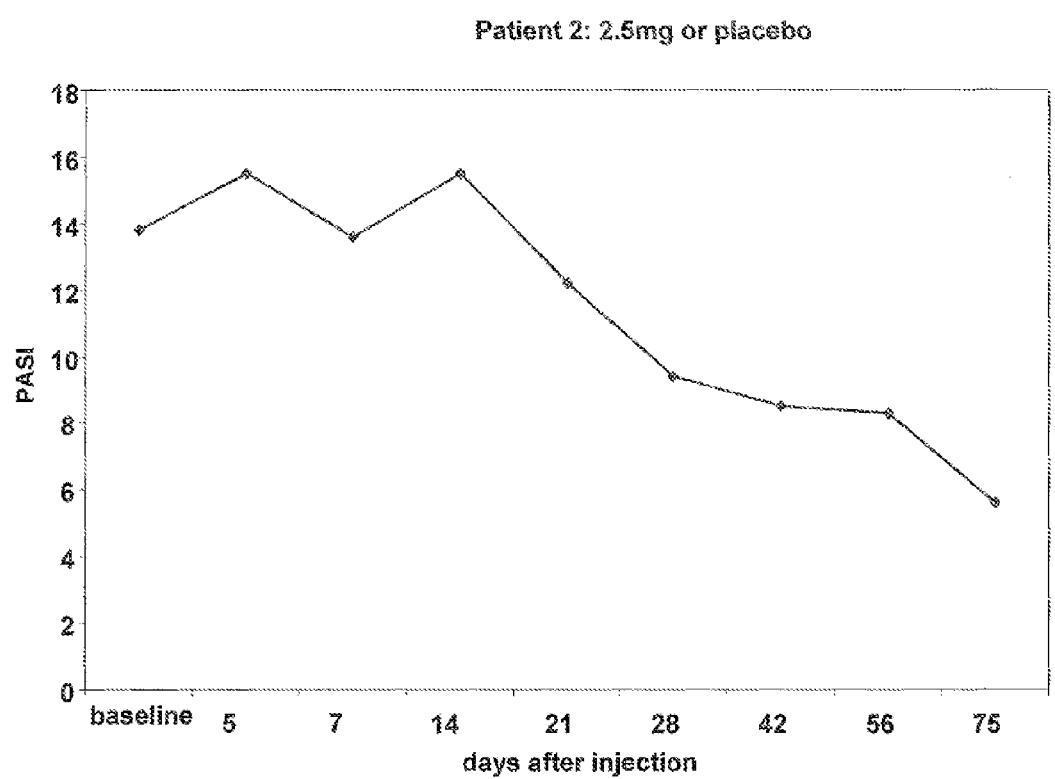
Figure 13C:
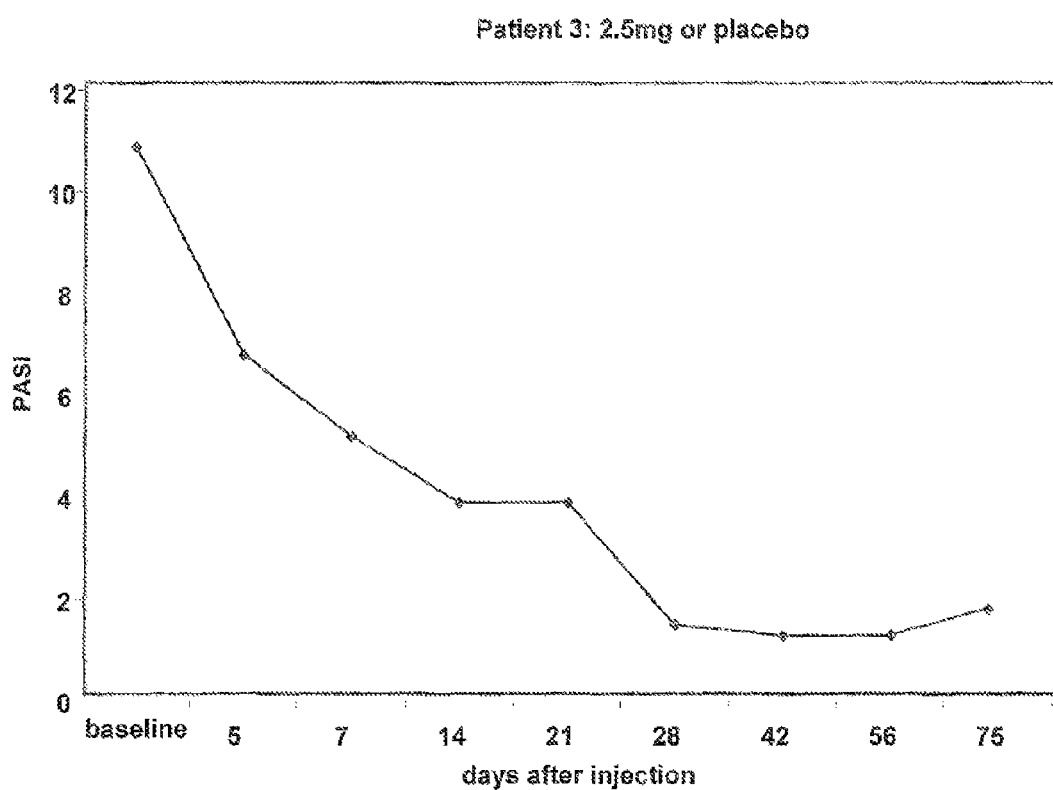
Figure 13D:
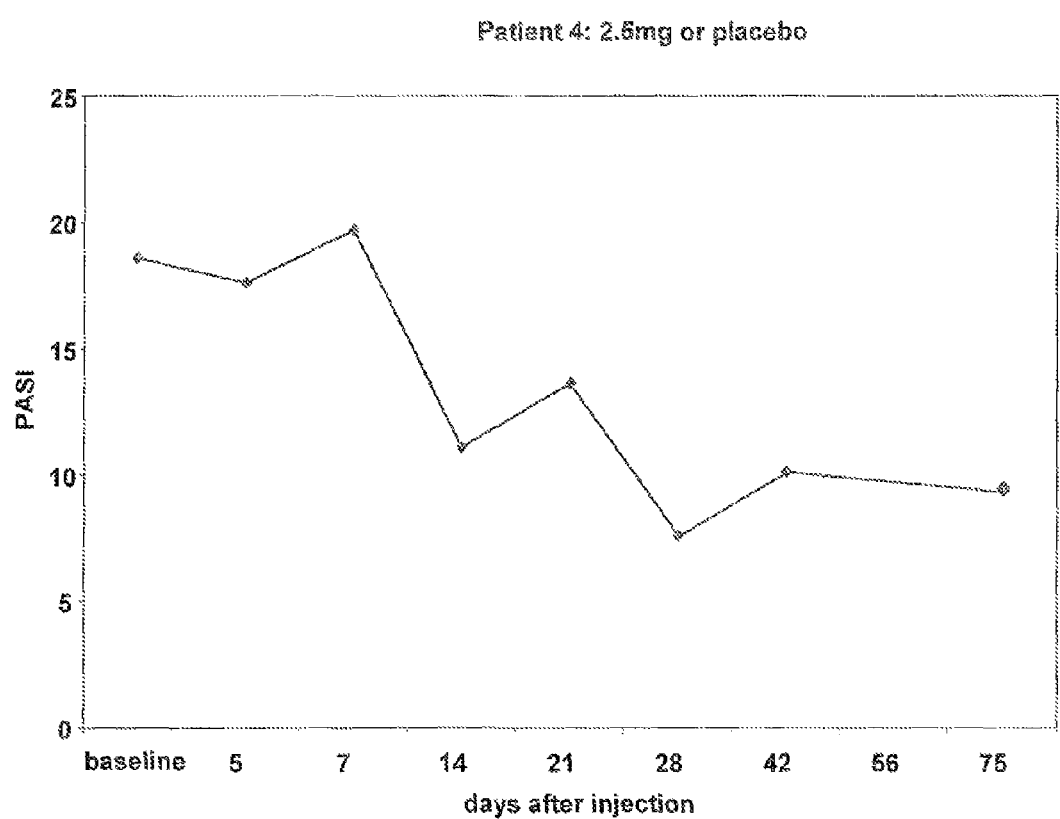
Figure 13E:
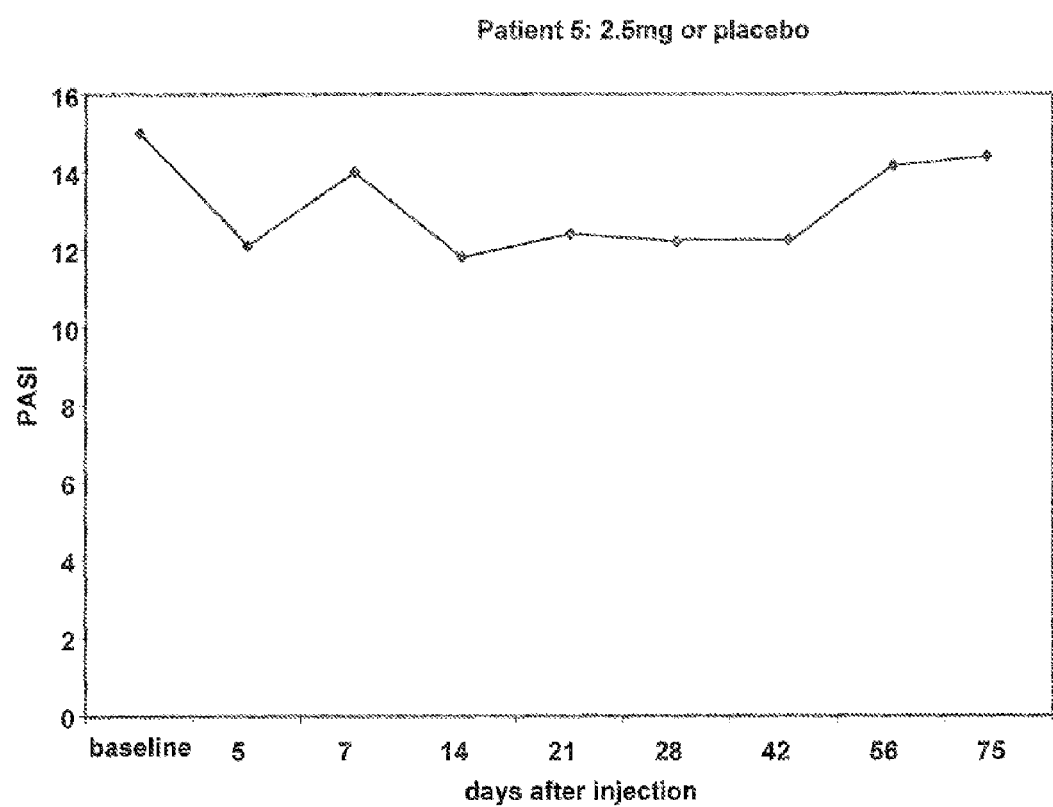
Figure 13F:
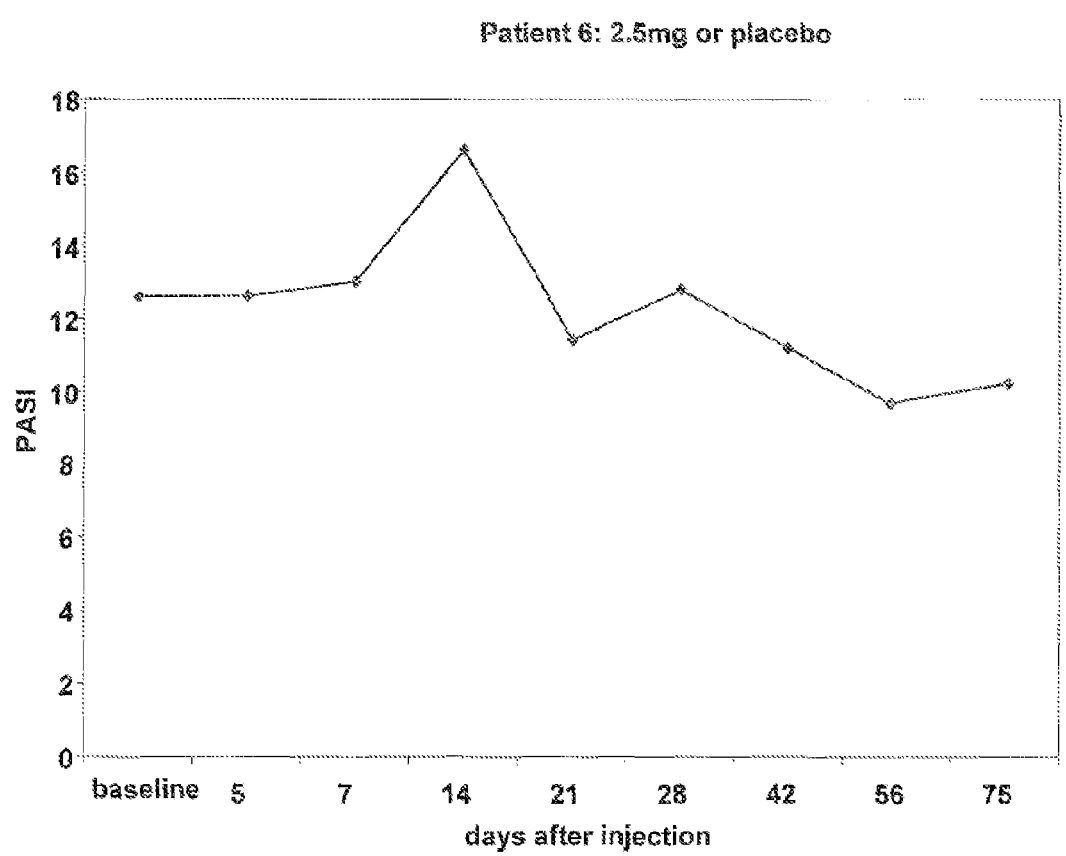
Figure 13G:
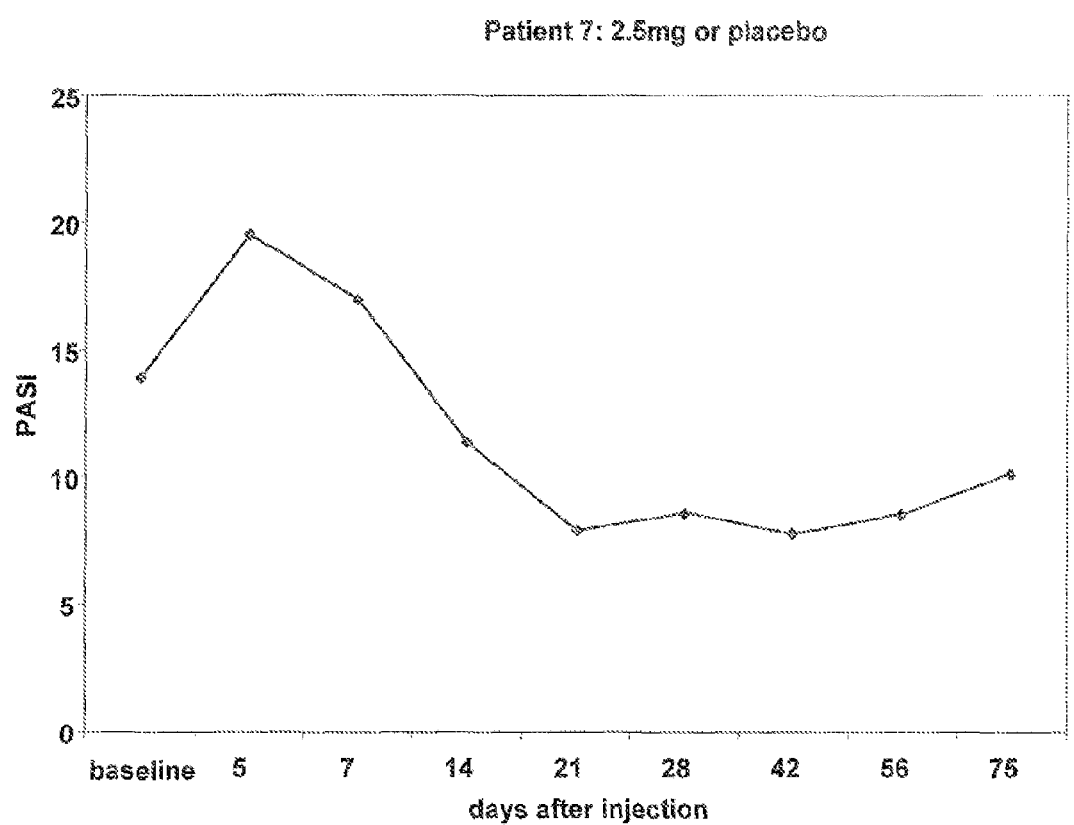
Figure 13H:
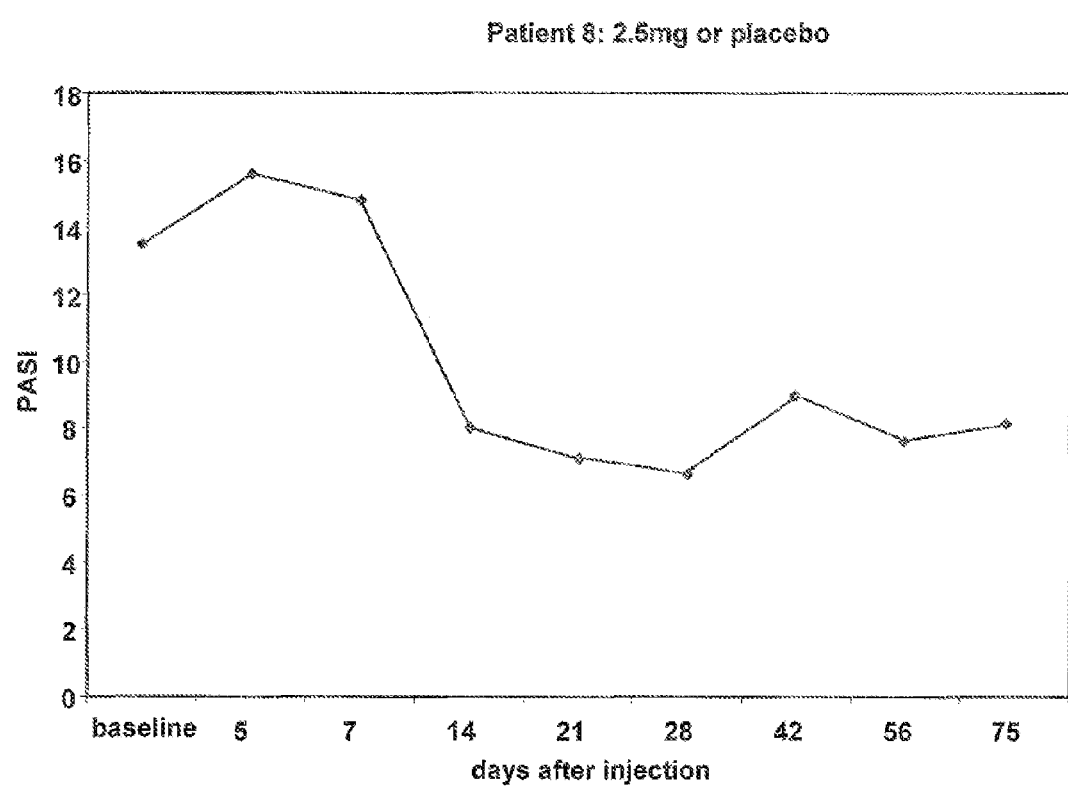

FIG. 11 shows the CD4 cell counts (cells per ml plasma) in volunteers treated with the single subcutaneous dose of BT061. As with FIG. 10, the data points represent the mean values of the 3 patients in each dose group. Dotted lines indicate the upper limit of normal (ULN) and the lower limit of normal (LLN).

TABLE 12

CD4+ cell counts in individual healthy volunteers
after 20 mg to 60 mg intravenous administration of BT061

| TIME | DOSE | | | | | | | |
|---|---|---|---|---|---|---|---|---|
| | 20 mg | 20 mg | 40 mg | 40 mg | 40 mg | 60 mg | 60 mg | 60 mg |
| Predose | 843 | 1233 | 1152 | 789 | 976 | 900 | 989 | 2539 |
| 3 h | 69 | 186 | 72 | 137 | 48 | 63 | 55 | 71 |
| 6 h | 83 | 245 | 87 | 147 | 69 | 81 | 78 | 109 |
| 12 h | 214 | 469 | 262 | 221 | 212 | 360 | 276 | 182 |
| 24 h | 266 | 490 | 208 | 222 | 292 | 315 | 285 | 313 |
| 36 h | 562 | 1019 | 489 | 475 | | 707 | 561 | 569 |
| 48 h | 359 | 792 | 460 | 455 | 703 | 413 | 500 | 565 |
| 72 h | 392 | 909 | 591 | 545 | 625 | 709 | 688 | 806 |
| 96 h | 468 | 755 | 567 | 545 | 733 | 717 | 737 | 774 |
| 120 h | 391 | 795 | 578 | 517 | 636 | 718 | 685 | 646 |
| 144 h | 347 | 897 | 548 | 523 | 760 | 714 | 732 | 606 |
| 168 h | 331 | 853 | 630 | 577 | 720 | 656 | 822 | 662 |
| day 14 | 334 | 899 | 683 | 495 | 675 | 851 | 546 | 423 |
| day 21 | 396 | 1077 | 744 | 487 | 711 | 627 | 639 | 867 |
| day 28 | 579 | 1030 | 637 | 458 | 582 | 466 | 757 | 1376 |
| day 42 | 346 | 847 | 439 | 472 | 619 | 1179 | 814 | 1607 |
| day 56 | 337 | 947 | 556 | 557 | 570 | 686 | 686 | 1298 |
| day 75 | 597 | 824 | 986 | 440 | 813 | 648 | 748 | 1199 |
| day 90 | | | | | | | | |

TABLE 12-continued

CD4+ cell counts in individual healthy volunteers after 20 mg to 60 mg intravenous administration of BT061

| TIME | DOSE | | | | | | | |
|---|---|---|---|---|---|---|---|---|
| | 20 mg | 20 mg | 40 mg | 40 mg | 40 mg | 60 mg | 60 mg | 60 mg |
| minimum cell count (72 h to day 75) | 331 | 755 | 439 | 440 | 570 | 466 | 546 | 423 |
| Maximum Reduction of CD4+ cells (%) | 60.7 | 38.8 | 61.9 | 44.2 | 41.6 | 48.2 | 44.8 | 83.3 |

Tables 13A and B: CD4+Cell Counts in Individual Healthy Volunteers after Subcutaneous Application of BT061

TABLE 13A

| TIME | DOSAGE | | | | | |
|---|---|---|---|---|---|---|
| | 5 mg | 5 mg | 5 mg | 10 mg | 10 mg | 10 mg |
| Predose | 1053 | 553 | 663 | 962 | 697 | 891 |
| 24 h | 858 | 402 | 707 | 640 | 623 | 615 |
| 36 h | 1131 | 916 | 946 | 1232 | 955 | 1019 |
| 48 h | 625 | 526 | 550 | 610 | 757 | 537 |
| 72 h | 814 | 661 | 580 | 589 | 709 | 610 |
| 96 h | 799 | 582 | 694 | 666 | 732 | 579 |
| 120 h | 823 | 566 | 712 | 653 | 673 | 659 |
| 144 h | 890 | 543 | 809 | 744 | 767 | 784 |
| 168 h | 894 | 450 | 437 | 686 | 655 | 516 |
| day 10 | 951 | 606 | 690 | 1213 | 724 | 928 |
| day 14 | 719 | 647 | 948 | 969 | 724 | 859 |
| day 21 | 859 | 552 | 750 | 655 | 708 | 685 |
| day 28 | 894 | 546 | 758 | 778 | 653 | 766 |
| day 42 | 854 | 461 | 1009 | 1235 | 805 | 785 |
| day 56 | 806 | 560 | 958 | 977 | 665 | 753 |
| day 75 | 852 | 592 | 111 | 1268 | 679 | 906 |
| minimum cell count (72 h to day 75) | 719 | 450 | 437 | 589 | 653 | 516 |
| Maximum Reduction of CD4+ cells (%) | 31.7 | 18.6 | 34.1 | 38.8 | 6.3 | 42.1 |

TABLE 13B

| TIME | DOSAGE | | | | | | | | |
|---|---|---|---|---|---|---|---|---|---|
| | 20 mg | 20 mg | 20 mg | 40 mg | 40 mg | 40 mg | 60 mg | 60 mg | 60 mg |
| Predose | 863 | 692 | 621 | 689 | 946 | 840 | 1114 | 719 | 1345 |
| 24 h | 537 | 535 | 500 | 177 | 326 | 379 | 580 | 470 | 333 |
| 36 h | 762 | 666 | 944 | 268 | 463 | 870 | 503 | 527 | 487 |
| 48 h | 628 | 599 | 587 | 354 | 586 | 686 | 739 | 735 | 551 |
| 72 h | 700 | 587 | 596 | 299 | 719 | 734 | 860 | 813 | 539 |
| 96 h | 643 | 665 | 589 | 283 | 605 | 653 | 852 | 743 | 608 |
| 120 h | 642 | 528 | 633 | 323 | 835 | 629 | 873 | 639 | 555 |
| 144 h | 603 | 620 | 627 | 239 | 626 | 568 | 801 | 924 | 591 |
| 168 h | 620 | 550 | 581 | 262 | 515 | 569 | 1010 | 843 | 820 |
| day 10 | 683 | 616 | 778 | 354 | 715 | 809 | 757 | 1123 | 836 |
| day 14 | 843 | 642 | 1033 | 307 | 705 | 541 | 1198 | 1359 | 527 |
| day 21 | 904 | 605 | 752 | 293 | 1097 | 630 | 1074 | 901 | 750 |
| day 28 | 757 | 680 | 768 | 298 | 861 | 667 | | 880 | 578 |
| day 42 | 775 | 469 | 634 | 308 | 678 | 709 | 568 | 1149 | 854 |
| day 56 | 801 | 589 | 531 | 342 | 541 | 948 | 1126 | 945 | 505 |
| day 75 | 714 | 688 | 551 | 340 | 551 | 659 | | | |
| minimum cell count (72 h to day 75) | 603 | 469 | 531 | 239 | 515 | 541 | 568 | 639 | 505 |
| Maximum Reduction of CD4+ cells (%) | 30.1 | 32.2 | 14.5 | 65.3 | 45.6 | 35.6 | 49.0 | 11.1 | 62.5 |

Many CD4 specific monoclonal antibodies known in the art (such as those reviewed in Strand et al., 2007) achieve immuno-suppression via CD4-positive lymphocyte depletion. The drawback of these antibodies is that treated individuals become immuno-compromised, and are susceptible to other infections.

In contrast this study showed that BT061 induced no massive long-lasting depletion of CD4-positive cells. However, a transient decline of CD4-positive lymphocytes was observed with a recovery to norm values in the peripheral blood within 72 h after administration of the antibody.

At the 72 h time point after application of BT061, CD4 cell counts in four volunteers of the intravenous dose groups showed CD4 levels that were below these norm values as follows: 1 volunteer of the 100 µg intravenous dose: 400 CD4 cells per µl; 1 volunteer of the 5 mg group: 419 CD4 cells per µl; 1 volunteer of the 10 mg group: 440 CD4 cells per µl; and 1 volunteer of the 20 mg group: 392 CD4 cells per µl.

However, these values were only slightly below norm values. CD4 cell counts in the remaining 26 volunteers of the intravenous dose groups were within the norm values 72 hours after administration of BT061.

In the subcutaneous dose groups, after 72 h, only one out of 15 volunteer showed CD4 cell counts below norm values.

In conclusion, in contrast to depleting CD4 specific mAbs, even at high doses BT061 only induced a transient decline of CD4-positive cells followed by a general recovery. From the transient decline and rapid general recovery it is concluded that a transient redistribution of the CD4-positive cells has taken place, rather than depletion of these cells.

Thus the data supports the use of BT061 as an agent to be administered in a plurality of doses over a long time period.

Example 8

Clinical Trial of BT061 in Patients with Moderate to Severe Chronic Psoriasis

The ability of hB-F5 BT061 to treat an autoimmune disease is being tested on 56 patients suffering from moderate to severe chronic psoriasis. The trial comprises a single dose escalation study to assess the safety and efficacy of hB-F5.

The conditions of the trial are as follows:

The 56 patients are divided into seven dose groups, each group comprising eight individuals. Five dose groups (dose groups I to V) are to receive the antibody or placebo by intravenous administration and two dose groups (dose groups VI and VII) are to receive the antibody or placebo via subcutaneous administration. Two patients in each dose group receive a placebo, while the remaining six patients in each dose group receive a dose of BT061. In dose group I the six patients receive 0.5 mg of intravenous BT061. In dose groups II to V the six patients receive 2.5 mg, 5 mg, 10 mg, or 20 mg of BT061, respectively. In dose groups VI and VII where the administration is subcutaneous, the six patients receive 12.5 mg or 25 mg of BT061, respectively.

For intravenous administration the antibody/placebo is to be infused in the forearm vein according to medically accepted procedures. In the present case the total volume is administered as a single continuous intravenous infusion over a period of 2 hours via a perfusor (Fresenius Pilot C, Fresenius AG, Germany). Each dose of the antibody is diluted with a 0.9% sodium chloride injection (B. Braun Melsungen AG, Germany) up to a total volume of 20 ml.

For subcutaneous administration the antibody is to be administered as a single subcutaneous injection. The same procedure applies for the placebo.

The level of psoriasis exhibited by each patient is recorded using the Psoriasis Area and Severity Index (PASI) score. As described above higher PASI scores corresponds to a higher level of psoriasis. Patients enrolled onto the trial have a moderate to severe chronic psoriasis, i.e. a PASI score of 10 or above.

The patient's PASI score is assessed before the trial to provide a "baseline" value at day 0, and repeatedly during the trial at days 5, 7, 14, 21, 28, 42, 56 and 75.

Dose Group I

Six patients from dose group I received a single intravenous application of 0.5 mg of BT061, while two patients from dose group 1 received the placebo. The dose per weight and the dose per body surface area (BSA) for each patient are shown in Table 14. Body surface area was calculated according to the Mosteller formula described herein.

The PASI scores for the patients in dose group I are shown in Table 14 together with the percentage improvement in the PASI score from the baseline.

Dose Group II

Six patients from dose group II received a single intravenous injection of 2.5 mg of BT061 while two patients from dose group 2 received the placebo. The dose per weight and the dose per body surface area (BSA) for each patient is shown in Table 15.

The PASI scores for the patients in dose group II are shown in Table 15 together with the percentage improvement in the PASI score from the baseline.

Dose Group III

Six patients from dose group III received a single intravenous injection of 5.0 mg of BT061 while two patients from dose group III received the placebo. The dose per weight and the dose per body surface area (BSA) for each patient are shown in Table 15B.

The PASI scores for the patients in dose group III are shown in Table 15B together with the percentage improvement in the PASI score from the baseline.

Dose Group IV

Six patients from dose group IV are receiving a single intravenous injection of 10.0 mg of BT061 while two patients from dose group IV received the placebo. The dose per weight and the dose per body surface area (BSA) for the patients is shown in Table 15C.

The PASI scores for the patients in dose group IV are shown in Table 15C together with the percentage improvement in the PASI score from the baseline.

TABLE 14

| PASI scores for the patients in dose group I (0.5 mg intravenous dose) over the course of the trial | | | | | | | | |
|---|---|---|---|---|---|---|---|---|
| Patient | 1 | 2 | 3 | 4 | 5 | 6 | 7 | 8 |
| Rel. Dose [µg/kg]/ [mg/m$^2$] | 5.2/0.23 | 5.9/0.25 | 4.6/0.22 | 5.3/0.24 | 4.8/0.22 | 8.5/0.31 | 4.7/0.21 | 7.0/0.28 |

TABLE 14-continued

PASI scores for the patients in dose group I (0.5 mg intravenous dose) over the course of the trial

| Patient | 1 | 2 | 3 | 4 | 5 | 6 | 7 | 8 |
|---|---|---|---|---|---|---|---|---|
| | | | | PASI Score (relative change/improvement to baseline) | | | | |
| Baseline | 12.2 | 13.5 | 12.1 | 14.0 | 12.1 | 12.6 | 12.1 | 15.2 |
| Day 5 | 12.6 (2%) | 12.1 (10%) | 9.1 (25%) | 12.2 (13%) | 10.9 (10%) | 11.8 (6%) | 9.4 (22%) | 10.2 (33%) |
| Day 7 | 12.0 (0%) | 10.7 (21%) | 7.7 (36%) | 11.6 (17%) | 11.2 (7%) | 10.7 (15%) | 9.3 (23%) | 9.0 (41%) |
| Day 14 | 11.8 (3%) | 9.5 (30%) | 5.7 (53%) | 9.6 (31%) | 8.7 (28%) | 10.4 (17%) | 7.8 (36%) | 7.2 (53%) |
| Day 21 | 11.6 (5%) | 10.0 (26%) | 5.1 (58%) | 7.2 (49%) | 8.0 (34%) | 8.0 (37%) | 6.0 (50%) | 6.5 (57%) |
| Day 28 | — | 10.4 (23%) | 4.8 (60%) | 8.4 (40%) | 8.2 (32%) | 6.5 (48%) | 6.4 (47%) | 6.4 (58%) |
| Day 42 | 11.4 (7%) | 11.2 (17%) | 5.1 (58%) | 8.4 (40%) | 7.9 (35%) | 6.1 (52%) | 5.5 (55%) | 5.5 (55%) |
| Day 56 | 11.4 (7%) | 10.1 (25%) | 4.2 (65%) | 9.2 (34%) | 7.9 (35%) | 5.7 (55%) | 5.3 (56%) | 5.3 (56%) |
| Day 75 | 11.6 (5%) | 7.7 (43%) | 5.1 (58%) | 9.8 (30%) | 9.6 (21%) | 5.1 (60%) | 5.4 (55%) | 7.8 (49%) |

TABLE 15A

PASI scores for the patients in dose group II (2.5 mg intravenous dose) over the course of the trial

| Patient | 1 | 2 | 3 | 4 | 5 | 6 | 7 | 8 |
|---|---|---|---|---|---|---|---|---|
| Rel. Dose [μg/kg]/[mg/m²] | 27.8/1.20 | 31.6/1.30 | 31.8/1.28 | 23.6/1.08 | 28.4/1.19 | 39.4/1.49 | 26.5/1.17 | 28.4/1.19 |
| | | | | PASI Score (relative change/improvement to baseline) | | | | |
| Baseline | 17.1 | 13.8 | 10.9 | 18.6 | 15.0 | 12.6 | 13.9 | 13.5 |
| Day 5 | 14.5 (15%) | 15.5 (+12%) | 6.8 (38%) | 17.6 (5) | 12.1 (19%) | 12.6 (0%) | 19.5 (+40%) | 15.6 (+16%) |
| Day 7 | 12.3 (28%) | 13.6 (1%) | 5.2 (52%) | 19.7 (+6%) | 14.0 (7%) | 13.0 (+3%) | 17.0 (+22%) | 14.8 (+10%) |
| Day 14 | 10.8 (37%) | 15.5 (+12%) | 3.9 (64%) | 11.1 (40%) | 11.8 (21%) | 16.6 (+32%) | 11.4 (18%) | 8.0 (41%) |
| Day 21 | 9.7 (43%) | 12.2 (12%) | 3.9 (64%) | 13.7 (26%) | 12.4 (17%) | 11.4 (10%) | 7.9 (43%) | 7.1 (47%) |
| Day 28 | 8.6 (50%) | 9.4 (32%) | 1.5 (86%) | 7.6 (59%) | 12.2 (19%) | 12.8 (+2%) | 8.0 (41%) | 6.5 (52%) |
| Day 42 | 8.8 (49%) | 8.5 (38%) | 1.3 (88%) | 10.2 (45%) | 12.2 (19%) | 11.0 (13%) | 7.8 (44%) | 9.0 (33%) |
| Day 56 | 6.3 (63%) | 8.3 (40%) | 1.3 (88%) | — | 14.2 (5%) | 9.7 (23%) | 8.2 (41%) | 7.8 (42%) |
| Day 75 | 6.0 (65%) | 5.6 (59%) | 1.9 (83%) | 9.2 (51%) | 14.7 (2%) | 10.4 (17%) | 10.2 (27%) | 8.1 (40%) |

TABLE 15B

PASI scores for the patients in dose group III (5.0 mg intravenous dose) over course of trial

| Patient | 1 | 2 | 3 | 4 | 5 | 6 | 7 | 8 |
|---|---|---|---|---|---|---|---|---|
| Rel. Dose [μg/kg]/[mg/m²] | 70.4/2.73 | 57.5/2.40 | 43.9/ | 59.5/ | 52.4/ | 56.8/ | 71.4/ | 66.2/ |
| | | | | PASI Score (relative change/improvement to baseline) | | | | |
| Baseline | 15.8 | 14.1 | 17.4 | 12.4 | 17.3 | 12.4 | 13.5 | 10.4 |
| Day 5 | 13.0 (18%) | 27.2 (+93%) | 17.7 (+2%) | 12.0 (3%) | 16.8 (3%) | 10.6 (1.5%) | — | — |
| Day 7 | 14.3 (9%) | 18.9 (+34%) | 15.6 (10%) | 11.1 (10%) | 17.6 (+2%) | 11.4 (8%) | 11.0 (19%) | 8.2 (21%) |
| Day 14 | 13.5 (15%) | 30.3 (+115%) | 14.0 (20%) | 9.3 (25%) | 14.4 (17%) | 13.0 (+5%) | 9.4 (30%) | 7.6 (27%) |
| Day 21 | 10.1 (36%) | 23.1 (+64%) | 14.4 (17%) | 9.2 (26%) | 14.7 (15%) | 11.6 (6%) | 9.4 (30%) | — |
| Day 28 | 9.6 (39%) | 23.1 (+64%) | 13.4 (23%) | 10.2 (18%) | 13.8 (20%) | 11.2 (10%) | 8.3 (39%) | 8.6 (17%) |
| Day 42 | 9.2 (42%) | 20.1 (+43%) | 14.4 (17%) | 10.2 (18%) | 13.2 (24%) | 12.6 (+2%) | 8.3 (39%) | — |
| Day 56 | 10.0 (37%) | 20.1 (+43%) | 15.8 (9%) | — | 13.2 (24%) | 10.6 (15%) | 9.6 (20%) | — |
| Day 75 | 12.8 (19%) | 22.5 (+60%) | 16.0 (8%) | 9.0 (27%) | 13.2 (24%) | 13.2 (+6%) | 13.4 (1%) | 9.6 (8%) |

TABLE 15C

PASI scores for the patients in dose group IV (10.0 mg intravenous dose) over course of trial

| Patient | 1 | 2 | 3 | 4 | 5 | 6 | 7 | 8 |
|---|---|---|---|---|---|---|---|---|
| Rel. Dose [μg/kg]/[mg/m²] | 173.0/ | 142.9/ | 102.8/ | 115.6/ | 119.6/ | 108.8/ | 75.9/ | 106.6/ |
| | | | | PASI Score (relative change/improvement to baseline) | | | | |
| Baseline | 14.6 | 11.0 | 21.6 | 22.0 | 19.0 | 11.6 | 14.0 | 12.4 |
| Day 5 | 12.8 (12%) | 11.0 (0%) | 21.6 (0%) | 16.8 (24%) | 18.8 (1%) | 11.2 (3%) | 14.2 (+1%) | 11.4 (8%) |
| Day 7 | 12.8 (12%) | 11.0 (0%) | 21.6 (0%) | 16.8 (24%) | 18.2 (4%) | 11.2 (3%) | 14.2 (+1%) | 8.4 (32%) |
| Day 14 | 11.4 (22%) | 11.0 (0%) | 21.6 (0%) | 18.1 (18%) | 16.7 (12%) | | | |

TABLE 15C-continued

PASI scores for the patients in dose group IV (10.0 mg intravenous dose) over course of trial

| Patient | 1 | 2 | 3 | 4 | 5 | 6 | 7 | 8 |
|---|---|---|---|---|---|---|---|---|
| Day 21 | 11.4 (22%) | 11.0 (0%) | 22.5 (+4%) | 19.0 (14%) | 17.3 (9%) | | | |
| Day 28 | 11.4 (22%) | 8.9 (19%) | 22.0 (7%) | 17.7 (20%) | | | | |
| Day 42 | 11.0 (25%) | 9.4 (15%) | 22.6 (+5%) | 18.8 (15%) | | | | |
| Day 56 | 11.4 (22%) | 9.8 (11%) | | | | | | |
| Day 75 | | | | | | | | |

Further, the PASI scores against time for individual patients are shown in graph form in FIGS. 12A to 12H and in FIGS. 13A to 13H. The graphs shown in FIGS. 12A to 12H represent PASI scores for patients from dose group I, while the graphs shown in FIGS. 13A to 13H represent PASI scores for patients from dose group II.

As can be seen from the results shown in Tables 14 and 15, 75% of all the patients from dose group I and dose group II show a clear improvement in their PASI scores, i.e. at least a 40% improvement over the baseline value, after a single dose. It should be noted that 25% of the patients in dose group I and dose group II received a placebo.

In fact, in both dose groups 50% of the patients showed at least 50% improvement in their PASI scores, with one patient in dose group II showing an 88% improvement in the PASI score at day 56, (i.e. patient 3 in Table 15). Furthermore, the therapeutic effect is long-lasting even at these low doses, with the improvements still being seen in many patients at the end of the trial, 75 days after administration.

Patients in dose group III also show an improvement in their PASI score, with six out of eight patients showing a greater than 20% improvement and two of those six showing a greater than 30% improvement after treatment. However, the improvement was not as significant as that seen in patients from dose group I and dose group II which received a lower dose of the antibody. Some efficacy is also seen in the patients of dose group IV. In particular patients 1, 4, 5 and 8 in this dose group (as shown in Table 15C) show a clear improvement in their PASI scores, although this is limited in comparison to the patients of dose groups I to III.

The number of patients showing at least 40%, 50%, 60% and 75% improvement in PASI score is shown in Table 16.

TABLE 16

Summary of results from Dose Groups I to III

| | Dose group I*<br>0.5 mg BT-061 | Dose group II*<br>2.5 mg BT-061 | Dose Group III*<br>5.0 mg BT061 |
|---|---|---|---|
| Improvement ≥40% | 6/8 patients | 6/8 patients | 1/8 patients |
| Improvement ≥50% | 4/8 patients | 4/8 patients | 0/8 patients |
| Improvement ≥60% | 1/8 patients | 2/8 patients | 0/8 patients |
| Improvement ≥75% | 0/8 patients | 1/8 patients | 0/8 patients |

Figure 14A:
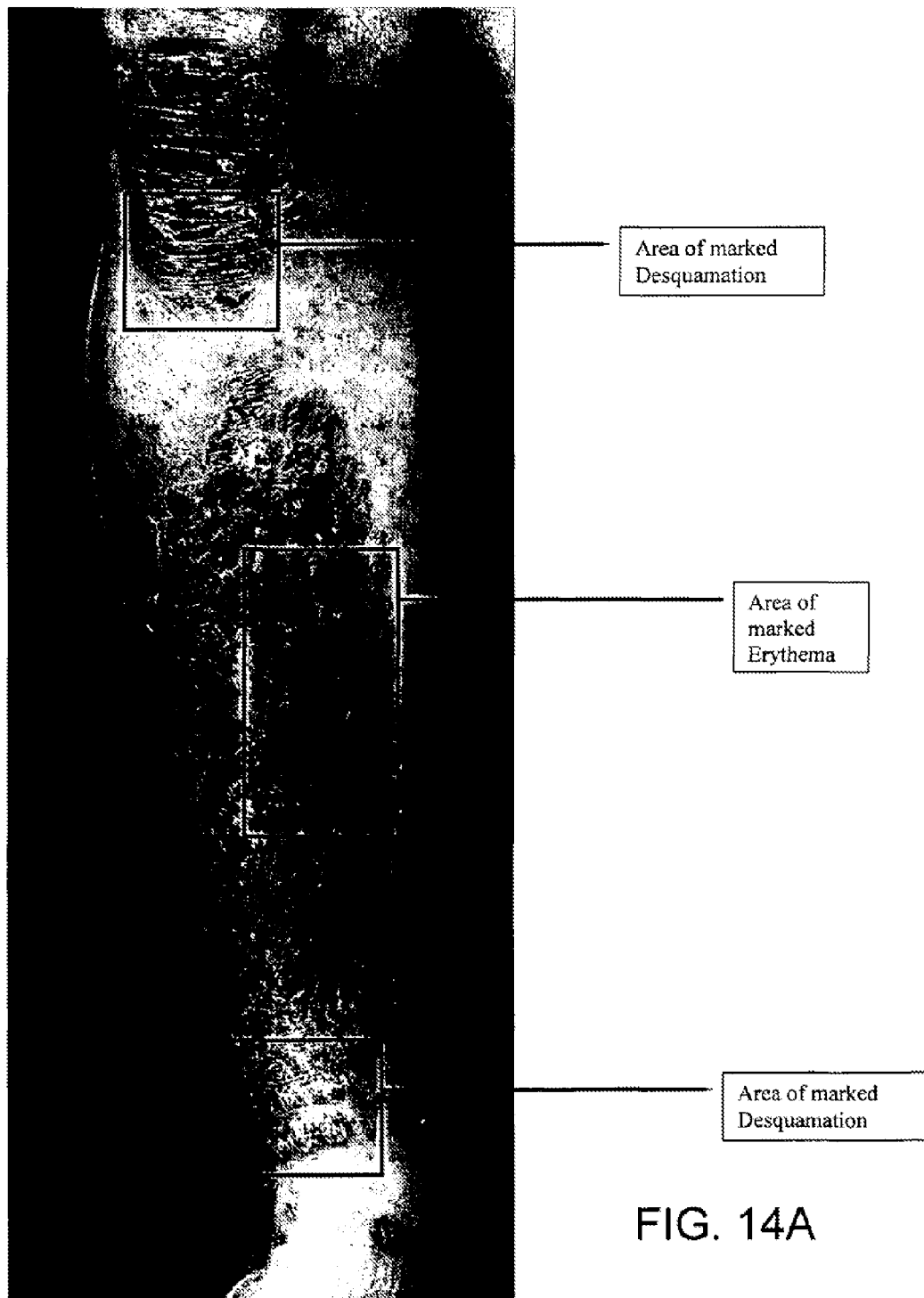
FIG. 14 parts A and B provide photographs from the clinical trial with psoriasis patients as described in Example 8. The photographs are of the same patient who was a member of dose group II. The photograph shown in part A was taken prior to treatment. The photograph shown in part B was taken 28 days after treatment.
Figure 14B:
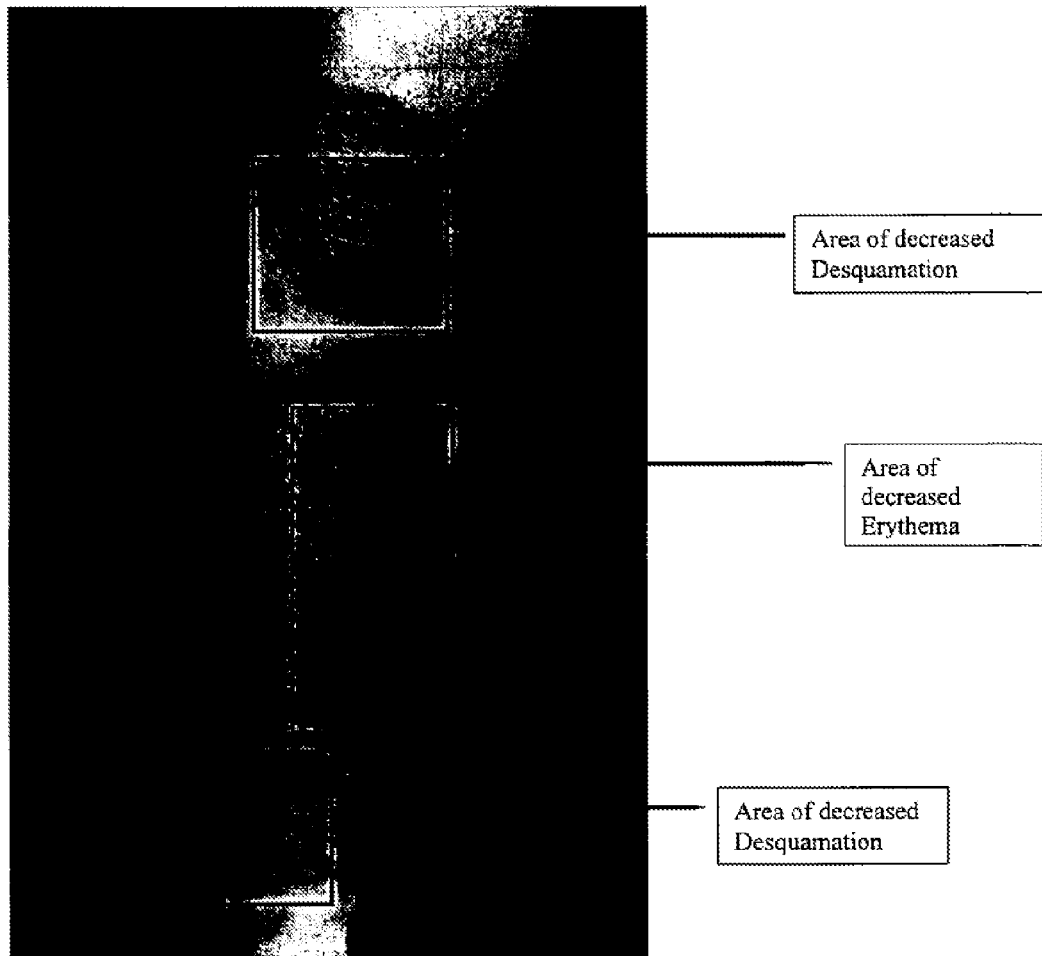

*per dose group: 75% of patients received BT061, 25% of patients received placebo FIGS. 14 A and 14 B provide photographic evidence of the improvement in the level of psoriasis before and after treatment. FIG. 14 A shows an area of psoriasis on the skin of a patient in dose group II prior to administration. FIG. 14 B shows the same area of psoriasis 28 days after administration. The areas of improvement are marked on FIG. 14 B with black boxes.

From these results it can clearly be seen that BT061 provides effective treatment of moderate and severe chronic psoriasis.

The results of this study, in combination with those described above in Example 7 which show that even high doses of the antibody of the invention are generally well-tolerated in humans, demonstrate the ability of the pharmaceutical compositions of the invention to provide effective long term treatment of autoimmune diseases with the dosage regimens described herein.

Example 9

Clinical Trial of BT061 in Patients with Rheumatoid Arthritis

The ability of BT061 to treat rheumatoid arthritis is being tested on patients suffering from this disease. The trial comprises a multiple dose study involving 96 patients, divided into 12 groups. In each group two patients receive a placebo while 6 patients receive BT061. Patients are dosed once a week over a period of 6 weeks.

Patients are divided into those receiving the antibody subcutaneously and those receiving the antibody intravenously. The subcutaneous dose groups are: 1.25 mg, 6.25 mg, 12.5 mg, 25 mg, 50 mg, 75 mg and 100 mg. The intravenous dose groups are: 0.5 mg, 2 mg, 6.25 mg, 12.5 mg and 25 mg.

In the 1.25 mg subcutaneous dose group the patients are numbered 101, 102, 103, 104, 105, 106, 107 and 108. In the 6.25 mg subcutaneous dose group the patients are numbered 201-208. In the 12.5 mg subcutaneous dose group the patients are numbered 301-308. In the 25 mg subcutaneous dose group the patients are numbered 401-408. In the 50 mg subcutaneous dose group the patients are numbered 501-508. In the 6.25 mg intravenous dose group the patients are numbered 601-608.

The intravenous and subcutaneous administration procedure was the same as that described in Example 8 for the psoriasis trial.

The level of rheumatoid arthritis is recorded weekly by assessing the ACR parameters and in particular studying the number of tender and swollen joints and following the levels of C-reactive protein (CRP) and the erythrocyte sedimentation rate (ESR). These parameters are assessed before the trial to provide a "baseline" value at day 0, and repeatedly during the trial period and thereafter at 8, 22 and 43 days after the administration period is finished (i.e. follow up (FU) day 8, FU day 22 and FU day 43).

The Tables below provide the data obtained from the trial. Specifically Tables 17 to 22 provide the number of tender and swollen joints over the course of the trial.

TABLE 17

Tender and swollen joint counts from the 1.25 mg subcutaneous dose group.

| Patients - 1.25 mg SC dose group | Joints (no.) | Screen Visit | Day 1 Week 1 | Day 8 Week 2 | Day 15 Week 3 | Day 22 Week 4 | Day 29 Week 5 | Day 36 Week 6 | Follow-up Day 43 Week 7 | Follow-up Day 57 Week 9 | Follow-up Day 78 Week 12 |
|---|---|---|---|---|---|---|---|---|---|---|---|
| 101 | tender | 34 | 34 | 32 | — | — | — | — | — | — | 0 |
|  | swollen | 10 | 10 | 18 | — | — | — | — | — | — | 0 |
| 102 | tender | 25 | 26 | 22 | 16 | 16 | 24 | 24 | 30 | 28 | 29 |
|  | swollen | 12 | 13 | 9 | 10 | 9 | 15 | 12 | 9 | 18 | 15 |
| 103 | tender | 11 | 12 | 12 | 9 | 8 | 7 | 7 | 30 | 28 | 3 |
|  | swollen | 7 | 8 | 8 | 6 | 6 | 6 | 6 | 9 | 18 | 2 |
| 104 | tender | 17 | 10 | 4 | 3 | 20 | 17 | 9 | 5 | 5 | 0 |
|  | swollen | 8 | 6 | 0 | 0 | 0 | 8 | 2 | 0 | 0 | 0 |
| 105 | tender | 24 | 23 | 22 | 23 | 35 | 32 | 35 | 32 | 34 | 33 |
|  | swollen | 14 | 14 | 14 | 17 | 18 | 18 | 19 | 19 | 20 | 20 |
| 106 | tender | 20 | 21 | 20 | 13 | 8 | 9 | 13 | 12 | 11 | 11 |
|  | swollen | 9 | 12 | 9 | 10 | 5 | 5 | 6 | 5 | 5 | 7 |
| 107 | tender | 14 | 14 | 11 | 10 | 16 | 14 | 14 | 14 | 11 | 11 |
|  | swollen | 8 | 9 | 8 | 8 | 5 | 5 | 5 | 6 | 6 | 6 |
| 108 | tender | 11 | 12 | 10 | 10 | 7 | 4 | 8 | 8 | 2 | 13 |
|  | swollen | 10 | 11 | 7 | 11 | 10 | 9 | 11 | 7 | 6 | 8 |

TABLE 18

Tender and swollen joint counts from the 6.25 mg subcutaneous dose group.

| Patients - 6.25 mg SC dose group | Joints (no.) | Screen Visit | Day 1 Week 1 | Day 8 Week 2 | Day 15 Week 3 | Day 22 Week 4 | Day 29 Week 5 | Day 36 Week 6 | Follow-up Day 43 Week 7 | Follow-up Day 57 Week 9 | Follow-up Day 78 Week 12 |
|---|---|---|---|---|---|---|---|---|---|---|---|
| 201 | tender | 16 | 17 | 15 | 14 | 12 | 15 | 13 | 11 | 9 | 9 |
|  | swollen | 9 | 10 | 7 | 6 | 6 | 5 | 6 | 5 | 6 | 6 |
| 202 | tender | 14 | 10 | 10 | 10 | 8 | 8 | 8 | 8 | 9 | 13 |
|  | swollen | 10 | 8 | 6 | 6 | 4 | 4 | 4 | 4 | 4 | 6 |
| 203 | tender | 15 | 14 | 10 | 8 | 10 | 10 | 8 | 7 | 5 | 5 |
|  | swollen | 11 | 11 | 10 | 9 | 9 | 10 | 7 | 7 | 6 | 7 |
| 204 | tender | 19 | 22 | 16 | 0 | 0 | 10 | 2 | 10 | 11 | 0 |
|  | swollen | 10 | 10 | 5 | 0 | 0 | 4 | 0 | 0 | 10 | 0 |
| 205 | tender | 21 | 21 | 0 | 0 | 14 | 30 | 10 | 37 | — | 12 |
|  | swollen | 9 | 9 | 0 | 0 | 14 | 16 | 6 | 25 | — | 8 |
| 206 | tender | 16 | 16 | 15 | 13 | 13 | 17 | 19 | — | — | 5 |
|  | swollen | 10 | 12 | 12 | 10 | 14 | 11 | 11 | — | — | 4 |
| 207 | tender | 17 | 28 | 28 | 11 | 9 | 15 | 17 | 14 | 18 | 22 |
|  | swollen | 11 | 12 | 13 | 7 | 10 | 11 | 8 | 10 | 11 | 10 |
| 208 | tender | 13 | 12 | 9 | 8 | 9 | 11 | 10 | — | — | 12 |
|  | swollen | 10 | 10 | 9 | 9 | 10 | 10 | 9 | — | — | 8 |

TABLE 19

Tender and swollen joint counts from the 12.5 mg subcutaneous dose group.

| Patients - 12..5 mg SC dose group | Joints (no.) | Screen Visit | Day 1 Week 1 | Day 8 Week 2 | Day 15 Week 3 | Day 22 Week 4 | Day 29 Week 5 | Day 36 Week 6 | Follow-up Day 43 Week 7 | Follow-up Day 57 Week 9 | Follow-up Day 78 Week 12 |
|---|---|---|---|---|---|---|---|---|---|---|---|
| 301 | tender | 18 | 18 | 16 | 16 | 16 | 16 | 16 | 20 | 14 | 14 |
|  | swollen | 8 | 8 | 8 | 8 | 8 | 8 | 8 | 6 | 6 | 6 |
| 302 | tender | 36 | 36 | 34 | 35 | 31 | — | — | — | — | 30 |
|  | swollen | 20 | 20 | 19 | 19 | 17 | — | — | — | — | 18 |
| 303 | tender | 20 | 19 | 19 | 16 | 15 | 14 | 16 | 18 | — | 19 |
|  | swollen | 10 | 11 | 12 | 13 | 13 | 14 | 13 | 14 | — | 14 |
| 304 | tender | 10 | 10 | 10 | 10 | 10 | 10 | 10 | 10 | 10 | 8 |
|  | swollen | 6 | 6 | 6 | 6 | 6 | 6 | 6 | 6 | 6 | 4 |
| 305 | tender | 16 | 16 | 14 | 14 | 13 | 13 | 13 | 12 | 10 | 10 |
|  | swollen | 8 | 8 | 8 | 8 | 6 | 6 | 6 | 6 | 4 | 4 |
| 306 | tender | 27 | 27 | 18 | 18 | 12 | 23 | 28 | — | — | 29 |
|  | swollen | 14 | 14 | 20 | 11 | 16 | 13 | 17 | — | — | 24 |

TABLE 19-continued

Tender and swollen joint counts from the 12.5 mg subcutaneous dose group.

| Patients - 12..5 mg SC dose group | Joints (no.) | Screen Visit | Day 1 Week 1 | Day 8 Week 2 | Day 15 Week 3 | Day 22 Week 4 | Day 29 Week 5 | Day 36 Week 6 | Follow-up Day 43 Week 7 | Follow-up Day 57 Week 9 | Follow-up Day 78 Week 12 |
|---|---|---|---|---|---|---|---|---|---|---|---|
| 307 | tender | 25 | 23 | 23 | 17 | 17 | 17 | 17 | 15 | 13 | 11 |
|  | swollen | 8 | 8 | 8 | 8 | 8 | 8 | 8 | 6 | 6 | 4 |
| 308 | tender | 20 | 20 | 18 | 8 | 8 | 8 | 8 | 8 | 8 | 4 |
|  | swollen | 12 | 12 | 8 | 6 | 6 | 5 | 6 | 6 | 6 | 4 |

TABLE 20

Tender and swollen joint counts from the 25 mg subcutaneous dose group.

| Patients - 25 mg SC dose group | Joints (no.) | Screen Visit | Day 1 Week 1 | Day 8 Week 2 | Day 15 Week 3 | Day 22 Week 4 | Day 29 Week 5 | Day 36 Week 6 | Follow-up Day 43 Week 7 | Follow-up Day 57 Week 9 | Follow-up Day 78 Week 12 |
|---|---|---|---|---|---|---|---|---|---|---|---|
| 401 | tender | 16 | 17 | 19 | 22 | 13 | 13 | 12 | 11 | 9 | 6 |
|  | swollen | 10 | 11 | 8 | 9 | 12 | 11 | 8 | 5 | 8 | 5 |
| 402 | tender | 23 | 21 | 10 | 10 | 10 | 9 | 8 | 7 | 6 | 7 |
|  | swollen | 8 | 11 | 5 | 6 | 6 | 5 | 4 | 3 | 3 | 3 |
| 403 | tender | 10 | 10 | 10 | 8 | 8 | 10 | 10 | 7 | 6 | 8 |
|  | swollen | 8 | 8 | 8 | 6 | 5 | 5 | 5 | 5 | 5 | 5 |
| 404 | tender | 17 | 16 | 15 | 15 | 13 | 14 | 14 | 16 |  |  |
|  | swollen | 9 | 11 | 10 | 6 | 7 | 7 | 7 | 7 |  |  |
| 405 | tender | 10 | 10 | 8 | 8 | 8 | 8 | 8 | 10 | — | 10 |
|  | swollen | 6 | 6 | 4 | 4 | 4 | 4 | 4 | 6 | — | 6 |
| 406 | tender | 11 | 11 | 11 | 11 | 11 | 12 | 8 | 8 | 6 | 8 |
|  | swollen | 6 | 6 | 6 | 6 | 5 | 5 | 3 | 3 | 2 | 4 |
| 407 | tender | 13 | 20 | 16 | 18 | 4 | 2 | 0 | 4 | 14 |  |
|  | swollen | 7 | 10 | 6 | 8 | 0 | 0 | 0 | 0 | 8 |  |
| 408 | tender | 11 | 11 | 8 | 8 | 7 | 5 | 4 | 4 | — | 8 |
|  | swollen | 9 | 9 | 5 | 5 | 4 | 6 | 6 | 3 | — | 6 |

TABLE 21

Tender and swollen joint counts from the 50 mg subcutaneous dose group.

| Patients - 50 mg SC dose group | Joints (no.) | Screen Visit | Day 1 Week 1 | Day 8 Week 2 | Day 15 Week 3 | Day 22 Week 4 | Day 29 Week 5 | Day 36 Week 6 | Follow-up Day 43 Week 7 | Follow-up Day 57 Week 9 | Follow-up Day 78 Week 12 |
|---|---|---|---|---|---|---|---|---|---|---|---|
| 501 | tender | 10 | 10 | 12 | 15 | 12 | 15 | 16 | — | — | 15 |
|  | swollen | 10 | 10 | 10 | 10 | 10 | 13 | 13 | — | — | 13 |
| 502 | tender | 14 | 15 | 11 | 16 | 12 | 7 | 8 |  |  |  |
|  | swollen | 5 | 9 | 10 | 10 | 7 | 4 | 5 |  |  |  |
| 503 | tender | 13 | 13 | 11 | 7 | 7 | 6 | 6 | 5 | 5 |  |
|  | swollen | 8 | 8 | 8 | 6 | 6 | 3 | 3 | 2 | 3 |  |
| 504 | tender | 11 | 12 | 10 | 8 | 7 | 11 | 11 | 13 |  |  |
|  | swollen | 8 | 8 | 8 | 6 | 7 | 7 | 7 | 8 |  |  |
| 505 | tender | 12 | 13 | 8 | 2 | 1 |  |  |  |  |  |
|  | swollen | 7 | 7 | 5 | 0 | 0 |  |  |  |  |  |
| 506 | tender | 36 | 48 | 32 |  |  |  |  |  |  |  |
|  | swollen | 8 | 8 | 4 |  |  |  |  |  |  |  |
| 507 | tender |  |  |  |  |  |  |  |  |  |  |
|  | swollen |  |  |  |  |  |  |  |  |  |  |
| 508 | tender |  |  |  |  |  |  |  |  |  |  |
|  | swollen |  |  |  |  |  |  |  |  |  |  |

TABLE 22

Tender and swollen joint counts from the 6.25 mg intravenous dose group.

| Patients - 6.25 mg IV dose group | Joints (no.) | Visits | | | | | | | | | |
|---|---|---|---|---|---|---|---|---|---|---|---|
| | | Screen Visit | Day 1 Week 1 | Day 8 Week 2 | Day 15 Week 3 | Day 22 Week 4 | Day 29 Week 5 | Day 36 Week 6 | Follow-up Day 43 Week 7 | Follow-up Day 57 Week 9 | Follow-up Day 78 Week 12 |
| 601 | tender | 23 | 20 | 24 | 39 | 33 | 26 | 31 | | | |
| | swollen | 13 | 15 | 15 | 25 | 26 | 20 | 21 | | | |
| 602 | tender | 41 | 43 | 33 | 15 | 12 | 30 | 17 | 19 | 14 | |
| | swollen | 13 | 12 | 8 | 10 | 10 | 6 | 5 | 5 | 7 | |
| 603 | tender | 26 | 22 | 28 | 22 | 24 | 24 | | | | |
| | swollen | 10 | 4 | 8 | 4 | 4 | 6 | | | | |
| 604 | tender | 28 | 26 | 31 | 27 | 14 | 10 | 11 | 7 | 9 | |
| | swollen | 8 | 8 | 8 | 10 | 6 | 2 | 2 | 3 | 1 | |
| 605 | tender | 34 | 38 | 38 | 36 | | | | | | |
| | swollen | 22 | 18 | 22 | 20 | | | | | | |
| 606 | tender | 12 | 14 | | | | | | | | |
| | swollen | 8 | 9 | | | | | | | | |
| 607 | tender | 27 | 27 | | | | | | | | |
| | swollen | 17 | 19 | | | | | | | | |
| 608 | tender | | | | | | | | | | |
| | swollen | | | | | | | | | | |

Figure 15:
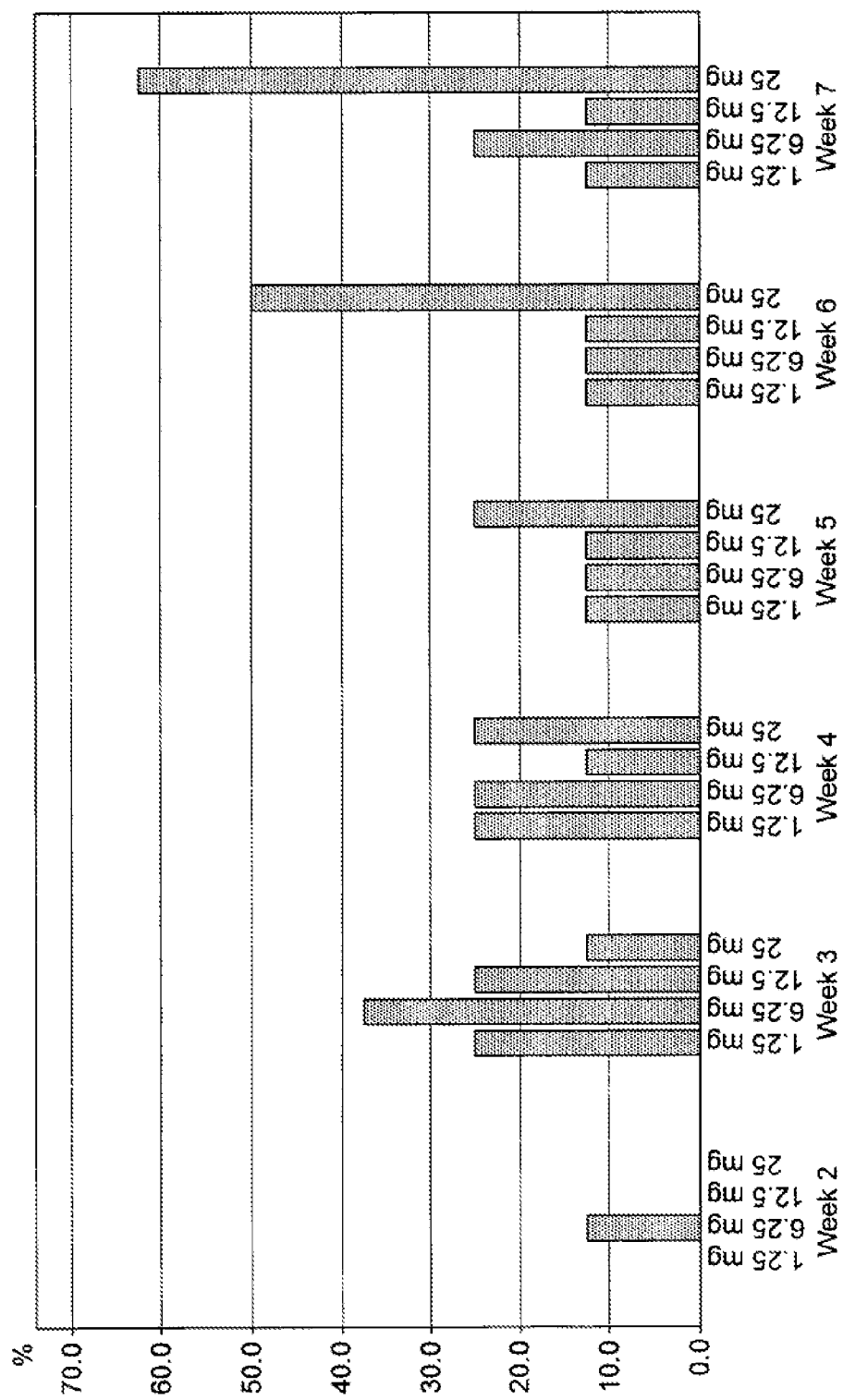
FIG. 15 provides results for the clinical trial with rheumatoid arthritis patients as described in Example 9. The figure shows a bar chart of the percentage of patients from the dose groups receiving 1.25 mg, 6.25 mg, 12.5 mg and 25 mg subcutaneous BT061 achieving at least an ACR20 response. Six patients in each group received the antibody dose while two patients received a placebo.

FIG. 15 shows the percentage of patients from the dose groups receiving 1.25 mg, 6.25 mg, 12.5 mg and 25 mg subcutaneous BT061 achieving at least a 20% improvement of relevant ACR parameters over the course of the trial, and the percentage of patients achieving at least an ACR20 response at week 7.

In particular, it can be seen that 50% of patients in the 25 mg subcutaneous dose group (i.e. 4 out of the 8 patients where 2 of the patients are receiving a placebo) achieved at least a 20% improvement of relevant ACR parameters at week 6. This figures increased to 5 out of the 8 patients at week 7, i.e. 5 out of the 8 patients achieved at least ACR20. One patient in this dose group achieved a more than 50% improvement of relevant ACR parameters at weeks 5 and 6 (full set of data not shown).

Positive results were also obtained by patients in other dose groups. One patients in the 6.25 mg subcutaneous dose group achieved at least a 50% improvement of relevant ACR parameters at week 4 while another achieved at least a 70% improvement of relevant ACR parameters at week 3 (full set of data not shown).

Figure 16A:
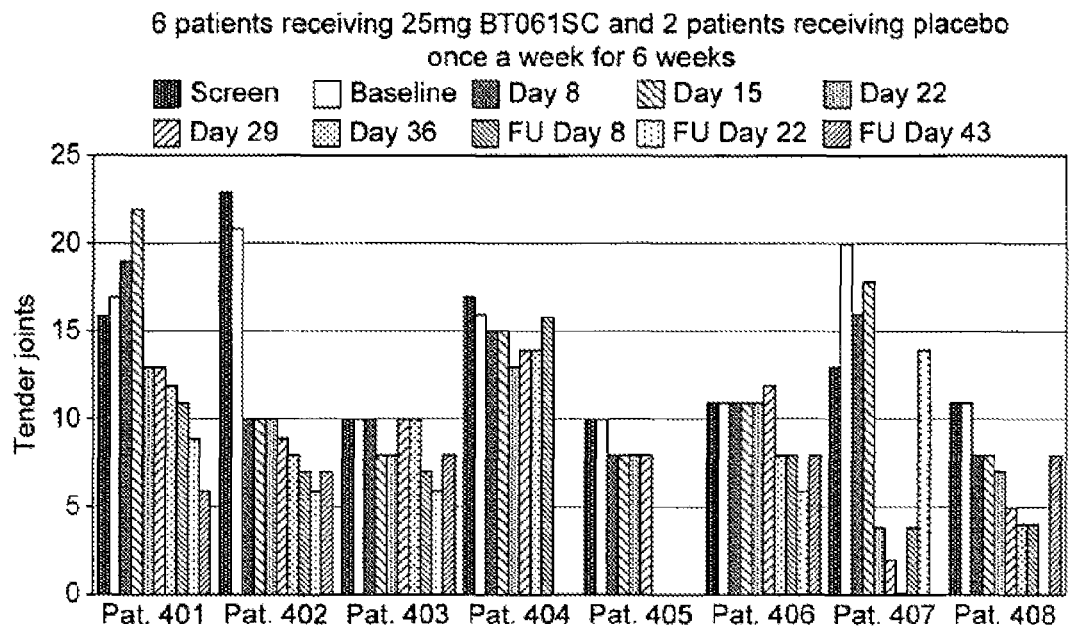
FIGS. 16A and 16B provides results from the clinical trial with rheumatoid arthritis patients as described in Example 9.
Figure 16B:
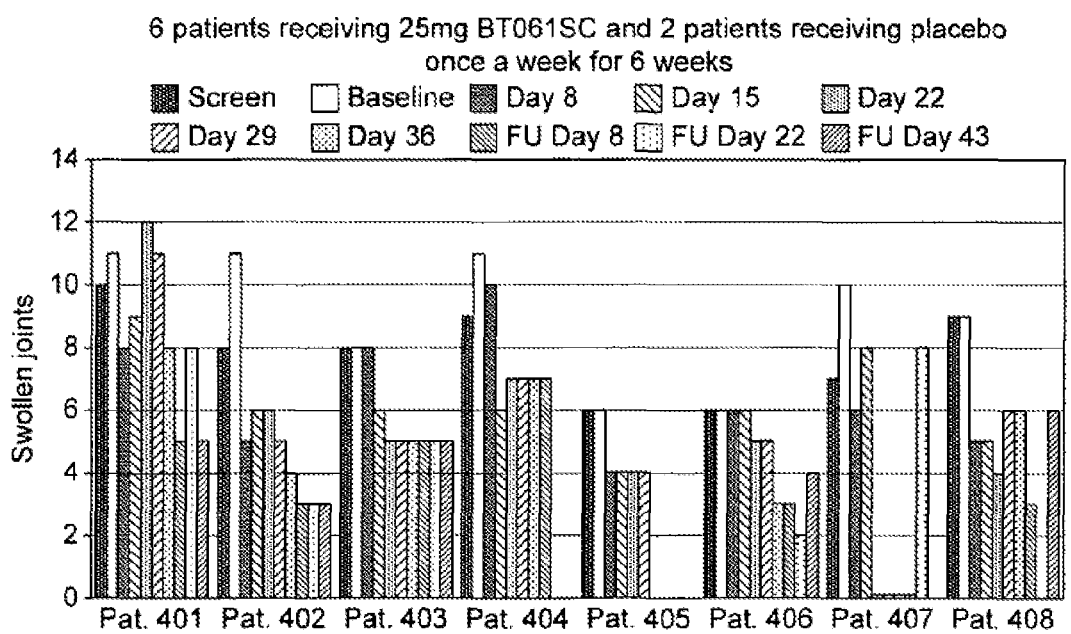
Figure 17A:
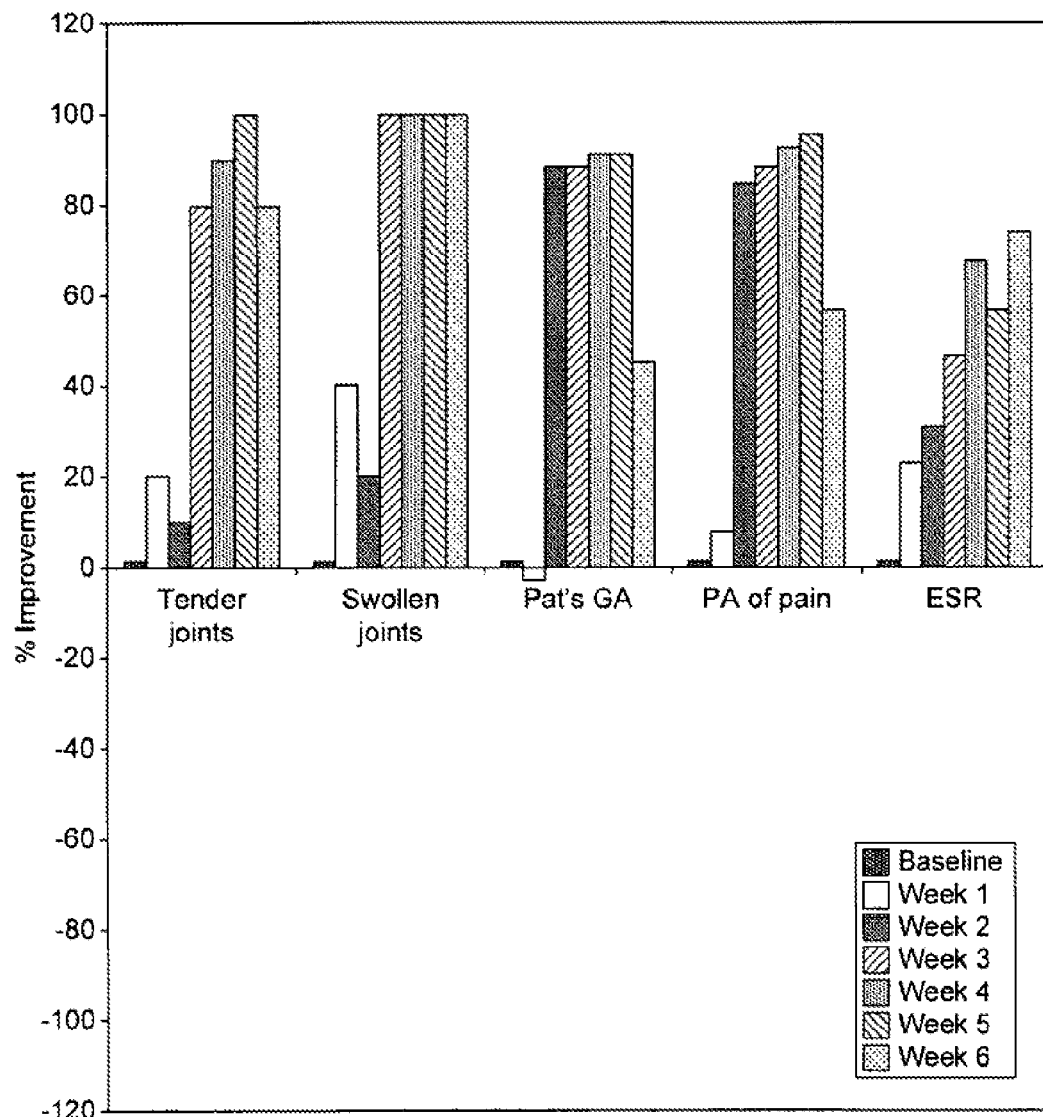
FIGS. 17A and 17B provide results from the clinical trial with rheumatoid arthritis patients as described in Example 9. The Figures show the changes of individual parameters (in %) for one responder (FIG. 17A) and one non-responder (FIG. 17B) from the 25 mg subcutaneous dose group. In the Figures "Pat's GA" and "Phy's GA" refer to the patient's global assessment and physician's global assessment, respectively. The term "PA of pain" refers to the patient's assessment of pain.
Figure 17B:
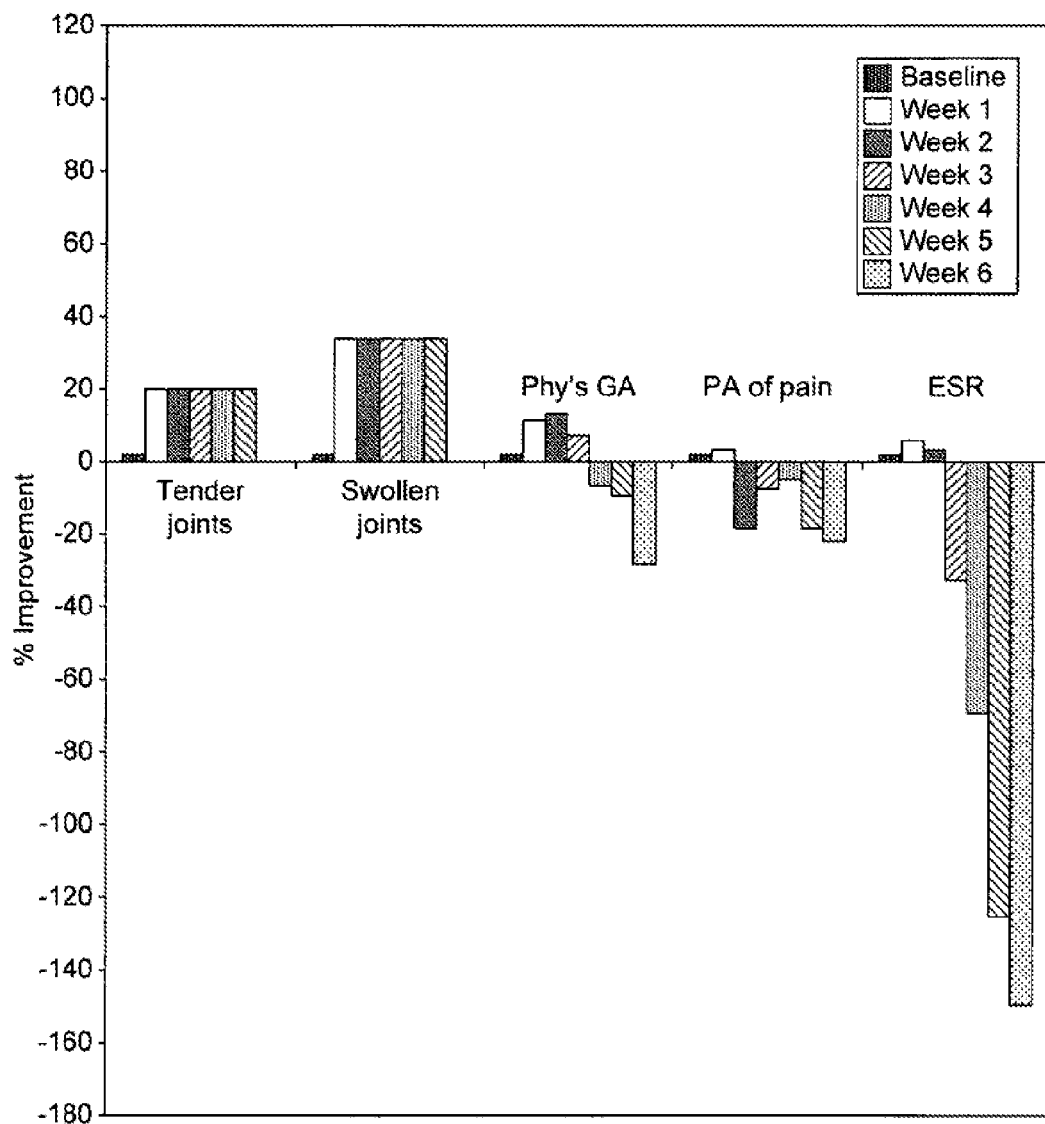
Figure 18A:
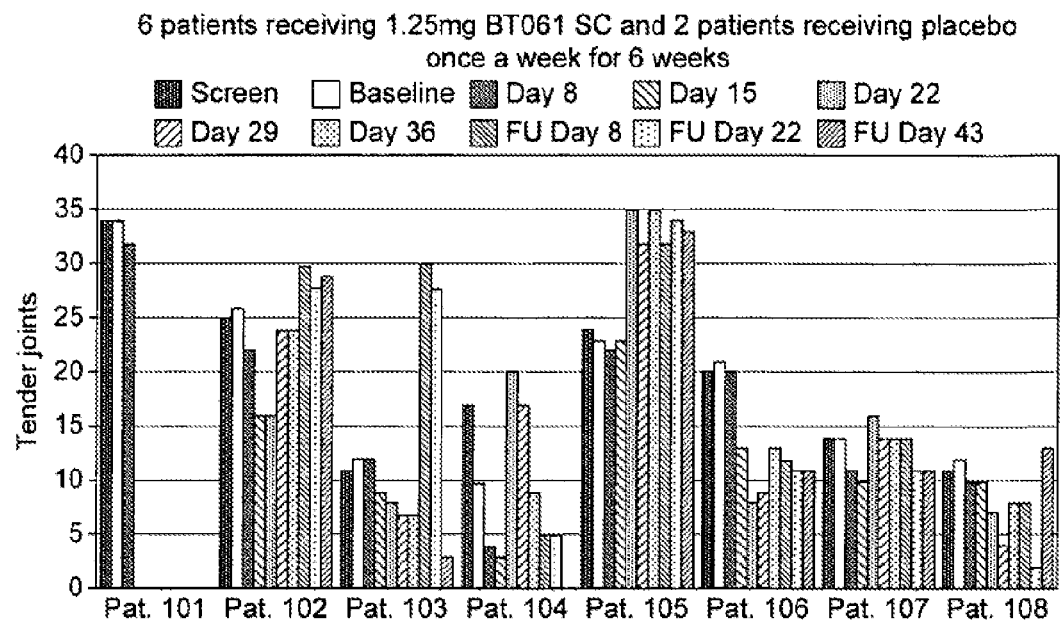
FIGS. 18A and 18B provide further results from the clinical trial with rheumatoid arthritis patients as described in Example 9. The Figures show the number of tender joints in patients from the 1.25 mg subcutaneous dose group (FIG. 18A) and from the 6.25 mg subcutaneous dose group (FIG. 18B).
Figure 18B:
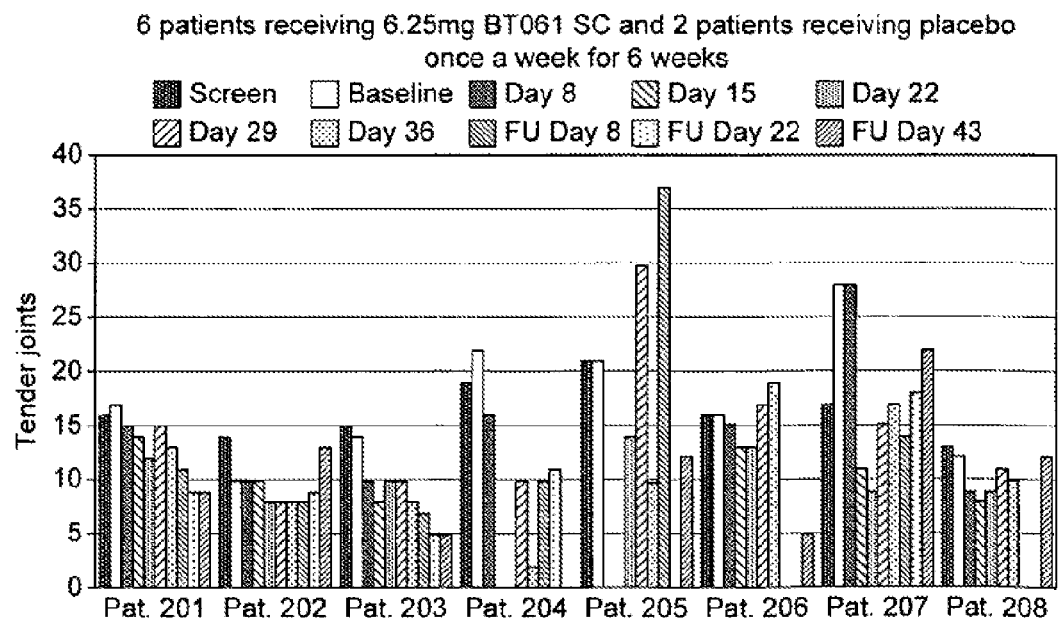
Figure 19A:
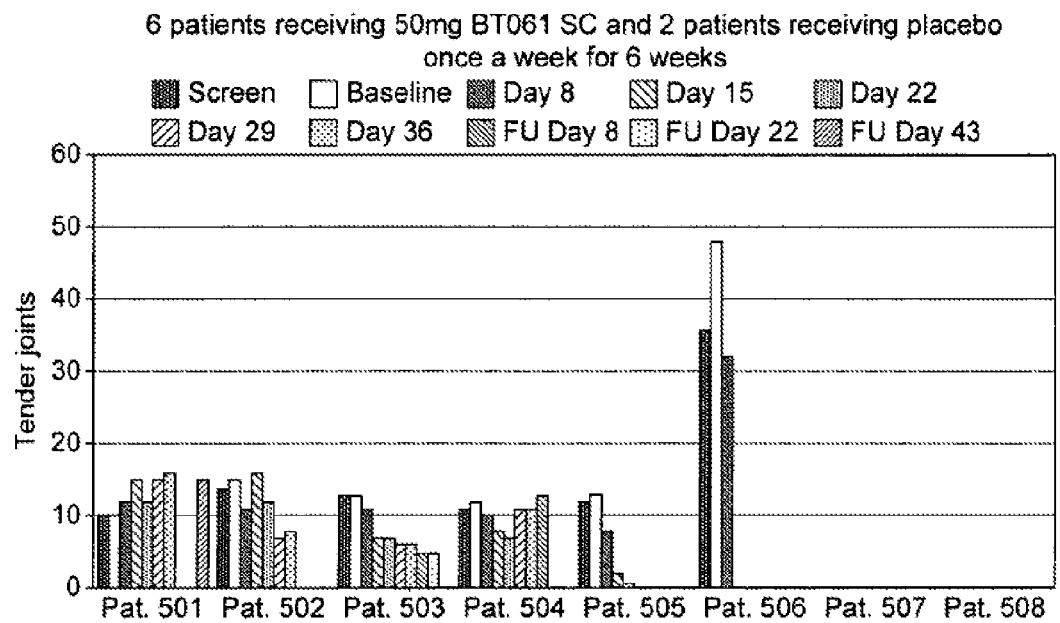
FIGS. 19A and 19B provide further results from the clinical trial with rheumatoid arthritis patients as described in Example 9. The Figures show the number of tender joints in patients from the 50 mg subcutaneous dose group (FIG. 19A) and from the 6.25 mg intravenous dose group (FIG. 19B).
Figure 19B:
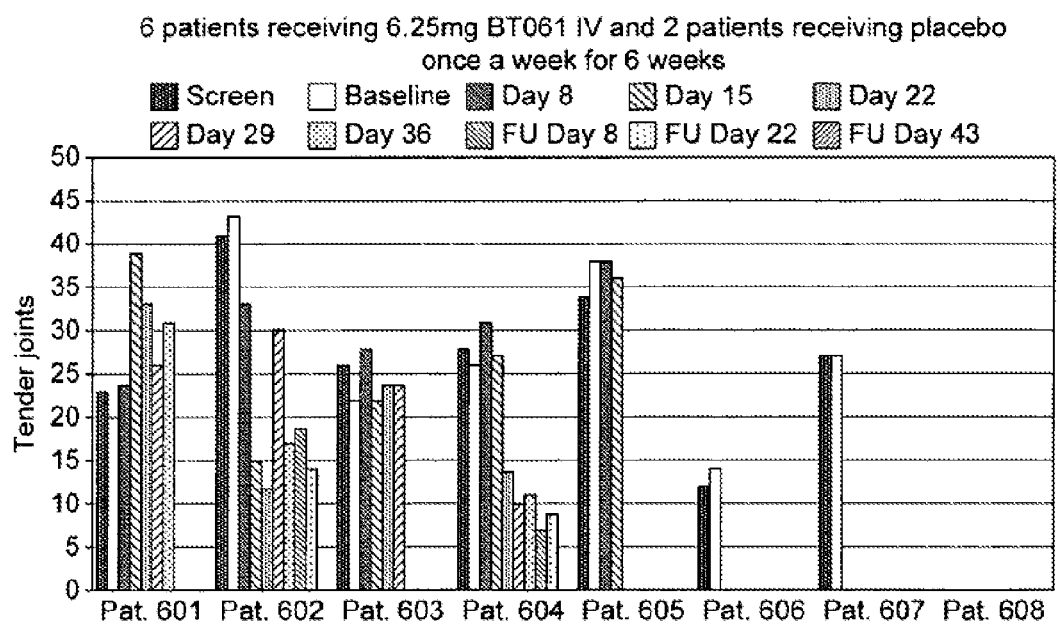

FIGS. 16 A and 16 B show results for the number of tender and swollen joints exhibited by patients from the 25 mg subcutaneous BT061 dose group over a six week period. Several patients exhibit a reduction in the number of tender and swollen joints over a period of the treatment. The results for one responder patient and one non-responder patient from this dose group are shown in FIGS. 17A and 17B, respectively. The responder shows a significant improvement in the number of tender and swollen joints and in pain levels.

A reduction in the numbers of tender and swollen joints is also seen in patients from the other dose groups. FIGS. 18A, 18B, 19A and 19B show the number of tender joints in the 1.25 mg subcutaneous, 6.25 mg subcutaneous, 50 mg subcutaneous and 6.25 mg intravenous dose groups respectively, over the course of the trial and in the weeks thereafter. These results demonstrate the efficacy of the agent of the present invention in the treatment of rheumatoid arthritis within the dose ranges described herein.

We claim:

1. A method for treating an autoimmune disease comprising administering to a subject a pharmaceutical composition comprising a pharmaceutically acceptable carrier and an agent capable of activating CD4+CD25+ regulatory T cells, wherein the agent is a humanized anti-CD4 antibody comprising an IgG1 constant domain, an H chain V domain comprising the CDRs of SEQ ID NO: 7 and an L chain V domain comprising the CDRs of SEQ ID NO: 8;
   wherein said administering occurs from every week to every 31 days at a dose of the humanized anti-CD4 antibody of from 10 to 200 mg;
   and wherein the autoimmune disease is psoriasis.

2. The method of claim 1, wherein said administering occurs at most once every four weeks.

3. The method of claim 1, wherein said administering occurs every week.

4. The method of claim 1, wherein said administering occurs every 10 days.

5. The method of claim 1, wherein said administering occurs every month.

6. The method of claim 1, wherein said administering occurs at a dose of the agent of 10 mg to 100 mg.

7. The method of claim 1, wherein said agent is present in the composition at a concentration of from 1 mg/ml to 100 mg/ml.

8. The method of claim 1, wherein said administering is via parenteral administration.

9. The method of claim 8, said parenteral administration is selected from the group consisting of intramuscular, intravenous, and subcutaneous.

10. The method of claim 9, wherein said administering is via intravenous or subcutaneous administration.

11. The method of claim 1, wherein the humanized anti-CD4 antibody comprises:
   an H chain V domain comprising SEQ ID NO:1 and an L chain V domain comprising SEQ ID NO:2.

12. A method for treating psoriasis comprising administering to a subject a pharmaceutical composition comprising a pharmaceutically acceptable carrier and a humanized anti-CD4 antibody comprising an IgG1 constant domain, an H chain V domain comprising SEQ ID NO: 1 and an L chain V domain comprising SEQ ID NO: 2, wherein said administering comprises administering the composition to the subject every week, every 10 days, or every month, and wherein said administering comprises administering the composition subcutaneously to the subject in an amount of the antibody of 10 mg to 200 mg.

13. A method for treating psoriasis comprising administering to a subject a pharmaceutical composition comprising a pharmaceutically acceptable carrier and a humanized anti-CD4 antibody comprising an IgG1 constant domain, an H chain V domain comprising SEQ ID NO: 1 and an L chain V domain comprising SEQ ID NO: 2, wherein said administering comprises administering the composition subcutaneously to the subject from every week to every 31 days, and wherein said administering comprises administering the composition to the subject in an amount of the antibody of 10 mg to 200 mg.

* * * * *

SEQUENCE LISTING

```
<160> NUMBER OF SEQ ID NOS: 18

<210> SEQ ID NO 1
<211> LENGTH: 124
<212> TYPE: PRT
<213> ORGANISM: Artificial Sequence
<220> FEATURE:
<223> OTHER INFORMATION: V domain of H chain of humanized antibody
      hB-F5H37L

<400> SEQUENCE: 1

Glu Glu Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp Cys
            20                  25                  30

Arg Met Tyr Trp Leu Arg Gln Ala Pro Gly Lys Gly Leu Glu Trp Ile
        35                  40                  45

Gly Val Ile Ser Val Lys Ser Glu Asn Tyr Gly Ala Asn Tyr Ala Glu
    50                  55                  60
```

```
Ser Val Arg Gly Arg Phe Thr Ile Ser Arg Asp Asp Ser Lys Asn Thr
 65                  70                  75                  80

Val Tyr Leu Gln Met Asn Ser Leu Lys Thr Glu Asp Thr Ala Val Tyr
                 85                  90                  95

Tyr Cys Ser Ala Ser Tyr Tyr Arg Tyr Asp Val Gly Ala Trp Phe Ala
            100                 105                 110

Tyr Trp Gly Gln Gly Thr Leu Val Thr Val Ser Ser
        115                 120

<210> SEQ ID NO 2
<211> LENGTH: 111
<212> TYPE: PRT
<213> ORGANISM: Artificial Sequence
<220> FEATURE:
<223> OTHER INFORMATION: V domain of K chain of humanized antibody
      hB-F5L4M

<400> SEQUENCE: 2

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
                 20                  25                  30

Gly Tyr Ser Tyr Ile Tyr Trp Tyr Gln Gln Lys Pro Gly Gln Pro Pro
            35                  40                  45

Lys Leu Leu Ile Tyr Leu Ala Ser Ile Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Glu Leu Pro Trp Thr Phe Gly Gln Gly Thr Lys Val Glu Ile Lys
            100                 105                 110

<210> SEQ ID NO 3
<211> LENGTH: 550
<212> TYPE: DNA
<213> ORGANISM: Artificial Sequence
<220> FEATURE:
<223> OTHER INFORMATION: Part of plasmid encoding V domain of H chain of
      humanized antibody hB-F5

<400> SEQUENCE: 3
gaggagctcc agacaatgtc tgtctccttc ctcatcttcc tgcccgtgct gggcctccca      60
tggggtcagt gtcagggaga tgccgtattc acagcagcat tcacagactg aggggtgttt     120
cactttgctg tttccttttg tctccaggtg tcctgtcaga ggaacagctt gtggagtctg     180
ggggaggctt ggtgaaaccc ggaggttctc tgaggctctc ctgtgcagcc tcgggtttca     240
gtttcagtga ctgccggatg tactgggttc gccaggctcc agggaagggg ctggagtgga     300
ttggtgtgat ttcagtcaaa tctgagaatt atggagcaaa ttatgcagag tctgtgaggg     360
gcagattcac tatttcaaga gatgattcaa aaaacacggt ctatctgcag atgaacagct     420
tgaagaccga agacactgcc gtttattatt gtagtgcctc ctattatagg tacgacgtgg     480
gggcctggtt tgcttactgg ggccaaggga ctctggtcac tgtctcttca ggtaagaatg     540
gccaagcttg                                                           550

<210> SEQ ID NO 4
<211> LENGTH: 498
```

```
<212> TYPE: DNA
<213> ORGANISM: Artificial Sequence
<220> FEATURE:
<223> OTHER INFORMATION: Part of plasmid encoding V domain of K chain of
      humanized antibody hB-F5

<400> SEQUENCE: 4
ggaggatcca attatctgct gacttataat actactagaa agcaaattta aatgacatat      60
ttcaattata tctgagacag cgtgtataag tttatgtata atcattgtcc attcctgact    120
acaggtgcct acggggacat cgtgatgacc cagtctccag actccctggc tgtgtctctg    180
ggcgagaggg ccaccatcaa ctgcagggcc agcaaaagtg tcagtacatc tggctacagt    240
tatatatatt ggtaccagca gaaaccagga cagcctccta agctgctcat ttaccttgca    300
tccatcctag aatctggggt ccctgaccga ttcagtggca gcgggtctgg gacagatttc    360
actctcacca tcagcagcct gcaggctgaa gatgtggcag tttattactg tcagcacagt    420
agggaacttc cgtggacgtt cggccaaggg accaaggtgg aaatcaaacg tgagtagaat    480
ttaaatttta agcttctt                                                  498

<210> SEQ ID NO 5
<211> LENGTH: 372
<212> TYPE: DNA
<213> ORGANISM: Mus musculus

<400> SEQUENCE: 5
caggaatacc ttgtggagac cgggggaggc ttggtgaggc ctggaaattc tctgaaactc      60
tcctgtgtca cctcgggttt cagtttcagt gactgccgga tgtactggct cgccagcct    120 ccagggaagg ggctggagtg gattggtgtg atttcagtca atctgagaa ttatggagca    180 aattatgcag agtctgtgag gggcagattc actatttcaa gagatgattc aaaaagcagt    240
gtctatctgc agatgagcag attgagagag gaagacactg ccacttatta ttgtagtgcc    300
tcctattata ggtacgacgt gggggcctgg tttgcttact ggggccaagg gactctggtc    360
actgtctctg ca                                                        372

<210> SEQ ID NO 6
<211> LENGTH: 383
<212> TYPE: DNA
<213> ORGANISM: Mus musculus

<400> SEQUENCE: 6
gacattgtgc tgacacagtc tccttcttcc ttagttgtat ctctggggca gagggccacc      60
atctcatgca gggccagcaa agtgtcagt acatctggct acagttatat atattggtac    120
caacagatcc caggacagcc acccaaactc ctcatctatc ttgcatccat cctagaatct    180
ggggtccctg gcaggttcag tggcagtggg tctgggacag acttcaccct caacatccat    240
cctgtggagg aggaggatgc tgcaacctat tactgtcagc acagtaggga acttccgtgg    300
acgttcggtg gaggcaccaa gctggagatc aaacgggctg atgctgcacc aactgtatcc    360
atcttcccac catccagtga gca                                            383

<210> SEQ ID NO 7
<211> LENGTH: 124
<212> TYPE: PRT
<213> ORGANISM: Mus musculus

<400> SEQUENCE: 7

Gln Glu Tyr Leu Val Glu Thr Gly Gly Gly Leu Val Arg Pro Gly Asn
```

```
            1               5                  10                 15
          Ser Leu Lys Leu Ser Cys Val Thr Ser Gly Phe Ser Phe Ser Asp Cys
                        20                  25                  30

Arg Met Tyr Trp Leu Arg Gln Pro Pro Gly Lys Gly Leu Glu Trp Ile
                        35                  40                  45

Gly Val Ile Ser Val Lys Ser Glu Asn Tyr Gly Ala Asn Tyr Ala Glu
                   50                  55                  60

Ser Val Arg Gly Arg Phe Thr Ile Ser Arg Asp Asp Ser Lys Ser Ser
          65                  70                  75                  80

Val Tyr Leu Gln Met Ser Arg Leu Arg Glu Glu Asp Thr Ala Thr Tyr
                           85                  90                  95

Tyr Cys Ser Ala Ser Tyr Tyr Arg Tyr Asp Val Gly Ala Trp Phe Ala
                          100                 105                 110

Tyr Trp Gly Gln Gly Thr Leu Val Thr Val Ser Ala
                          115                 120
```

<210> SEQ ID NO 8
<211> LENGTH: 111
<212> TYPE: PRT
<213> ORGANISM: Mus musculus

<400> SEQUENCE: 8

```
          Asp Ile Val Leu Thr Gln Ser Pro Ser Ser Leu Val Val Ser Leu Gly
          1               5                  10                 15

Gln Arg Ala Thr Ile Ser Cys Arg Ala Ser Lys Ser Val Ser Thr Ser
                        20                  25                  30

Gly Tyr Ser Tyr Ile Tyr Trp Tyr Gln Gln Ile Pro Gly Gln Pro Pro
                        35                  40                  45

Lys Leu Leu Ile Tyr Leu Ala Ser Ile Leu Glu Ser Gly Val Pro Gly
                   50                  55                  60

Arg Phe Ser Gly Ser Gly Ser Gly Thr Asp Phe Thr Leu Asn Ile His
          65                  70                  75                  80

Pro Val Glu Glu Glu Asp Ala Ala Thr Tyr Tyr Cys Gln His Ser Arg
                           85                  90                  95

Glu Leu Pro Trp Thr Phe Gly Gly Gly Thr Lys Leu Glu Ile Lys
                          100                 105                 110
```

<210> SEQ ID NO 9
<211> LENGTH: 23
<212> TYPE: PRT
<213> ORGANISM: Homo sapiens

<400> SEQUENCE: 9

```
          Asp Ile Val Met Thr Gln Ser Pro Asp Ser Leu Ala Val Ser Leu Gly
          1               5                  10                 15

Glu Arg Ala Thr Ile Asn Cys
                        20
```

<210> SEQ ID NO 10
<211> LENGTH: 15
<212> TYPE: PRT
<213> ORGANISM: Homo sapiens

<400> SEQUENCE: 10

```
          Trp Tyr Gln Gln Lys Pro Gly Gln Pro Pro Lys Leu Leu Ile Tyr
          1               5                  10                 15
```

<210> SEQ ID NO 11

```
<211> LENGTH: 32
<212> TYPE: PRT
<213> ORGANISM: Homo sapiens

<400> SEQUENCE: 11

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 12
<211> LENGTH: 10
<212> TYPE: PRT
<213> ORGANISM: Homo sapiens

<400> SEQUENCE: 12

Phe Gly Gln Gly Thr Lys Val Glu Ile Lys
1               5                   10

<210> SEQ ID NO 13
<211> LENGTH: 30
<212> TYPE: PRT
<213> ORGANISM: Homo sapiens

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 14
<211> LENGTH: 14
<212> TYPE: PRT
<213> ORGANISM: Homo sapiens

<400> SEQUENCE: 14

Trp Val Arg Gln Ala Pro Gly Lys Gly Leu Glu Trp Val Gly
1               5                   10

<210> SEQ ID NO 15
<211> LENGTH: 32
<212> TYPE: PRT
<213> ORGANISM: Homo sapiens

<400> SEQUENCE: 15

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 16
<211> LENGTH: 11
<212> TYPE: PRT
<213> ORGANISM: Homo sapiens

<400> SEQUENCE: 16

Trp Gly Gln Gly Thr Leu Val Thr Val Ser Ser
1               5                   10

<210> SEQ ID NO 17
<211> LENGTH: 124
<212> TYPE: PRT
<213> ORGANISM: Artificial Sequence
<220> FEATURE:
```

```
<223> OTHER INFORMATION: V domain of the H chain of humanized antibody
      hB-F5H37V

<400> SEQUENCE: 17

Glu Glu Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp Cys
            20                  25                  30

Arg Met Tyr Trp Val Arg Gln Ala Pro Gly Lys Gly Leu Glu Trp Ile
        35                  40                  45

Gly Val Ile Ser Val Lys Ser Glu Asn Tyr Gly Ala Asn Tyr Ala Glu
    50                  55                  60

Ser Val Arg Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Ala Ser Tyr Tyr Arg Tyr Asp Val Gly Ala Trp Phe Ala
            100                 105                 110

Tyr Trp Gly Gln Gly Thr Leu Val Thr Val Ser Ser
        115                 120

<210> SEQ ID NO 18
<211> LENGTH: 111
<212> TYPE: PRT
<213> ORGANISM: Artificial Sequence
<220> FEATURE:
<223> OTHER INFORMATION: V domain of K chain of humanized antibody
      hB-F5L4L

<400> SEQUENCE: 18

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Ile Tyr Trp Tyr Gln Gln Lys Pro Gly Gln Pro Pro
        35                  40                  45

Lys Leu Leu Ile Tyr Leu Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Trp Thr Phe Gly Gln Gly Thr Lys Val Glu Ile Lys
            100                 105                 110
```